United States Patent [19]

Nakao et al.

[11] Patent Number: 5,141,930
[45] Date of Patent: Aug. 25, 1992

[54] FUSED THIOPHENE COMPOUNDS AND USES THEREOF

[75] Inventors: Tohru Nakao, Nakatsu; Hiroshi Tanaka, Fukuoka; Hirotake Yamato, Nakatsu; Takeshi Akagi, Tokyo; Shuzo Takehara, Nakatsu, all of Japan

[73] Assignee: Yoshitomi Pharmaceutical Industries, Ltd., Osaka, Japan

[21] Appl. No.: 726,683

[22] Filed: Jul. 8, 1991

[30] Foreign Application Priority Data

Jul. 6, 1990 [JP] Japan ................. 2-179953
Aug. 31, 1990 [JP] Japan ................. 2-232244
Nov. 27, 1990 [JP] Japan ................. 2-326644
Jan. 11, 1991 [JP] Japan ................. 3-13684
Mar. 14, 1991 [JP] Japan ................. 3-75657

[51] Int. Cl.$^5$ ............... C07D 285/36; C07D 285/38; A61K 31/55; A61K 31/38
[52] U.S. Cl. ........................ 514/211; 514/215; 540/453; 540/455; 540/461; 540/490; 540/521
[58] Field of Search ............. 540/521, 453, 455, 461, 540/490; 514/211, 215

[56] References Cited

U.S. PATENT DOCUMENTS

| 4,735,940 | 4/1988 | Fischer et al. | 512/212 |
| 4,833,142 | 5/1989 | Hartog et al. | 514/524 |
| 4,895,841 | 1/1990 | Sugimoto et al. | 514/212 |

FOREIGN PATENT DOCUMENTS

| 0324610 | 1/1989 | European Pat. Off. | 540/593 |
| 0329168 | 2/1989 | European Pat. Off. | 544/278 |
| 0376607 | 12/1989 | European Pat. Off. | 544/368 |
| 0376633 | 12/1989 | European Pat. Off. | 540/491 |

OTHER PUBLICATIONS

Chemical Abstracts, vol. 55, 1961, col. 23488.
Chemical Abstracts, vol. 59, 1963, col. 3862.
Chemical Abstracts, vol. 64, 1966, col. 586.
Chemical Abstracts, vol. 69, 1968, 18565x.

Primary Examiner—Robert T. Bond
Attorney, Agent, or Firm—Wenderoth, Lind & Ponack

[57] ABSTRACT

A fused thiophene compound of the formula:

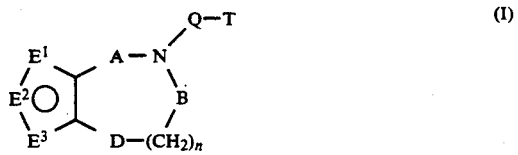

or a pharmaceutically acceptable acid addition salt thereof. In the above formula, one of $E^1$, $E^2$ and $E^3$ is sulfur atom and other two of them are C—$R^1$ and C—$R^2$ respectively. $R^1$ and $R^2$ are the same or different and each is hydrogen, halogen, nitro, amino, cyano, hydroxyl, formyl, alkyl, alkoxy, haloalkyl, arylalkyl, acyl, alkoxyalkyl, acyloxyalkyl, hydroxyalkyl, acyloxyalkanoyl, alkoxyalkanoyl, hydroxyalkanoyl, aryloxyalkanoyl, haloalkanoyl, alkylthio, alkylsulfinyl, alkylsulfonyl, arylthio, arylsulfinyl, arylsulfonyl, hydroxysulfonyl, halosulfonyl, sulfamoyl, substituted sulfamoyl, carboxyl, acylamino, alkoxycharbonyl, carbamoyl, substituted carbamoyl or substituted amino. D is —$CH_2$— or —$S(O)_m$— (m is 0, 1 or 2). Q is straight or branched chain alkylene. T is primary amino, secondary amino or tertiary amino. A and B are the same or different and each is carbonyl or thiocarbonyl, or one of A and B is absent and the other of them is carbonyl or thiocarbonyl, or A is —$CH_2$— and B is carbonyl or thiocarbonyl, and n is 1, 2 or 3 with the proviso that n is 2 or 3 when one of A and B is absent and the other of them is carbonyl or thiocarbonyl, and n is 1 or 2 when A and B are other combinations. In the above definitions, (hetero)aromatic ring and heterocyclic ring may optionally be substituted by 1 to 3 substituents. Said compounds have selective affinity for 5-$HT_{1A}$ receptor, or high affinity for 5-$HT_{1A}$ and dopamine $D_2$ receptors so that they are useful as antianxietic drug, antipsychotic drug or drug for the disease of circulatory system. The intermediates for said fused thiophene compounds are also disclosed.

13 Claims, No Drawings

FUSED THIOPHENE COMPOUNDS AND USES THEREOF

FIELD OF THE INVENTION

The present invention relates to novel and pharmaceutically useful fused thiophene compounds, pharmaceutically acceptable acid addition salts thereof useful as medical agents for central nervous system and circulator system, and pharmaceutical uses thereof, and further novel synthetic intermediated for said fused thiophene compounds.

BACKGROUND OF THE INVENTION

The benzodiazepine compounds have been widely used as antianxietic agents. Though these compounds have potent anxiolytic action, they have side effects such as muscle-relaxation effect, sedative action, drug dependence and so on. Therefore, there are some problems that these agents must be cautiously applied to patients suffering from anxiety neurosis like psychosomatic disease in the daytime (usually called as daytime anxiety). Recently, the researches for compounds having non-benzodiazepine structure have been devoted to the development of antianxietic drugs which act selectively on anxiety. The representative of such compounds is buspirone (INN). Differing from hitherto benzodiazepine compounds, buspirone is known not to bind to benzodiazepine receptor but has high affinity for serotonin 1A receptor and exhibits antianxietic action by an interaction with serotonin 1A receptor. Since such new compounds have superior property such as high safety, less habit-forming and less probability of abuse, they are expected to be new prototype of antianxietic drugs. However, the problems to be solved still remain since they need long time to exhibit their activities and have side effects in extrapyramidal system.

The existing antipsychotic drugs are effective on so called positive symptoms like hallucination, delusion or the like as well as on psychomotor excitement but not effective on negative symptoms like apathy, abulia, disorder of cognition and so on. Further, as unavoidable side effects such as acute dystonia, akathisia or Parkinsonism are observed at the initial stage of treatment with antipsychotic drugs and extrapyramidal syndromes like late dyskinesia are observed during the long term administration. Because of the limitation of the treatment with the existing antipsychotic drugs, the development of antipsychotic drugs which are effective on negative symptoms and with reduced side effects has been expected. From this point of view, it is desired to develop new antipsychotic drugs which have affinity for both serotonin and dopamine receptors, and especially bind more selectively to serotonin receptor.

Recently a relationship between serotonin 1A receptor and hypotensive action has been reported. That is, it is known that 8-hydroxy-2-dipropylaminotetralin (8OH-DPAT) which has high affinity for serotonin 1A receptor lowers blood pressure through serotonin 1A receptor of medulla oblongata. In accordance with this fact, the compounds having high affinity for serotonin 1A receptor can be developed as antihypertensive drug. This kind of compounds are expected to be useful antihypertensive drug because they do not cause rebound phenomenon, hyposalivaton or sympatheticotonia (that is, bradycardic action rather than tachcardiac action). For example, it is known that piperazine derivatives are one of such drugs exhibiting hypotensive action by central action mechanism (U.S. Pat. No. 4,833,142).

SUMMARY OF THE INVENTION

The present inventors have made intensive investigations in order to provide compounds having more potent and selective antianxietic action with less side effects than the existing compounds by selectively binding to serotonin 1A receptor. The present inventors have also investigated to find compounds having affinity for serotonin and dopamine receptors, especially more selective affinity for serontonin receptor which are useful as antipsychotic drugs, and further to find compounds useful as excellent antihypertensive drugs which interact with serotonin 1A receptors and does not increase heart rate.

As a result of such investigations, the present inventors have found novel fused thiophene compounds which accord with the above-mentioned purpose, and completed the present invention. The present invention provides novel fused thiophene compounds useful as anti-anxietic drug, antipsychotic drug or antihypertensive drug and novel synthetic intermediates for the fused thiophene compounds.

DETAILED DESCRIPTION OF THE INVENTION

The present invention relates to a fused thiophene compound of the formula:

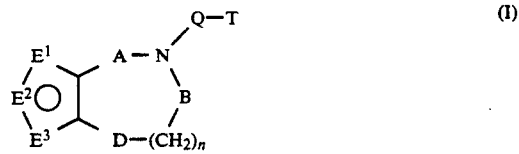 (I)

or a pharmaceutically acceptable acid addition salt thereof.

In the above formula, one of $E^1$, $E^2$ and $E^3$ is sulfur atom and other two of them are $C-R^1$ and $C-R^2$ respectively. $R^1$ and $R^2$ are the same or different and each is hydrogen, halogen, nitro, amino, cyano, hydroxyl, formyl, alkyl, alkoxy, haloalkyl, arylalkyl, acyl, alkoxyalkyl, acyloxyalkyl, hydroxyalkyl, acyloxyalkanoyl, alkoxyalkanoyl, hydroxyalkanoyl, aryloxyalkanoyl, haloalkanoyl, alkylthio, alkylsulfinyl, alkylsulfonyl, arylthio, arylsulfinyl, arylsulfonyl hydroxysulfonyl, halosulfonyl, sulfamoyl substituted sulfamoyl, carboxyl, acylamino, alkoxycarbonyl, carbamoyl, substituted carbamoyl or substituted amino. D is $-CH_2-$ or $-S(O)_m-$ (m is 0, 1 or 2). Q is straight or branched chain alkylene. T is primary amino, secondary amino or tertiary amino. A and B are the same or different and each is carbonyl or thiocarbonyl, or one of A and B is absent and the other of them is carbonyl or thiocarbonyl, or A is $-CH_2-$ and B is carbony or thiocarbonyl, and n is 1, 2 or 3 with the provisos that n is 2 or 3 when one of A and B is absent and the other of them is carbonyl or thiocarbonyl, and M is 1 or 2 when A and B are other combinations. In the above definitions, (hetero)aromatic ring and heterocyclic ring may optionally be substituted by 1 to 3 substituents.

The present invention also provides a fused thiophene compound of the formula:

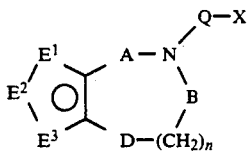

In the above formula, X is hydroxyl, reactive atom or group derived from hydroxyl (e.g. halogen, methanesulfonyloxy, or paratoluenesulfonyloxy), a group of —CO—R³ (R³ is hydrogen or alkyl), cyano, carbamoyl or nitro, and other symbols are as defined above.

In the present specification, the compounds of formula (II) can be subdivided into five groups of the compounds of formula (II-a) to (II-e) as follows:

A compound of formula (II-a): X is hydroxyl, or reactive atom or group derived from hydroxyl.

A compound of formula (II-b): X is —CO—R³ (R³ is hydrogen or alkyl).

A compound of formula (II-c): X is cyano.

A compound of formula (II-d): X is carbamoyl.

A compound of formula (II-e): X is nitro.

The present invention further provides a fused thiophene compound of the formula:

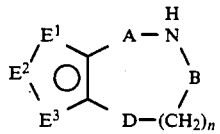

wherein each symbol is as defined above. The compounds of formula (II) and (IV) are synthetic intermediates of the compound of formula (I).

In the definitions of the above symbols and in the present specification, halogen means chlorine, bromine, fluorine, iodine; alkyl means, for example, methyl, ethyl, propyl isopropyl, butyl, isobutyl, tert-butyl, pentyl, hexyl, heptyl, octyl, decyl, hexadecyl or octadecy; alkoxy means, for example, methoxy, ethoxy, propxy, isopropoxy, butoxy, isobutoxy, tert-butoxy, pentyloxy, hexyloxy, heptyloxy or octyloxy; haloalkyl means alkyl substituted by halogen, for example, bromomethyl, chloromethyl, trifluoromethyl, 2-bromoethyl, 2-chloroethyl, difluoromethyl, 2,2-difluoroethyl, 2,2,2-trifluoroethyl, 3-bromopropyl, 3-chloropropyl or 4-fluorobutyl; arylalkyl means, for example, benzyl, 2-phenylethyl, 3-phenylpropyl, 4-phenylbutyl, naphthylmethyl, 2-naphthylethyl, 3-naphthylpropyl, 4-naphthylbutyl, diphenylmethyl or bis(4-fluorophenyl)methyl; acyl means, for example, alkanoyl such as acetyl, propionyl, butyryl, isobutyryl, pentanoyl, hexanoyl or octanoyl, aroyl such as benzoyl or naphthoyl, or heteroarylcarbonyl such as nicotinoyl, thenoyl or furoyl; alkoxyalkyl means, for example, methoxymethyl, 1- or 2-methoxyethyl, 1-, 2- or 3-methoxypropyl, 1-, 2-, 3- or 4-methoxybutyl, ethoxymethyl, 1- or 2-ethoxyethyl, 1-, 2- or 3-ethoxypropyl or 1-, 2-, 3-, or 4-ethoxybutyl; acyoxyalkyl means, for example, acetoxymethyl, propionyloxymethyl, 1- or 2-acetoxyethyl, 1- or 2-propionyloxyethyl, 1-, 2- or 3-acetoxypropyl, 1-, 2- or 3-propionyloxypropyl, benzoyloxymethyl, 1- or 2-benzoyloxyethyl, 1-, 2- or 3-benzoyloxypropyl or 1-, 2-, 3- or 4-benzoyloxybuty; hydroxyalkyl means, for example, hyroxymethyl, 1- or 2-hydroxyethyl, 1-, 2- or 3-hydroxypropyl or 1-, 2-, 3- or 4-hydroxybutyl; acyloxyalkanoyl means, for example, acetoxyacetyl acetoxypropionyl, acetoxybutyryl, benzoyloxyacetyl benzoyloxypropionyl or benzoyloxybutyryl; alkoxyalkanoyl means, for example, methoxyacetyl, ethoxyacetyl, propoxyacetyl, butoxyacetyl, methoxypropionyl, ethoxypropionyl, propoxypropionyl or butoxypropionyl; hydroxyalkanoyl means, for example, hydroxyacetyl, hydroxypropionyl or hydroxybutyryl; aryloxyalkanoyl means, for example, phenoxyacetyl, phenoxypropionyl or phenoxybutyryl; haloalkanoyl means, for example, bromoacetyl, chloroacetyl, bromopropionyl chloropropionyl, bromobutyryl or chlorobutyryl; alkylthio means, for example, methylthio, ethylthio, propylthio, isopropylthio, butylthio, isobutylthio or tert-butylthio; alkylsulfonyl means, for example, methylsulfonyl, ethylsulfonyl, propylsulfonyl, isopropylsulfonyl, butylsulfonyl, isobutylsulfonyl or tert-butylsulfonyl; Halosulfonyl means, for example, chlorosulfonyl, bromosulfonyl or iodosulfonyl; substituted sulfamoyl means, for example, dimethylsulfamoyl, diethylsulfamoyl, dipropylsulfamoyl, dibutylsulfamoyl, piperidinosulfonyl or morpholinosulfonyl; alkylsulfinyl means, for example, methylsulfinyl, ethylsulfinyl, propylsulfinyl or butylsulfinyl; arylthio means, for example, phenylthio or naphthylthio; arylsulfinyl means, for example, phenylsulfinyl or naphthylsulfinyl; arylsulfonyl means, for example, phenylsulfonyl or naphthylsulfonyl; acylamino means, for example, acetylamino, propionylamino, butyrylamino or benzoylamino; alkoxycarbonyl means, for example, methoxycarbonyl, ethoxycarbonyl, propoxycarbonyl iospropoxycarbonyl, butoxycarbonyl or isobutoxycarbonyl; substituted carbamoyl means, for example, dimethylcarbamoyl, diethylcarbamoyl or piperidinocarbonyl; substituted amino means, for example, methylamino, dimethylamino, ethylamino, diethylamino, propylamino, dipropylamino, N-methyl-N-benzylamino or piperidino; straight alkylene means, for example, methylene, ethylene, trimethylene, tetramethylene, pentamethylene, hexamethylene, heptamethylene, octamethylene or decamethylene; branched alkylene means, for example, alkylene substituted by at least one, preferably 1 to 4 alkyl such as propylene, 1-methyltrimethylene, 3-methyltrimethylene, 1-methyltetramethylene, 4-methyltetramethylene, 1,4-dimethyltetramethylene, 6-methylhexamethylene or 4,4-dimethyltetramethylene.

In the formula (I), T is primary amino of —NH₂, secondary amino of —NHRa wherein Ra is alkyl (same as the above), cycloalkyl (e.g. cyclopropyl, cyclobutyl, cyclopentyl, cyclohexyl or cycloheptyl), arylalkyl (same as the above) or heteroarylalkyl (which may optionally be reduced, e.g. pyridylmethyl, furylmethyl thienylmethyl or (1,4-benzodioxan-2-yl)methyl), or tertiary amino of —N(Rb)(Rc) wherein Rb and Rc are the same or different and each is alkyl (same as the above), cycloalkyl (same as the above), arylalkyl (same as the above) or heteroarylalkyl (same as the above), and —N(Rb)(Rc) is exemplified by dialkylamino (e.g. dimethylamino, diethylamino, dipropylamino, diisopropylamino, dibutylamino, dihexylamino, dioctylamino), N-alkyl-N-cycloalkylamino (e.g. N-methyl-N-cyclopropylamino, N-methyl-N-cyclohexylamino, N-methyl-N-cyclopenylamino, N-ethyl-N-cyclopropylamino, N-ethyl-N-cyclopentylamino, N-ethyl-N-cyclohexylamino, N-propyl-N-cyclopropylamino, N-propyl-N-cyclohexylamino, N-butyl-N-cyclohexylamino), N-alkyl-N-arylalkylamino (e.g. N-methyl-N-benzylamino, N-methyl-N-(2-phenylethyl)amino, N- methyl-N-(3-phenylpropyl)amino, N-ethyl-N-benzylamino, N-ethyl-N-(2-phenylethyl)amino, N-propyl-N-benzylamino, N-propyl-N-(2-phenylethyl)amino, N-butyl-N-benzylamino, N-butyl-N-(2-phenylethyl)amino) or N-alkyl-N-heteroarylalkylamino (e.g. N-methyl-N-pyridylmethylamino, N-methyl-N-thienylmethylamino, N-methyl-N-furylmethylamino, N-ethyl-N-pyridylmethylamino, N-ethyl-N-thienylmethylamino, N-ethyl-N-furylmethyl-amino, N-methyl-N-(1,4-benzodioxan-2-ylmethyl)amino), or Rb and Rc together with the adjacent nitrogen atom form a cyclic amino of the formula:

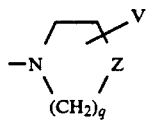

(1)

or

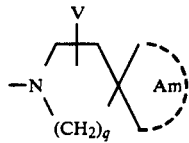

(2)

wherein q is an integer of 1 to 4, Z is methylene, oxygen atom, sulfur atom or N—R$^5$. Substituent V is hydrogen, hydroxyl, amino, carbamoyl, mono or di-substituted amino (e.g. methylamino, dimethylamino, ethylamino, diethylamino, anilino, N-acetylanilino, N-propionylanilino or pyrrolidinylanilino), cyclic amino (e.g. pyrrolidinyl, piperidino, hexamethyleneimino, morpholino, thiomorpholino, piperazinyl, homopiperazinyl, 4-substituted-piperazinyl or 4-substituted-homopiperazinyl), acyl (same as the above), aryl (e.g. phenyl, naphthyl), arylalkyl (same as the above), arylalkylamino (e.g. benzylamino, phenylethylamino, naphthylmethylamino or naphthylethylamino) alkyl (same as the above), alkoxy (same as the above), hydroxyalkyl (same as the above), alkoxycarbonyl (same as the above), heteroaryl (e.g. pyridyl, thienyl, furyl, pyrimidinyl, 1,2-benzoisothiazol-3-yl, 1,2-benzoisoxazol-3-yl, benzothiophen-3- or 4-yl, bezofuran-3- or 4-yl, quinolyl, isoquinolyl, benzoxazol-2-yl, pyrazinyl, piridazinyl, imidazolyl, thieno[3,2-c]pyridin-4-yl, furo[3,2-c]pyridin-4-yl, 2-oxo-1-benzimidazolyl, 2-thioxo-1-benzimidazolyl, 2,4-dioxohexahydropyrimidin-1-yl, hydantoin-1-yl), phenoxyalkyl (e.g. phenoxymethyl, 2-phenoxyethyl, 3-phenoxypropyl), anilinoalkyl (e.g. anilinomethyl, 2-anilinoethyl, 3-anilinopropyl), alkylaminoalkyl (e.g. N-methylaminomethyl, N,N-dimethylaminomethyl, N,N-diethylaminomethyl, 2-(N-methylamino)ethyl, 2-(N,N-dimethylamino)ethyl), alkanoylaminoalkyl (e.g. N-acetylaminomethyl, N-propionylaminomethyl, N-butyrylaminomethyl, 2-(N-acetylamino)ethyl) or bisarylmethylene (e.g. bis(4-fluorophenyl)methylene, bis(4-chlorophenyl)methylele) and the number of V is 1 to 4. R$^5$ of N—R$^5$ is hydrogen, alkyl (same as the above), cyanoalkyl (e.g. cyanomethyl, 2-cyanoethyl, 3-cyanopropyl, 4-cyanobutyl), hydroxyalkyl (same as the above), aryl (same as the above), arylalkyl (same as the above), alkoxycarbonyl (same as the above), diarylalkyl (e.g. diphenylmethyl, bis(4-fluorophenyl)methyl, 2,2-diphenylethyl, 2,2-bis(4-fluorophenyl)ethyl), heteroaryl (same as the above), heteroarylalkyl (same as the above), cycloalkyl (same as the above), cycloalkylalkyl (e.g. cyclopropylmethyl, cyclobutylmethyl, cyclohexylmethyl, cycloheptylmethyl), acyl (same as the above), cinnamyl or adamantanemethyl. Cyclic amino of formula (1) may contain carbonyl group in the cycle and further may be fused with acyl (e.g. benzene, naphthalele) or heteroaryl (e.g. furan, thiophene, pyridine, quinoline) to form fused cyclic amino such as 1,2,3,4-tetrahydroisoquinolin-2-yl or phthalimido. Ring Am of formula (2) contain amido bond in the cycle and further may contain oxygen atom, sulfur atom, carbonyl and/or N—R$^6$ (R$^6$ is hydrogen, alkyl or phenyl). The ring Am having amido bond in the cycle includes, for example, thiazolidinone, imidazolidinone, pyrazolidinone or pyrrolidinone. Further, the ring Am can be fused with 5 to 7 membered saturated or unsaturated ring to form, for example, 2-oxo-1,2,3,5,6,7,8,8a-octahydroimidazo[1,2-a]pyridine-3-spiro-4'-piperidino.

In the above definitions, each (hetero)aromatic ring and heterocyclic ring may optionally be substituted by 1 to 3 substituents (e.g. halogen, nitro, amino, cyano, haloalkyl, hydroxyl, alkyl, alkoxy or alkenyl).

The pharmaceutically acceptable acid addition salts of the compounds of formula (I) include salt such as hydrochloride, hydrobromide, phosphate, sulfate, p-toluenesulfonate, benzenesulfonate, methanesulfonate, citrate, lactate, maleate, fumarate, tartrate or oxalate. The present invention also includes hydrate and solvate of the compounds of formula (I).

The compounds of formula (I) or (II-e) having a chiral carbon atom can be prepared as a racemate or an optically active isomer, and the compound having at least two chiral atoms can be obtained as an individual diastereomer or a mixture thereof. The present invention embraces the mixture thereof and the individual isomers. Furthermore, the present invention embraces stereomers, too.

Preferred compounds of the present invention are those of formula (I) wherein T is —NHRa where Ra is heteroarylalkyl which may be optionally substituted by 1 to 3 substituents, or —N(Rb)(Rc) where Rb and Rc are the same or different and each is alkyl, arylalkyl or heteroarylalkyl, or Rb and Rc together with the adjacent nitrogen atom form a cyclic amino of the formula:

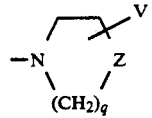

(1)

or

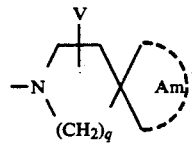

(2)

wherein q is an integer of 1 to 4, Z is methylene or N—R$^5$ (R$^5$ is aryl, diarylalkyl, heteroaryl, heteroarylalkyl or acyl), substituent V is hydrogen, hydroxyl, carbamoyl, cyclic amino, aryl, arylalkylamino, heteroaryl or bisarylmethylene and the number of V is 1 to 4. Cyclic amino of formula (1) may contain carbonyl group in the cycle and further may be fused with aryl or heteroaryl. Ring Am of formula (2) contains amido bond in the cycle and further may contain sulfur atom and/or N—R⁶ (R⁶ is phenyl). Further, the ring Am can be fused with 5 to 7 membered saturated or unsaturated ring. In the above definitions, (hetero)aromatic ring and heterocyclic ring may optionally be substituted by 1 to 3 substituents.

A preferable definition of T is a cyclic amino of the formula:

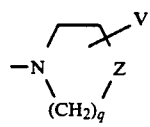

where Z is N—R⁵ (R⁵ is spyrimidinyl or substituted pyrimidinyl), substituent V is hydrogen, and q is 2, that is, the formula (1) is represented by the formula:

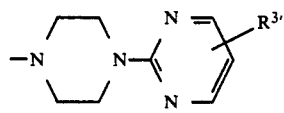

wherein R³' is hydrogen, halogen, nitro, amino, cyano, hyroxyl, alkyl, alkoxy or haloalkyl.

Preferable definitions of E¹, E² and E³ are that E¹ is C—R¹, E² is C—R² and E³ is sulfur atom, wherein R¹ and R² are as defined above, preferably they are the same or different and each is hydrogen, halogen, nitro, amino, cyano, hydroxyl, formyl, alkyl, alkoxy, haloalkyl, arylalkyl, acyl, alkoxyalkyl, acyloxyalkyl hydroxyalkyl, acyloxyalkanoyl, alkoxyalkanoyl, hydroxyalkanoyl, aryloxyalkanoyl or haloalkanoy.

Preferable definitions of A, B and n are that A and B are carbonyl and n is 1 or 2, or one of A and B is absent and the other is carbonyl and n is 2 or 3, and more preferably one of A and B is absent and the other is carbonyl and n is 2.

Preferable definition of Q is straight or branched chain alkylene having 1 to 10 carbon atoms, and more preferably Q is alkylene having 1 to 8 carbon atoms.

More preferable definition of D is —CH₂—.

This invention also provides a compound of the formula:

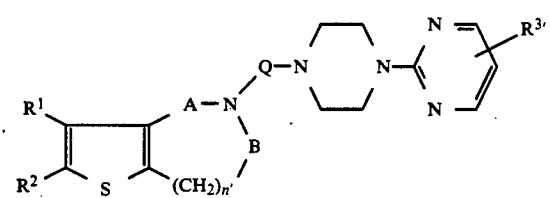

or pharmaceutically acceptable acid addition salt thereof, wherein R¹ and R² are the same or different and each is hydrogen, halogen, nitro, amino, cyano, hydroxyl, formyl, alkyl, alkoxy, haloalkyl, aralkyl, acyl, alkoxyalkyl, acyloxyalkyl hydroxyalkyl, acyloxyalkanoyl alkoxyalkanoyl, hydroxyalkanoyl, aryloxyalkanoyl or haloalkanoyl, R³' is as defined in claim 6, A and B are carbonyl groups, or one of A and B is absent and the other is carbonyl group, n' is 2 or 3 when A and B are carbonyl groups and n' is 3 or 4 in the other case, Q is straight or branched chain alkylene having 1 to 10 carbon atoms.

This invention further provides a compound of the formula:

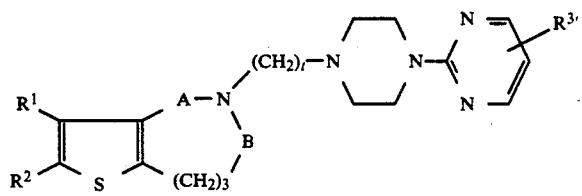

or pharmaceutically acceptable acid addition salt thereof, wherein R¹ and R² are as defined above, R³' is as defined above, t is an integer of 1 to 8, A and B are absent or carbonyl groups with the provisos that when A is absent, B is carbonyl group, and when A is carbonyl group, B is absent.

This invention further more provides a compound of the formula (I) or pharmaceutically acceptable acid addition salt thereof, wherein T is a group of the formula:

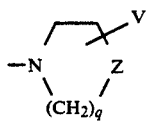

wherein Z is methylene or N—R⁵ (R⁵ is aryl, diarylalkyl, heteroaryl except pyrimidinyl, heroarylalkyl or acyl), substituent V is hydrogen, hydroxyl, carbamoyl, cyclic amino, aryl, arylalkylamino, heteroaryl or bisarylmethylene and the number of V is 1 to 4, q is 2, and in the above definition the (hetero)aromatic ring and heterocyclic ring may optionally be substituted by 1 to 3 substituents.

Preferred compounds of the formula (I) are
2-bromo-5-[-4-(4-(2-pyrimidinyl)-1-piperazinyl)butyl]-5,6,7,8-tetrahydro-4H-thieno[3,2-c]azepin-4-one,
2-methyl-5-[4-(4-(2-pyrimidinyl)-1-piperazinyl)butyl]-5,6,7,8-tetrahydro-4H-thieno[3,2-c]azepin-4-one,
2-ethyl-5-[4-(4-(2-pyrimidinyl)-1-piperazinyl)butyl]-5,6,7,8-tetrahydro-4H-thieno[3,2-c]azepin-4-one,
2-acetyl-5-[4-(4-(2-pyrimidinyl)-1-piperazinyl)butyl]-5,6,7,8-tetrahydro-4H-thieno[3,2-c]azepin-4-one,
2-(1-hydroxyethyl)-5-[4-(4-(2-pyrimidinyl)-1-piperazinyl)butyl]-5,6,7,8-tetrahydro-4H-thieno[3,2-c]azepin-4-one,
5-[4-(4-(1,2-benzisothiazol-3-yl)-1-piperazinyl)butyl]-2-methy-5,6,7,8-tetrahydro-4H-thieno[3,2-c]azepin-4-one,
5-[4-[(1,4-benzodioxan-2-yl)methylamino]butyl]-2-methy-5,6,7,8-tetrahydro-4H-thieno[3,2-c]azepin-4-one,
2,3-dihydro-4-[4-(4-(2-pyrimidinyl)-1-piperazinyl)butyl]thieno[3,2-f]-1,4-thiazepin-5(4H)-one,
7-bromo-2,3-dihydro-4-[4-(4-(2-pyrimidinyl)-1-piperazinyl)butyl]-thieno[3,2-f]-1,4-thiazepin-5(4H)-one, 7-acetyl-2,3-dihydro-4-[4-(4-(2-pyrimidinyl)-1-piperazinyl)butyl]-thieno[3,2-f]-1,4-thiazepin-5(4H)-one, 7-ethyl-2,3-dihydro-4-[4-(4-(2-pyrimidinyl)-1-piperazinyl)butyl]-thieno[3,2-f]-1,4-thiazepin-5(4H)-one, 4-[4-(4-(1,2-benzisothiazol-3-yl)-1-piperazinyl)butyl]-2,3-dihydrothieno[3,2-f]-1,4-thiazepin-5(4H)-one, 5-[4-(4-(bis(4-fluorophenyl)methyl)-1-piperazinyl)butyl]-2-methy-5,6,7,8-tetrahydro-4H-thieno[3,2-c]azepin-4-one, 2-methyl-5-[4-(4-(2-pyrimidinyl)-1-piperazinyl)butyl]-5,6,7,8-tetrahydro-4H-thieno[3,2-c]azepine-4,6-dione, 7-methyl-4-[4-(4-(2-pyrimidinyl)-1-piperazinyl)butyl]-2,3-dihydro-4H-thieno[3,2-f][1,4]thiazepine-3,5-dione, 5-[4-(4-(3-trifluoromethylphenyl)-1-piperazinyl)butyl]-5,6,7,8-tetrahydro-4H-thieno[3,2-c]azepin-4-one, 5-[4-(4-(2,3-dimethylphenyl)-1-piperazinyl)butyl]-2-5,6,7,8-tetrahydro-4H-thieno[3,2-c]azepin-4-one, 5-[4-(4-(2-methoxyphenyl)-1-piperazinyl)butyl]-2-5,6,7,8-tetrahydro-4H-thieno[3,2-c]azepin-4-one, 2,3-dihydro-4-[4-(4-(2-methoxyphenyl)-1-piperazinyl)-butyl]-7-methylthieno[3,2-f]-1,4-thiazepin-5(4H)-one and 4[4-(4-(bis(4-fluorophenyl)methylene)piperidino)butyl]-2,3-dihydro-7-methylthieno[3,2-f]-1,4-thiazepin-5(4H)-one or pharmaceutically acceptable acid addition salt thereof.

More preferred compounds of the formula (I) are 2-bromo-5-[4-(4-(2-pyrimidinyl)-1-piperazinyl)butyl]-5,6,7,8-tetrahydro-4H-thieno[3,2-]azepin-4-one, 2-methyl-5-[4-(4-(2-pyrimidinyl)-1-piperazinyl)butyl]-5,6,7,8-tetrahydro-4H-thieno[3,2-c]azepin-4-one, 2-ethyl-5-[4-(4-(2-pyrimidinyl)-1-piperazinyl)butyl]-5,6,7,8-tetrahydro-4H-thieno[3,2-c]azepin-4-one, 2-acetyl-5-[4-(4-(2-pyrimidinyl)-1-piperazinyl)butyl]-5,6,7,8-tetrahydro-4H-thieno[3,2-c]azepin-4-one, 2-(1-hydroxyethyl)-5-[4-(4-(2-pyrimidinyl)-1-piperazinyl)butyl]-5,6,7,8-tetrahydro-4H-thieno[3,2-c]azepin-4-one, 2,3-dihydro-4-[4-(4-(2-pyrimidinyl)-1-piperazinyl)-butyl]thieno[3,2-f]-1,4-thiazepin-5(4H)-one, 7-bromo-2,3-dihydro-4-[4-(4-(2-pyrimidinyl)-1-piperazinyl)butyl]-thieno[3,2-f]-1,4-thiazepin-5(4H)-one, 7-acetyl-2,3-dihydro-4-[4-(4-(2-pyrimidinyl)-1-piperazinyl)butyl]-thieno[3,2-f]-1,4-thiazepin-5(4H)-one, 7-ethyl-2,3-dihydro-4-[4-(4-(2-pyrimidinyl)-1-piperazinyl)butyl]-thieno[3,2-f]-1,4-thiazepin-5(4H)-one, 2-methyl-5-[4-(4-(2-pyrimidinyl)-1-piperazinyl)butyl]-5,6,7,8-tetrahydro-4H-thieno[3,2-c]azepine-4,6-dione and 7-methyl-4-[4-(4-(2-pyrimidinyl)-1-piperazinyl)butyl]-2,3-dihydro-4H-thieno[3,2-f][1,4]thiazepine-3,5-dione or pharmaceutically acceptable acid addition salt thereof.

Preferred intermediates of the present invention are those of formulas (II) and (IV) wherein $E^1$ is C—$F^1$, $E^2$ is C—$R^2$ and $E^3$ is sulfur atom, that is, represented by the formulas:

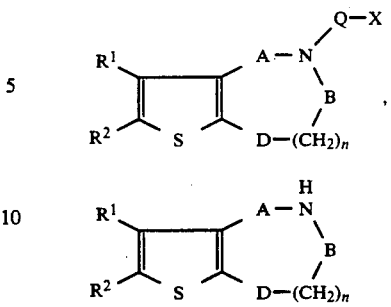

wherein each symbol is as defined above.

The present invention provides a pharmaceutical composition consisting of a fused thiophene compound of the formula (I) or pharmaceutically acceptable acid addition salt thereof and pharmaceutical carriers, especially antianxiety drug, antipsychotic drug or drug for the disease of circulatory system.

The methods for preparing the compounds of present invention are described as follows:

METHOD (1)

The compounds of formula (I) can be synthesized by reacting the compound of formula (II-a) with a compound of formula:

$$H—T \quad \quad (III)$$

wherein T is as defined above, or acid addition salt thereof.

The reaction is carried out in an inert solvent such as methanol, ethanol, propanol, benzene, toluene, dimethylformamide, tetrahydrofuran, acetonitrile or acetone in the presence of a suitable acid scavenger (e.g. potassium carbonate, sodium carbonate, sodium hydrogencarbonate, pyridine, triethylamine, sodium acetate or potassium acetate) at 20°–150° C. for 30 minutes to 30 hours.

When X in the compounds of formula (II-a) is hydroxyl, the reaction is carried out in a suitable inert solvent such as dimethylformamide or benzene in the presence of an aminophosphonium reagent (N,N-methylphenylaminotriphenylphosphonium iodide) at 20° C.–150° C. for 30 minutes to 5 hours.

METHOD (2)

The compounds of formula (I) can be synthesized by reacting the compound of formula (IV) with a compound of the formula:

$$X—Q—T \quad \quad (V)$$

wherein each symbol is as defined above, or an acid addition salt thereof.

The reaction is carried out under the same conditions as the method (1).

METHOD (3)

The compounds of formula (I) can be prepared by reductive amination of the compound of formula (II-b) with a compound of formula (III).

The reaction is carried out in an alcohol solvent such as methanol, ethanol or propanol in the presence of a suitable reductant (e.g. sodium borohydride, sodium cyanoborohydride) at 0° C. to the boiling point of the solvent employed for 1 to 24 hours.

In the compounds of formula (I), for example, the compounds of formula:

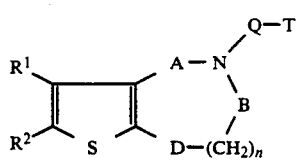 (I')

wherein $R^2$ is acyl or a group derived from acyl and other symbols are as defined above, can be synthesized by the following methods.

METHOD (4)

The compounds of formula (I') wherein $R^2$ is acyl can be synthesized by reacting a compound of the formula:

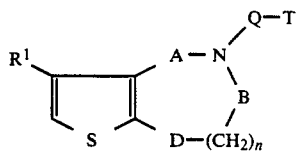 (VI)

wherein each symbol is as defined above, with a compound of the formula:

 (VII)

wherein $R^4$ is alkyl, aryl, haloalkyl, pyridyl, thienyl or furyl.

The reaction is carried out in a suitable inert solvent such as benzene or toluene or without solvent in the presence of a dehydrating agent (e.g. polyphosphoric acid, phosphorus pentoxide) at 10° C.–150° C.

METHOD (5)

The compound of formula (I') wherein $R^2$ is acyl can be synthesized by reacting the compound of formula (VI) with a compound of the formula:

$R^4COZ$ (VIII)

wherein Z is halogen and $R^4$ is as defined above.

The reaction is carried out in a suitable inert solvent such as benzene, toluene, chloroform, dichloromethane or dichloroethane in the presence of a suitable Lewis acid (e.g. tin chloride, iron chloride, aluminum chloride, zinc chloride) at −10° C. to 100° C. for 30 minutes to 5 hours.

METHOD (6)

The compounds of formula (I') wherein $R^2$ is alkyl aralkyl or 1-hydroxyalkyl can be synthesized by reducing a compound of the formula:

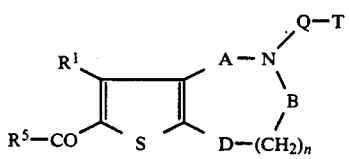 (IX)

wherein $R^5$ is alkyl, aralkyl or aryl and other symbols are as defined above, with a reductant such as sodium borohydride, lithium aluminum hydride or triethylsilane, or by subjecting the compound to catalytic reduction in the presence of a suitable catalyst (e.g. platinum dioxide, palladium, rhodium).

The reaction is carried out in a suitable solvent (e.g. methanol, ethanol, propanol, butanol, acetic acid) at −10° C. to 150° C. to give a compound of the formula:

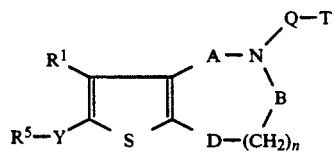 (X)

wherein Y is —CH(OH)— or —CH$_2$— and other symbols are as defined above.

METHOD (7)

The compounds of formula (I') wherein $R^2$ is acyloxyalkanoyl can be synthesized by reacting a compound of the formula:

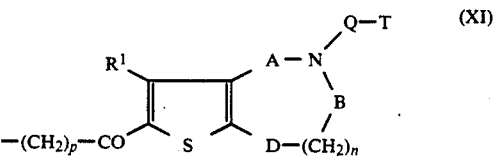 (XI)

wherein p is a integer of 1 to 4 and other symbols are as defined above, with a metal (e.g. sodium, potassium, lithium) salt of a compound of the formula (VII).

The reaction is carried out in a suitable inert solvent such as chloroform, methylene chloride, benzene, toluene or dimethylformamide at room temperature to 150° C. for 1 to 20 hours to give a compound of the formula:

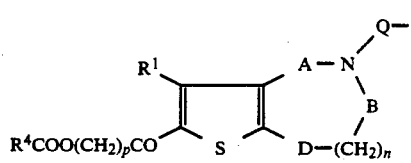 (XII)

wherein each symbol is as defined above.

METHOD (8)

The compounds of formula (I') wherein $R^2$ is alkoxyalkanoyl or aryloxyalkanoyl can be synthesized by reacting the compound of formula (XI) with a metal (e.g. sodium, potassium, lithium) salt of a compound of the formula:

$R^6OH$ (XIII)

wherein $R^6$ is alkyl or aryl.

The reaction is carried out in a suitable inert solvent such as tetrahydrofuran, benzene, toluene or dimethylformamide at room temperature to 150° C. for 1 to 20 hours to give a compound of the formula:

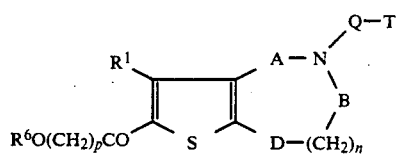

wherein each symbol is as defined above.

METHOD (9)

The compounds of formula (I') wherein $R^2$ is hydroxyalkanoyloxy can be synthesized by hydrolysis of the compound of formula (XII).

The reaction is carried out in a suitable inert solvent such as methanol, ethanol, propanol, butanol or water in the presence of an aqueous solution of an acid (e.g. hydrochloric acid, sulfuric acid, phosphoric acid, nitric acid) or an alkali (e.g. sodium hydroxide, potassium hydroxide, lithium hydroxide, barium hydroxide, potassium carbonate) at $-10°$ C. to 150° C. for 1 to 20 hours to give a compound of the formula:

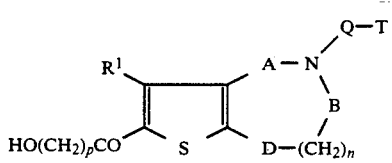

wherein each symbol is as defined above.

METHOD (10)

The compounds of formula (I') wherein $R^2$ is acyloxyalkyl or alkoxyalkyl can be synthesized by reacting a compound of the formula:

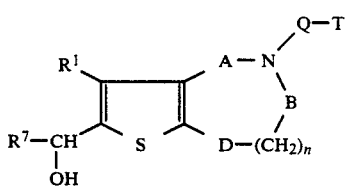

wherein $R^7$ is alkyl and other symbols are as defined above, which is obtained in method (6) with a compound of the formula:

$R^8Z$       (XVII)

wherein $R^8$ is acyl or alkyl and Z is as defined above.

The reaction is carried out in a suitable inert solvent such as methanol, ethanol, propanol, butanol, dimethylformamide, tetrahydrofuran, benzene or toluene in the presence of an acid scavenger (e.g. sodium hydride, sodium amide, sodium methoxide, sodium ethoxide, potassium hydroxide, sodium hydroxide) at room temperature to 150° C. for 1 to 20 hours to give a compound of the formula:

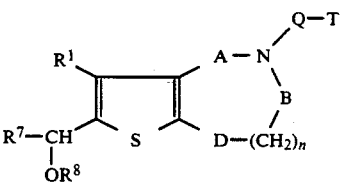

wherein each symbol is as defined above.

METHOD (11)

The compounds of formula (I') wherein $R^2$ is hydroxysulfonyl or halosulfonyl can be synthesized by reacting the compound of formula (VI) with sulfuric acid or halosulfonic acid.

The reaction is carried out in a suitable inert solvent such as benzene or toluene or without solvent at $-10°$ C. to 100° C. to give the compound of formula:

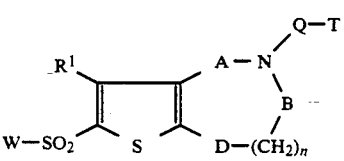

wherein W is hydroxyl or halogen and other symbols are as defined above.

METHOD (12)

The compounds of formula (I') wherein $R^2$ is sulfamoyl or substituted-sulfamoyl can be synthesized by reacting the compound of formula (XIX) with the compound of formula:

$HN(R^{10})(R^{11})$       (XX)

wherein $R^{10}$ and $R^{11}$ are the same or different and each is hydrogen, alkyl, arylalkyl or aryl.

The reaction is carried out in a suitable inert solvent such as benzene, toluene, dimethylformamide or tetrahydrofuran, preferably in the presence of an acid scavenger (e.g. sodium hydride, sodium amide, sodium methoxide, sodium ethoxide, potassium hydroxide, sodium hydroxide) at $-10°$ C. to 150° C. for 1 to 20 hours to give the compound of formula:

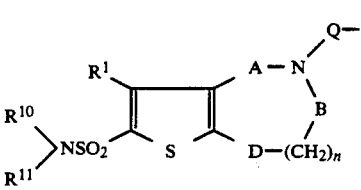

wherein each symbol is as defined above.

The above-mentioned methods of (4) to (12) are also applicable to the syntheses of compounds of formula (I) (wherein $E^1=C-R^1$, $E^2=$sulfur atom, $E^3=C-R^2$; or $E^1=$sulfur atom, $E^2=C-R^1$, $E^3=C-R^2$) other than formula (I').

METHOD (13)

The compounds of formula (I) wherein T is amino group ($-NH_2$) can be synthesized by reacting a compound of the formula:

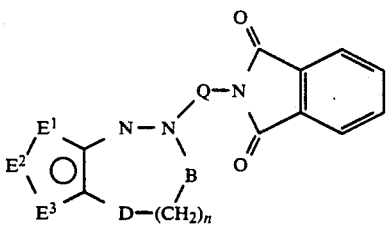 (I-a)

wherein each symbol is as defined above, which can be obtained by the above method, in an inert solvent (e.g. methanol) in the presence of hydrazine hydrate at 20° C. to 150° C. for 1 to 20 hours.

METHOD (14)

The compounds of formula (I) wherein T is amino group (—NH$_2$) can be synthesized by reacting the compound of formula (II-c) or (II-e) in an inert solvent (e.g. lower alcohol such as methanol, ethanol or propanol, water, acetic acid, tetrahydrofuran, dioxane) in the presence of a nickel catalyst such as Raney nickel at 0° C. to the boiling point of the solvent employed for 1 to 24 hours.

METHOD (15)

The compounds of formula (I) wherein T is amino group (—NH$_2$) can by synthesized by reacting the compound of formula (II-d) in an inert solvent (e.g. water) in the presence of bromine and sodium hydroxide or potassium hydroxide at 0° C. to 100° C. for 1 to 24 hours.

The compounds of formula (II-a) which are synthetic intermediates are novel compounds and can be prepared by the following method.

METHOD (16)

The compounds of formula (II-a) can be synthesized by reacting the compound of formula (IV) with a compound of the formula:

X$^1$—Q—X$^2$ (XXII)

wherein X$^1$ and X$^2$ are hydroxyl or reactive atom or group derived from hydroxyl (e.g. halogen, methanesulfonyloxy, paratoluenesulfonyloxy) with the proviso that both X$^1$ and X$^2$ are not hydroxyl at the same time and Q is as defined above.

The reaction is carried out in a suitable inert solvent such as methanol, ethanol, propanol, dimethylformamide, benzene, toluene, tetrahydrofuran or acetonitrile in the presence of a suitable base (e.g. sodium methoxide, sodium ethoxide, potassium t-butoxide, sodium hydride, potassium hydride, sodium hydroxide, potassium hydroxide, potassium carbonate, sodium carbonate) at —20° C. to 150° C. for 30 minutes to 5 hours.

The compounds of formula (II-b) which are synthetic intermediates are also novel compounds and can be prepared by the following method.

METHOD (17)

The compounds of formula (II-b) can be synthesized by reacting the compound of formula (IV) with a compound of the formula:

X$^3$—Q—COR$^4$ (XXIII)

wherein X$^3$ is a removable group such as chlorine, bromine, iodine, methanesulfonyloxy or paratoluenesulfonyloxy and other symbols are as defined above, or preferably by protecting the carbonyl group of the compound (XXIII) in a conventional manner of organic chemistry, reacting with the compound of formula (IV) and then eliminating the protecting group to give the objective compound in good yield.

The reaction is carried out in a suitable inert solvent such as dimethylformamide, methanol, ethanol, propanol, butanol, tetrahydrofuran, benzene, toluene or acetonitrile in the presence of a suitable base (e.g. sodium methoxide, sodium ethoxide, potassium t-butoxide, sodium hydride, potassium hydride, sodium hydroxide, potassium hydroxide, potassium carbonate, sodium carbonate) at —20° C. to 150° C. for 30 minutes to 5 hours.

The synthetic intermediate compounds of formula (II-a) wherein R$^2$ is acyl, alkyl, aralkyl, 1-hydroxyalkyl, acyloxyalkanoyl, alkoxyalkanoyl, aryloxyalkanoyl, hydroxyalkanoyl, acyloxyalkanoyl, alkoxyalkyl, hydroxysulfonyl, halosulfonyl, aminosulfonyl or substituted-amino-sulfonyl can be prepared by applying the above-mentioned methods (4) to (12) to the compound of formula (II-a). The methods (4) to (12) can also be applied to the synthetic intermediate compounds of formula (II-b).

The compounds of formulas (II-c), (II-d) and (II-e) which are synthetic intermediates are novel compounds and can be prepared by the following methods.

METHOD (18)

The compounds of formula (II-c) can be synthesized by reacting the compound of formula (IV) with a compound of the formula:

X$^3$—Q—CN (XXIV)

wherein each symbol is as defined above.

The reaction is carried out in a suitable inert solvent such as dimethylformamide, methanol, ethanol, propanol, tetrahydrofuran, benzene, toluene or acetonitrile in the presence of a suitable base (e.g. sodium methoxide, sodium ethoxide, sodium hydride, potassium hydride, sodium hydroxide, potassium hydroxide, sodium carbonate, potassium carbonate) at —20° C. to 150° C. for 30 minutes to 5 hours.

METHOD (19)

The compounds of formula (II-d) can be synthesized by reacting the compound of formula (IV) with a compound of the formula:

X$^3$—Q—CONH$_2$ (XXV)

wherein each symbol is as defined above.

The reaction is carried out under the same condition as in the method (18).

METHOD (20)

The compounds of formula (II-e) can be synthesized by reacting the compound of formula (IV) with a compound of the formula:

X$^3$—Q—NO$_2$ (XXVI)

wherein each symbol is as defined above.

The reaction is carried out under the same condition as in the method (18).

METHOD (21)

The compounds of formula (I) wherein both A and B are carbonyl groups can, for example, be synthesized by subjecting a compound of the formula:

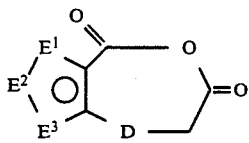   (XXVII)

wherein each symbol is as defined above, with a compound of the formula:

H$_2$N—Q—T   (XXVIII)

wherein each symbol is as defined above, to dehydrating reaction.

The reaction is carried out in a suitable inert solvent (e.g. acetic anhydride, toluene, benzene, chloroform, methylene chloride, pyridine, methanol, ethanol, isopropyl alcohol, dimethylformamide, tetrahydrofuran) or without a solvent at 20° C. to the boiling point of the solvent employed for 30 minutes to 10 hours.

METHOD (22)

The compounds of formula (XXVII) are novel and can be synthesized by reacting, for example, a compound of the formula:

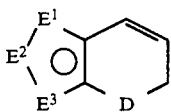   (XXIX)

wherein each symbol is as defined above, with ozone and then subjecting a resulting compound of the formula:

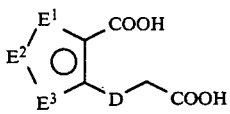   (XXX)

wherein each symbol is as defined above, obtained by the oxidative treatment to ring closure reaction with a dehydrating agent (e.g. phosphorus pentoxide, dicyclohexylcarbodiimide, N,N-carbonyldiimidazole, acid anhydride, acid halide, benzenesulfonyl chloride).

The reaction of the compound of formula (XXIX) with ozone is carried out in a suitable inert solvent such as methanol, ethanol, propanol or tetrahydrofuran at −20° C. to 150° C. for 30 minutes to 10 hours.

The reaction of the compound of formula (XXX) with a dehydrating agent is carried out in a suitable inert solvent (e.g. ether, dichloromethane, tetrahydrofuran) or without a solvent at 10° C. to 150° C. for 30 minutes to 10 hours.

METHOD (23)

The compounds of formula (XXVII) can also be synthesized by introducing formyl group into, for example, a compound of the formula:

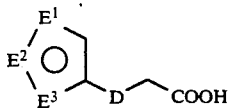   (XXXI)

wherein each symbol is as defined above, by Vilsmeier reaction or the like and oxidating the formyl group of a compound of the formula:

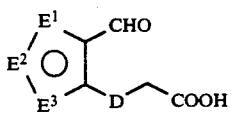   (XXXII)

wherein each symbol is as defined above, by a conventional method employed in organic chemistry and then treating the resulting compound of formula (XXX) in the same manner as the above method (23).

The compounds of formula (IV) wherein D is S(O)$_m$ and A is absent, B is carbonyl or A is carbonyl, B is absent are also novel and can be synthesized by, for example, the following method (24) or (25).

METHOD (24)

A method which comprises subjecting a compound of the formula:

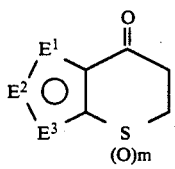   (XXXIII)

wherein each symbol is as defined above, to Schmidt rearrangement.

The reaction is carried out by reacting with sodium azide in a suitable inert solvent such as chloroform, methylene chloride, toluene or benzene or without a solvent in the presence of a suitable acid (e.g. trifluoroacetic acid, polyphosphoric acid, sulfuric acid) at 0° C. to 150° C. for 30 minutes to 10 hours.

METHOD (25)

A method which comprises subjecting a compound of the formula:

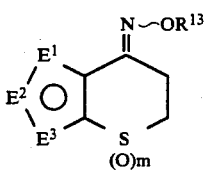   (XXXIV)

wherein R$^{13}$ is hydrogen, alkyl, methanesulfonyl group or paratoluenesulfonyl group and other symbols are as defined above, to Beckmann rearrangement.

The reaction is carried out in a suitable inert solvent such as benzene, toluene, dimethylformamide or diethyl ether or without a solvent in the presence of a suitable acid (e.g. polyphosphoric acid, sulfuric acid, phosphoric acid, phosphorus oxychloride, phosphorus pentachloride, phosphorus pentoxide) at 0° C. to 150° C. for 30 minutes to 10 hours.

METHOD (26)

The compounds of formula (I-a) which are used in method (13) can be synthesized by reacting the compound of formula (IV) with a compound of the formula:

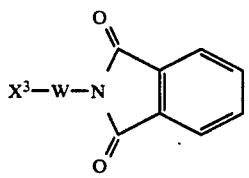

(XXXV)

wherein each symbol is as defined above.

The reaction is carried out under the same condition as method (18).

METHOD (27)

The compounds of formula (I) wherein A and/or B are(is) thiocarbonyl group can be synthesized by reacting the compound of formula (I) wherein A and/or B are(is) carbonyl group with a thionating agent. The thionating agent includes phosphorus pentasulfide, Lawesson reagent [2,4-bis(4-methoxyphenyl)-1,3,2,4-dithiadiphosphetan-2,4-disulfide] and so on. The reaction is usually carried out in an inert solvent (e.g. pyridine, dimethylaniline, benzene, toluene, xylene, tetrahydrofuran, chloroform, dioxane or a mixed solvent thereof) at 30° C. to 100° C.

METHOD (28)

The compounds of formula (I) wherein $R^1$ and/or $R^2$ are(is) acylamino can be synthesized by a well known acylation of the compounds wherein $R^1$ and/or $R^2$ are(is) amino, or by first reacting the compounds of formula (I) wherein $R^1$ and/or $R^2$ are(is) acyl with a hydroxylamine and then subjecting the obtained oxime compounds to a Beckmann rearrangement, or by subjecting the compounds of formula (I) wherein $R^1$ and/or $R^2$ are(is) acyl to a Schmidt rearrangement.

The method for synthesizing the oxime compounds is carried out by reacting the compounds of formula (I) wherein $R^1$ and/or $R^2$ are(is) acyl with a hydroxylamine hydrochloride in a suitable inert solvent (e.g. benzene, toluene, chloroform, methylene chloride, dimethylformamide, tetrahydrofuran, methanol, ethanol) in the presence of a base (e.g. potassium carbonate, sodium hydrogencarbonate, sodium hydroxide, potassium hydroxide, triethylamine) at room temperature to refluxing temperature of the solvent employed.

The Beckmann rearrangement is carried out by reacting the above oxime compounds in a polyphosphoric acid at 60° C. to 120° C.

The Schmidt rearrangement is carried out by reacting the compounds of formula (I) wherein $R^1$ and/or $R^2$ are(is) acyl with sodium azide in polyphosphoric acid or sulfuric acid at 0° C. to 100° C.

METHOD (29)

The compounds of formula (I) can be synthesized by reacting a compound of the formula:

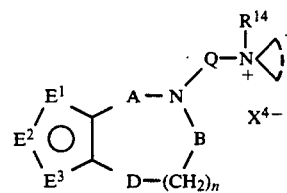

(XXXVI)

wherein $R^{14}$ is alkyl and $X^4$ is halogen, and other symbols are as defined above, with the compound of formula (III).

The reaction is carried out in a suitable inert solvent such as methanol, ethanol, benzene, toluene, dimethylformamide or 1,3-dimethyl-2-imidazolidinone at 50° C. for 1 to 10 hours.

METHOD (30)

The compounds of formula (XXXVI) can be synthesized by reacting the compound of formula (I) wherein T is tertiary amino group with a compound of the formula:

$$R^{14}X^4 \quad (XXXVII)$$

wherein each symbol is as defined above.

The reaction is carried out in a suitable inert solvent (e.g. benzene, toluene, acetone, chloroform, methylene chloride, dimethylformamide, tetrahydrofuran, methanol, ethanol, acetonitrile) at −20° C. to refluxing temperature of the solvent employed for 10 minutes to 5 hours.

METHOD (31)

The compound of formula (I) wherein T is —NH$_2$ is reacted with a compound of the formula:

$$R^{15}X^3 \quad (XXXVIII)$$

wherein $R^{15}$ is alky or arylalkyl and $X^3$ is as defined above, to give a compound of the formula (I) wherein T is —NHR$^{15}$ or —N(R$^{15}$) ($R^{15}$ is as defined above).

The reaction is carried out in a suitable inert solvent (e.g. methanol, ethanol, propanol, dimethylformamide, tetrahydrofuran, benzene or toluene) in the presence of a suitable acid scavenger (e.g. triethylamine, sodium hydrogencarbonate, potassium hydrogencarbonate, sodium carbonate, potassium carbonate, sodium hydroxide or potassium hydroxide) at 0° C. to the boiling point of the solvent employed.

Further, the compound of formula (I) wherein T is —NHR$^{15}$ is reacted with a compound of the formula:

$$R^{16}X^3 \quad (XXXIX)$$

wherein $R^{16}$ is alkyl or arylalkyl and $X^3$ is as defined above, to give a compound of the formula (I) wherein T is —N(R$^{15}$) (R$^{16}$) ($R^{15}$ and $R^{16}$ are as defined above).

The reaction is carried out under the same condition as the above.

METHOD (32)

The compound of formula (I) wherein T is —NH$_2$ is reacted with a compound of the formula:

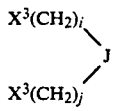

(XXXX)

wherein i and j are integer of 1 to 3 respectively, J is oxygen atom, sulfur atom, CH—$R^{17}$ or N—$R^{17}$ ($R^{17}$ is hydrogen, alkyl, arylalkyl or heteroaryl) and $X^3$ is as defined above, to give a compound of the formula (I) represented by:

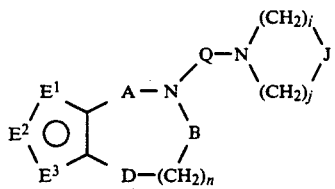

wherein each symbol is as defined above.

The reaction is carried out in a suitable inert solvent (e.g. methanol, ethanol, propanol, dimethylformamide, tetrahydrofuran, benzene or toluene) in the presence of a suitable acid scavenger (e.g. triethylamine, sodium hydrogencarbonate, potassium hydrogencarbonate, sodium carbonate, potassium carbonate, sodium hydroxide or potassium hydroxide) at 0° C. to the boiling point of the solvent employed.

The thus obtained compounds of presence invention can be isolated and purified by a conventional method such as recrystallization or column chromatography.

When the obtained compound is a racemate, it can be separated into desired optically active isomers, for example, by means of fractional recrystallization of a salt with an optically active acid or through column filled with an optically active carrier. Individual diastereomers can be separated by the method such as fractional crystallization or chromatography. Such compounds can also be obtained by using an optically active starting material. Furthermore, the stereoisomers can be isolated by recrystallization, column chromatography or the like.

The following experiments will illustrate potent pharmacological activities of the compounds of formula (I).

EXPERIMENT 1

Affinity for serotonin 1A (5-$HT_{1A}$) receptor
[$^3$H-8-Hydroxy-2-dipropylaminotetralin
($^3$H-8-OH-DPAT) binding test]

Preparation of crude synaptosome fraction and binding assay were conducted in accordance with the method reported in Journal of Neurochemistry, vol. 44, page 1685, 1985 by Hall et al. Freezed hippocampus dissected out from rats were homogenized in 40 volumes of ice-cold 50 mM Tris-HCl buffer (pH 7.4) and the suspension was centrifuged at 500×g for 10 minutes at 0° C. The supernatant was centrifuged at 40,000×g for 20 minutes at 0° C. and the resulting pellet was homogenized in 40 volumes of the above buffer and incubated at 37° C. for 10 minutes. After completion of reaction, the suspension was centrifuged at 40,000×g for 20 minutes at 0° C. The resulting pellet was washed twice by resuspension in 40 volumes of the above buffer and centrifugation, and finally suspended in 60 volumes of ice-cold 50 mM Tris-HCl buffer (pH 7.4) containing 1 mM manganese chloride for use in the next assay.

To the aliquots (900 μl) of synaptosome membranes solution were added 50 μl of tritiated 8-OH-DPAT solution at the terminal concentration of 0.2 nM and 50 μl of test compound solution or 50 μl of its medium, and incubated at 37° C. for 10 minutes. Then, to the mixture was added 5 ml of ice-cold 50 mM Tris-HCl buffer (pH 7.4), rapidly vacuum-filtered through Whatman GF/B filters and washed twice with 5 ml of the same buffer. The radioactivity of the residue remaining on the filters was measured by liquid scintillation counter. Nonspecific binding was determined under the presence of $10^{-5}$ M serotonin (5-HT). 50% Inhibition concentration ($IC_{50}$) of the test compound was graphically determined and the inhibition constant (Ki value) was calculated. The results are summarized in Table A.

EXPERIMENT 2

Affinity for serotonin 2 (5-$HT_2$) receptor
($^3$H-Ketanserin binding test)

Preparation of crude synaptosome fraction and binding assay were conducted according to the method reported in Molecular Pharmacology, vol. 21, page 301, 1981 by Leysen et al.

Freezed cerebral cortex dissected out from rats were homogenized in 30 volumes of ice-cold 0.32 M sucrose solution and the suspension was centrifuged at 1000×g for 10 minutes at 10° C. The supernatant was centrifuged at 40,000×g for 20 minutes at 0° C. and the resulting pellet was homogenized in 30 volumes of ice-cold 50 mM Tris-HCl buffer (pH 7.7), and incubated at 37° C. for 10 minutes. The suspension was centrifuged at 40,000×g for 20 minutes at 0° C. again. The resulting pellet was homogenized in 100 volumes of the above buffer and provided as synaptosome membranes solution for the next assay.

To the aliquots (900 μl) of synaptosome membranes solution were added 50 μl of $^3$H-Ketanserin solution at the terminal concentration of 0.2 nM and 50 μl of test compound solution or 50 μl of its medium, and incubated at 37° C. for 20 minutes. After completion of the reaction, the mixture was rapidly vacuum-filtered through Whatman GF/B filters. The filters were washed three times with 5 ml of the above buffer, and then the radioactivity of the residue remaining on the filters was measured by liquid scintillation counter. Nonspecific binding was determined under the presence of 10 μM of mianserin. 50% Inhibition concentration ($IC_{50}$) of the test compound was graphically determined and the inhibition constant (Ki value) was calculated. The results are summarized in Table A.

EXPERIMENT 3

Affinity for dopamine 2 ($D_2$) receptor ($^3$-H-Spiperone binding test)

Preparation of crude synaptosome fraction and binding assay were conducted in accordance with the method reported in European Journal of Pharmacology, vol. 46, page 377, 1977 by I. Creese et al. Freezed corpus striatum dissected out from rats were homogenized in 100 volumes of ice-cold 50 mM Tris-HCl buffer (pH 7.7) and the suspension was centrifuged at 500×g for 10 m minutes at 0° C. The supernatant was centrifuged at 50,000×g for 15 minutes at 0° C. and the resulting pellet was homogenized in 100 volumes of the above buffer, and then the suspension was centrifuged at 50,000×g for 15 minutes at 0° C. again. The resulting pellet was homogenized in 150 volumes of 50 mM Tris-HCl buffer (pH 7.1) containing 120 mM sodium chloride, 5 mM potassium chloride, 2 mM calcium chloride, 1 mM magnesium chloride, 0.1% ascorbic acid and 10 μM pargyline. The suspension was incubated at 37° C. for 10 minutes and then provided as synaptosome membranes solution for the next assay.

To the aliquots (900μl) of synaptosome membranes solution were added 50 μl of $^3$H-Spiperone solution at the terminal concentration of 0.2 nM and 50 μl of test compound solution or 50 μl of its medium, and incubated at 37° C. for 20 minutes. After completion of the reaction, the mixture was rapidly vacuum-filtered through Whatman GF/B filters. The filters were washed three times with 5 ml of the above buffer, and then the radioactivity of the residue remaining on the filters was measured by liquid scintillation counter. Nonspecific binding was determined under the presence of 100 μM of (±)-Sulpiride. 50% Inhibition concentration ($IC_{50}$) of the test compound was graphically determined and the inhibition constant (Ki value) was calculated. The results are summarized in Table A.

TABLE A

| Example No. of test compound | Receptor binding Ki (nM) | | |
| --- | --- | --- | --- |
| | $5\text{-HT}_{1A}$ | $5\text{-HT}_2$ | $D_2$ |
| 11 | 0.89 | 900.0 | 100.0 |
| 13 (maleate) | 1.6 | 1400.0 | 190.0 |
| 15 (hydrochloride) | 2.1 | 1500.0 | 140.0 |
| 46 | 1.3 | 990.0 | 78.0 |
| 103 | 5.2 | 1800.0 | 1800.0 |
| 107 | 1.5 | 990.0 | 120.0 |
| 117 | 4.1 | 1800.0 | 270.0 |
| 121 | 1.4 | 1100.0 | 150.0 |
| 155 | 0.81 | 2100.0 | 170.0 |
| 163 | 0.15 | 1200.0 | 6.2 |

EXPERIMENT 4

Anxiolytic effect (Vogel type conflict test)

The test was conducted according to the method of Vogel et al. Wistar rats deprived of water for 72 hours before the test were used. The rats were placed in a plexiglas conflict test box (light compartment: 38×38×20 cm, dark compartment: 10×10×20 cm). A water bottle with a stainless steel spout was fitted to the middle of the outside, so that the spout extended 3 cm into the box at a height of 10 cm above the grid floor. A drinkometer circuit (Ohara Inc., Nihon Koden) was connected with the spout and the number of licks were counted. The rat was placed into the apparatus where an electric shock (0.2–0.3 mA, 0.3 sec) was given once every 20th lick. After the rat received first electric shock, the number of shocks were recorded during the subsequent 3 min. test period. The test compounds were administered orally 1 hour before the test. The minimum effective dose (MED) was defined as the lowest dose producing a statistically significant difference between 0.5% MC-treated (control) and test drug treated punished responses (One-way ANOVA test; $P<0.05$). The results are summarized in Table B.

TABLE B

| Example No. of test compound | Anxiolytic effect MED (mg/kg, p.o.) |
| --- | --- |
| 13 (maleate) | 1.0 |
| 15 (hydrochloride) | 2.5 |

TABLE B-continued

| Example No. of test compound | Anxiolytic effect MED (mg/kg, p.o.) |
| --- | --- |
| 46 | ≦1.0 |
| 117 | 5.0 |
| 155 | 2.5 |
| 163 | 2.5 |

EXPERIMENT 5

Toxicity

All ddY male mice survived after five days following the oral (1000 mg/kg) and the intraperitoneal (300 mg/kg) administration of the test compounds of the present invention.

From the results of various pharmacological experiments, the compounds (I) of the present invention have high affinity for serotonin 1A ($5\text{-HT}_{1A}$), serotonin 2 ($5\text{-HT}_2$) and/or dopamine 2 ($D_2$) receptors. Among them, compounds having selective high affinity for $5\text{-HT}_{1A}$ receptor are useful as potent antianxietic drug with less side effects in the extrapyramidal system (EPS). The compounds having high affinity for not only $D_2$ receptor but also $5\text{-HT}_{1A}$ and $5\text{-HT}_2$ receptors are useful as antipsychotic drug which are effective on negative symptoms such as apathy, abulia or disorder of cognition as well as on positive symptoms such as hallucination, delusion or psychomotor excitement with reduced side effects, for example, EPS. Further, the compounds of the present invention can also be used as drugs for the disease of circulatory system, such as antihypertensive drug which lower arterial pressure and decrease heart rate by interacting with $5\text{-HT}_{1A}$ receptors.

When the compounds of formula (I) of the present invention are used as pharmaceuticals, a therapeutically effective amount of the compounds and adequate pharmacologically acceptable additives such as excipient, carrier, diluent and so on are mixed to be formulated into a form such as tablets, capsules, granules, syrups, injectable solutions, suppositories, dispersible powders or the like and are administered in the form mentioned above. The dosage may generally range about 5 to about 500 mg per day for an adult in a single dose or divided doses in the case of oral administration.

Formulation Example of the Pharmaceutical Composition:

Tablets containing 10 mg of the compound of formula (I) can be prepared by the following composition.

| | |
| --- | --- |
| Compound (I) | 10.0 mg |
| Lactose | 58.5 mg |
| Corn starch | 25.0 mg |
| Crystalline cellulose | 20.0 mg |
| Polyvinyl pyrrolidone K-30 | 2.0 mg |
| Talc | 4.0 mg |
| Magnesium stearate | 0.5 mg |
| | 120.0 mg |

Compound (I) is pulverized with an atomizer to make fine powder having an average particle size below 10 μ. The fine powder of compound (I), lactose, corn starch and crystalline cellulose are mixed well in a kneader and then kneaded with a binder paste prepared by polyvinyl pyrrolidone K-30. The wet mass is passed through a 200 mesh sieve and then dried in an oven at 50° C. The dry granule containing 3 to 4% of water content is forced through a 24 mesh sieve. Talc and magnesium stearate are mixed and compressed into tablets by using a rotatory tableting machine with a flat punch of 8 mm diameter.

The present invention will be explained in more detail by the following examples, but these examples are not to be construed as limiting the present invention.

EXAMPLE 1

To a solution of 10 g of 5,6,7,8-tetrahydro-4H-thieno[3,2-c]azepin-4-one in 120 ml of dimethylformamide was added 8.7 g of potassium t-butoxide with stirring under ice-cooling and the mixture was stirred at room temperature for 2 hours. Then, to the mixture was added 9.0 ml of 4-bromo-1-chlorobutane under ice-cooling and the solution was stirred at room temperature for 4 hours. After completion of the reaction, the reaction mixture was poured into chilled water and extracted with ethyl acetate. The extract was washed with water, dried over magnesium sulfate and then concentrated under reduced pressure. The resulting residue was chromatographed on a silica gel using chloroform as an eluent to give 10.0 g of 5-(4-chlorobuyl)-5,6,7,8-tetrahydro-4H-thieno[3,2c]-azepin-4-one as a pale yellow oil.

EXAMPLE 2

To a solution of 7.4 g of 5,6,7,8-tetrahydro-4H-thieno[3,2-b]azepin-4-one in 70 ml of dimethylformamide is added 6.5 g of potassium t-butoxide with stirring under ice-cooling and the mixture was stirred at room temperature for 4 hours. Then, to the mixture was added 6.6 g of 4-bromo-1-chlorobutane under ice-cooling and the solution was stirred at room temperature for 2 hours. After completion of the reaction, the reaction mixture was poured into chilled water and extracted with ethyl acetate. The exact was washed with water, dried over magnesium sulfate and then concentrated under reduced pressure. The resulting residue was chromatographed on a silica gel using chloroform as an eluent to give 9.5 g of 4-(4-chlorobutyl)-4,6,7,8-tetrahydro-5H-thieno[3,2-b]azepin-5-one as a pale yellow oil.

The following compounds can be prepared in a similar manner as the above examples:

EXAMPLE 3

5-(4-Chlorobutyl)-2-methyl-5,6,7,8-tetrahydro-4H-thieno[3,2-c]azepin-4one

EXAMPLE 4

4-(4-Chlorobutyl)-2-methyl-4,6,7,8-tetrahydro-5H-thieno[3,2-b]azepin-5-one

EXAMPLE 5

To a solution of 3.0 g of 5-(4-chlorobutyl)-5,6,7,8-tetrahydro-4H-thieno[3,2-c]azepin-4-one in 20 ml of acetic acid was added dropwise a solution of 2.1 g of bromine in 5 ml of acetic acid for 10 minutes. After the mixture was stirred at room temperature for 3 hours, the mixture was poured into chilled water and extracted with chloroform. The extract was washed with water, dried over magnesium sulfate and then concentrated under reduced pressure to give 4.0 g of 2-bromo-5-(4-chlorobutyl)-5,6,7,8-tetrahydro-4H-thieno[3,2-c]azepin-4-one as a pale brown oil. The obtained compound was employed in the subsequent reaction without purification.

The following compound can be prepared in a similar manner as the above example:

EXAMPLE 6

2-Bromo-4-(4-chlorobutyl)-4,6,7,8-tetrahydro-5H-thieno[3,2-b]-azepin-5-one

EXAMPLE 7

To an ice-cooled suspension of 2.8 g of aluminum chloride in 20 ml of dichloromethane was added 1.7 g of acetyl chloride and the mixture was stirred for 10 minutes at the same temperature, and then to the solution was added a solution of 1.8 g of 5-(4-chlorobutyl)-5,6,7,8-tetrahydro-4H-thieno[3,2-c]azepin-4-one in 5 ml of dichloromethane. The resulting mixture was stirred for 5 hours at room temperature, poured into chilled water and then extracted with chloroform. The extract was washed with water, dried over magnesium sulfate and concentrated under reduced pressure. The resulting crystals were recrystallized form the mixed solvent of ethyl acetate and isopropyl ether to give 2-acetyl-5-(4-chlorobutyl)-5,6,7,8-tetrahydro-4H-thino[3,2-c]azepin-4-one as white crystals, melting at 64°-65° C.

The following compound can be prepared in a similar manner as the above example:

EXAMPLE 8

2-Acetyl-4-(4-chlorobutyl)-4,6,7,8-tetrahydro-5H-thieno[3,2-b]-azepin-5-one

EXAMPLE 9

To a solution of 3.0 g of 5-(4-chlorobutyl)-5,6,7,8-tetrahydro-4H-thieno[3,2-c]azepin-4-one in 50 ml of toluene-dimethylformamide (1:1) were added 3.0 g of N-(2-pyrimidinyl)piperazine dihydrochloride, 3.2 g of potassium carbonate and 2.0 g of potassium iodide and the mixture was stirred at 90° C.-100° C. for 6 hours. After cooling, the mixture was poured into water and extracted with ethyl acetate. The extract was washed with water, dried over magnesium sulfate and concentrated in vacuo. The resulting residue was dissolved in ethanol and to the solution was added 1 g of fumaric acid to form fumarate. The crystals were collected by filtration and recrystallized from ethanol to give 3.1 of 5-[4-(4-(2-pyrimidinyl)-1-piperazinyl)butyl]-5,6,7,8-tetrahydro-4H-thieno[3,2-c]azepin-4-one fumarate as white crystals, melting at 188°-190° C.

The following compounds can be prepared in a similar manner as the above example:

EXAMPLE 10

4-[4-(4-(2-Pyrimidinyl)-1-piperazinyl)butyl]-4,6,7,8-tetrahydro-5H-thieno[3,2-b]azepin-5-one fumarate, melting at 164°-166° C.

EXAMPLE 11

2-Bromo-5-[4-(4-(2-pyrimidinyl)-11-piperazinyl)-butyl]-5,6,7,8-tetrahydro-4H-thieno[3,2-c]azepin-4-one fumarate, melting at 174°-176° C.

EXAMPLE 12

2-Bromo-4-[4-(4-(2-pyrimidinyl)-1-piperazinyl)-butyl]-4,6,7,8-tetrahydro-5H-thieno[3,2-b]azepin-5-one fumarate, melting at 169°-172° C.

EXAMPLE 13

2-Acetyl-5-[4-(4-(2-pyrimidinyl)-1-piperazinyl)-]butyl]-5,6,7,8-tetrahydro-4H-thieno[3,2-c]azepin-4-one, melting at 103°-106° C. Its fumarate melts at 166°-169° C. Its maleate melts at 161°-163° C. Its hydrochloride melts at 205°-210° C.

EXAMPLE 14

2-Acetyl-4-[4-(4-(2-pyrimidinyl)-1-piperazinyl)-butyl]-4,6,7,8-tetrahydro-5H-thieno[3,2-b]azepin-5-one fumarate, melting at 159°-162° C.

EXAMPLE 15

2-Methyl-5-[4-(4-(2-pyrimidinyl)-1-piperazinyl)-]butyl]-5,6,7,8-tetrahydro-4H-thieno[3,2-c]azepin-4-one, melting at 86°-88° C. Its fumarate melts at 168°-172° C. Its hydrochloride melts at 197°-198° C.

EXAMPLE 16

2-Methyl-5-[6-(4-(2-pyrimidinyl-1-piperazinyl)]hexyl]-5,6,7,8-tetrahydro-4H-thieno[3,2-c]azepin-4-one maleate, melting at 108°-110° C.

EXAMPLE 17

To a solution of 3.5 of 2-acetyl-4-[4-(4-(2-pyrimidinyl)-1-piperazinyl)butyl]-4,6,7,8-tetrahydro-5H-thieno[3,2-b]azepin-5-one in 35 ml of trifluoroacetic acid was added 2.7 ml of triethylsilane and the mixture was stirred for 20 hours at room temperature. Then, the mixture was poured into water, made alkaline with potassium carbonate and extracted with ethyl acetate. The extract was washed with water, dried and concentrated under reduced pressure. The residue was dissolved in acetone and to the solution was added 1.5 g of fumaric acid to produce its fumarate. The precipitated crystals were collected by filtration and recrystallized from ethanol to give 2.0 g of 2-ethyl-4-[4-(4-(2-pyrimidinyl)-1-piperazinyl)butyl]-4,6,7,8-tetrahydro-5H-thieno[3,2-b]-azepin-5-one fumarate as white crystals, melting at 156°-158° C.

The compounds shown in the Table 1 and Table 2 can be prepared in a similar manner as the above examples:

EXAMPLE 42

The reaction and procedure were conducted in the same manner as in Example 7 using propionyl chloride in place of acetyl chloride to give 5-(4-chlorobutyl)-5,6,7,8-tetrahydro-2-propionyl-4H-thieno[3,2-c]azepin-4-one as white crystals, melting at 91°-92° C.

The following compounds can be prepared in the same manner as in Example 9.

EXAMPLE 43

2-Methyl-4-[4-(4-(2-pyrimidinyl)-1-piperazinyl)-butyl]-4,6,7,8-tetrahydro-5H-thieno[3,2-b]azepin -5-one oxalate, melting at 155°-156° C.

EXAMPLE 44

2-Methyl-5-[3-(4-(2pyrimidinyl)-1-piperazinyl)-propyl]-5,6,7,8-tetrahydro-4H-thieno[3,2-c]azepin-4-one dihydrochloride, melting at 226°-227° C.

EXAMPLE 45

2-Propionyl-5-[4-(4-(2-pyrimidinyl)-1-piperazinyl)-butyl]-5,6,7,8-tetrahydro-4H-thieno[3,2-c]azepin-4-one, melting at 109°-111° C.

EXAMPLE 46

The reaction and procedure were conducted in the same manner as in Example 17 using 2-acetyl-5-[4-(4-(2-pyrimidinyl)-1-piperazinyl)butyl]-5,6,7,8-tetrahydro-4H-thieno[3,2-c]azepin-4-one in place of 2-acetyl-4-[4-(4-(2-pyrimidinyl)-1-piperazinyl)butyl]-4,6,7,8-tetrahydro-5H-thieno [3,2-b]azepin-5-one to give 2-ethyl-5-[4-(4-(2-pyrimidinyl)-1-piperazinyl)butyl]-5,6,7,8-tetrahydro-4H-thieno[3,2-c]azepin-4-one fumarate as white crystals, melting at 151°-154° C.

EXAMPLE 47

The reaction and procedure were conducted in the same manner as in Example 17 using 2-propionyl-5-[4-(4-(2-pyrimidinyl)-1-piperazinyl)butyl]-5,6,7,8-tetrahydro-4H-thieno[3,2-c]azepin-4-one in place of 2-acetyl-4-[4-(4-(2-pyrimidinyl)-1-piperazinyl)butyl]-4,6,7,8-tetrahydro-5H-thieno-[3,2-b]azepin-5-one to give 2-propyl-5-[4-(4-(2-pyrimidinyl)-1-piperazinyl)butyl]-5,6,7,8-tetrahydro-4H-thieno[3,2c]azepin-4one fumarate as white crystals, melting at 123°-125° C.

The following compounds can be prepared in a similar manner as the above examples.

EXAMPLE 48

2-Methyl-5-[4-(4-(2-pyrimidinyl)-1-piperazinyl)-butyl]-5,6,7,8-tetrahydro-4H-thieno[3,2-c]azepin-4-one, melting at 86°-88° C. Its hydrochloride melts at 197°-198° C.

EXAMPLE 49

4-[3-(4-(2-Pyrimidinyl)-1-piperazinyl)propyl]-4,6,7,8-tetrahydro-5H -thieno[3,2-b]azepin-5-one oxalate, melting 171°-173° C.

EXAMPLE 50

5-[5-(4-(2-Pyrimidinyl)-1-piperazinyl)pentyl]-5,6,7,8-tetrahydro-4 H-thieno[3,2-c]azepin-4-one fumarate, melting at 174°-176° C.

EXAMPLE 51

To a solution of 4.2 g of 5-(4-chlorobutyl)-2methyl-5,6,7,8-tetrahydro-4H-thieno[3,2-c]azepin-4-one in 50 ml of toluene-dimethyl-formamide (1:1) were added 4.8 g of 4-[bis(4-fluorophenyl)methylene]-piperidine, 4.6 g of potassium carbonate and 2.5 g of potassium iodide, and then the mixture was stirred for 6 hours at 90°-100° C. After cooling, the mixture was poured into water and extracted with ethyl acetate. The extract was washed with water, dried over magnesium sulfate and concentrated in vacuo. The resulting residue was dissolved in ethanol and to the solution was added 1.0 g of fumaric acid to produce its fumarate. The precipitated crystals were collected by filtration and recrystallized from ethanol to give 1.4 g of 5-[4-(4-(bis(4-fluorophenyl)methylene)piperidino)butyl]-2-methyl-5,6,7,8-tetrahydro-4H-thieno[3,2c]azepin-4-one fumarate as white crystals, melting at 203°-204° C.

EXAMPLE 52

4-[2-(4-(2-Methoxyphenyl)-1-piperazinyl)ethyl]-4,6,7,8-tetrahydro-5H-thieno[3,2-b]azepin-5-one, melting at 212°-214° C. with decomposition.

EXAMPLE 53

2-Methyl-5-(4-morpholinobutyl)-5,6,7,8-tetrahydro-4H-thieno[3,2-c]azepin-4-one hydrochloride, melting at 235°–236° C.

EXAMPLE 54

5-[4-(4-(4-Fluorobenzoyl)piperidino)butyl]-2-methyl-5,6,7,8-tetrahydro-4H-thieno[3,2-c]azepin-4-one hydrochloride, melting at 238°–241° C.

EXAMPLE 55

5-[4-(4-(1,3-Dihydro-2-oxo-2H-benzimidazol-1-yl)piperidino)butyl]-2-methyl-5,6,7,8tetrahydro-4H-thieno[3,2-c]azepin-4-one hydrochloride, melting at 259°–261° C.

EXAMPLE 56

To a solution of 5.0 g of 2-methyl-5,6,7,8-tetrahydro-4H-thieno[3,2-c]azepin-4-one in 70 ml of dimethylformamide was added 4.4 g of potassium t-butoxide with stirring under ice-cooling and the mixture was stirred for an hour at room temperature. To the mixture was added 7.1 g of bromoacetaldehyde (2-bromo-1,1-diethoxyethane) dropwise under ice-cooling. The mixture was stirred at 60° C. for 5 hours and poured into chilled water and then extracted with ethyl acetate. The extract was washed with brine, dried over magnesium sulfate and concentrated under reduced pressure. The resulting oil was chromatographed on a silica gel using chloroform as an eluent to give 2.5 g of 5-(2,2-diethoxyethyl)-2-methyl-5,6,7,8-tetrahydro-4H-thieno[3,2-c]-azepin-4-one as a pale yellow oil. To the solution of 2.1 g of 5-(2,2-diethoxyethyl)-2-methyl-5,6,7,8-tetrahydro-4H-thieno[3,2-c]azepin-4-one in 30 ml of tetrahydrofuran was added 10 ml of 10% hydrochloric acid solution, and the mixture was stirred for 2 hours at room temperature, poured into water and then extracted with ethyl acetate. The organic layer was washed with brine, dried over magnesium sulfate and concentrated under reduced pressure to give 1.39 g of 2-methyl-5,6,7,8-tetrahydro-4-oxo-4H-thieno[3,2-c]azepin-5-acetoaldehyde. To the solution of 1.39 g of 2-methyl-5,6,7,8-tetrahydro-4-oxo-4H-thieno[3,2-c]azepin-5-acetoaldehyde in 20 ml of ethanol were added 2.4 g of 4-[bis(4-fluorophenyl)methylene]piperidine and 0.39 g of sodium cyanoborohydride. The mixture was stirred for 2.5 hours at room temperature, poured into chilled water and extracted with ethyl acetate. The organic layer was washed with brine, dried over magnesium sulfate and concentrated under reduced pressure. The resulting orange oil was chromatographed on a silica gel using chloroform as an eluent and the eluate was concentrated under reduced pressure. The resulting residue was dissolved in ethanol and to the solution of the residue was added ethanolic hydrochloric acid to produce its hydrochloride. The precipitated crystals were collected by filtration and recrystallized from methanol to give 5-[2-(4-(bis(4-fluorophenyl)methylene)-piperidino)ethyl]-2-methyl-5,6,7,8-tetrahydro-4H -thieno[3,2-c]azepin-4-one hydrochloride as white crystals, melting at 228°–229° C.

EXAMPLE 57

5-[4-(4-(Bis(4-fluorophenyl)methyl)-1-piperazinyl)-butyl]-2-methyl-5,6,7,8-tetrahydro-4H-thieno[3,2-c]azepin-4-one dimaleate ½hydrate, melting at 131°–132° C.

EXAMPLE 58

5-[4-(4-(5-Chlorobenzoxazol-2-yl)-1-piperazinyl)-butyl]-2-methyl-5,6,7,8-tetrahydro-4H-thieno[3,2-c]azepin-4-one maleate, melting at 161°–162° C.

EXAMPLE 59

5-[6-(4-(3-Chlorophenyl)-1-piperazinyl)hexyl]-2-methyl-5,6,7,8-tetrahydro-4H-thieno[3,2-c]azepin-4-one maleate, melting at 149°–150° C.

EXAMPLE 60

5-[4-(4-(1,2-Benzisothiazol-3-yl)-1-piperazinyl)butyl]-2-methyl-5,6,7,8-tetrahydro-4H-thieno[3,2-c]azepin-4-one hydrochloride, melting at 231°–233° C.

EXAMPLE 61

5-[4-(4-(3-Trifluoromethylphenyl)-1-piperazinyl)-butyl]-5,6,7,8-tetrahydro-4H-thieno[3,2-c]azepin-4-one fumarate, melting at 179°–182° C.

EXAMPLE 62

5-[2-(4-(2-Methoxyphenyl)-1-piperazinyl)ethyl]-5,6,7,8-tetrahydro-4H-thieno[3,2-c]azepin-4-one hydrochloride, melting at 231°–233° C.

EXAMPLE 63

5-[4-(4-(2,3-Dimethylphenyl)-1-piperazinyl)butyl]-2-methyl-5,6,7,8-tetrahydro-4H-thieno[3,2-c]azepin-4-one hydrochloride, melting at 243°–247° C,

EXAMPLE 64

5-[4-(4-(2-Methoxyphenyl)-1-piperazinyl)butyl]-2-methyl-5,6,7,8-tetrahydro-4H-thieno[3,2-c]azepin-4-one hydrochloride monohydrate, melting at 207°–209° C.

The compounds shown in the Tables 3, 4 and 5 can be prepared in a similar manner:

EXAMPLE 93

To 300 g of polyphosphoric acid warmed at 70° C. was added 19.5 g of 5,6-dihydro-4H-thieno[2,3-b]thiopyran-4-one 4-oxime portionwise with stirring for 20 minutes. The mixture was stirred at 80° C. for 2.5 hours, poured into chilled water and extracted with chloroform. The extract was washed with water, dried over magnesium sulfate and concentrated under reduced pressure. The resulting crude crystals were recrystallized from ethanol to give 10 g of 2,3-dihydrothieno[3,2-f]-1,4-thiazepin-5(4H)-one as white crystals, melting at 195°–196° C.

EXAMPLE 94

The reaction and procedure were conducted in the same manner as in Example 93 using 5,6-dihydro-2-methyl-4H-thieno[2,3-b]thiopyran-4-one 4-oxime in place of 5,6-dihydro-4H-thieno[2,3-b]thiopyran-4-one 4-oxime to give 2,3-dihydro-7-methylthieno[3,2-f]-1,4-thiazepin-5(4H)-one as white crystals, melting at 155°–156° C.

EXAMPLE 95

From the crude product obtained by the reaction of Example 94 was removed the compound of Example 94 and the remaining mixture was purified to give 3,4-dihydro-7-methylthieno[2,3-b][1,4]thiazepin-2(1H)-one as white crystals, melting at 208°–210° C.

EXAMPLE 96

To a solution of 4.9 g of 2,3-dihydrothieno[3,2-f]-1,4-thiazepin-5(4H)-one in 50 ml of N,N-dimethylformamide is added 3.6 g of potassium t-butoxide with stirring under ice-cooling and the mixture was stirred at room temperature for an hour and then 5.4 g of 1-bromo-4-chlorobutane was added. The mixture was stirred for 5 hours, poured into water and extracted with ethyl acetate. The extract was washed with water, dried over magnesium sulfate and the solvent was distilled off. The resulting residue was chromatographed on a silica gel using chloroform and methanol (99.8:0.2) as an eluent to give 6.9 g of 4-(4-chlorobutyl)-2,3-dihydrothieno[3,2f]-1,4-thiazepin-5(4H)-one as pale yellow oil.

EXAMPLE 97

The reaction and procedure were conducted in the same manner as in Example 96 using 2,3-dihydro-7-methylthieno[3,2-f]-1,4-thiazepin-5(4H)-one in place of 2,3-dihydrothieno[3,2-f]-1,4-thiazepin-5(4H)-one to give 4-(4-chlorobutyl)-2,3-dihydro-7-methylthieno[3,2-f]-1,4-thiazepin-5(4H)-one.

EXAMPLE 98

The reaction and procedure were conducted in the same manner as in Example 96 using 3,4-dihydro-7-methylthieno[2,3-b][1,4]thiazepin-2(1H)-one in place of 2,3-dihydrothieno[3,2-f]-1,4-thiazepin-5(4H)-one to give 1-(4-chlorobutyl)-3,4-dihydro-7-methylthieno[2,3-b][1,4]-thiazepin-2(1H)-one.

EXAMPLE 99

To a suspension of 13 g of aluminum chloride in 150 ml of methylene chloride was added 4.6 ml of acetyl chloride under ice-cooling and the mixture was stirred for 15 minutes. To the mixture was added a solution of 9.0 g of 4-(4-chlorobutyl)-2,3-dihydrothieno[3,2-f]-1,4-thiazepin-5(4H)-one in 20 ml of methylene chloride and the mixture was stirred at room temperature of 2 hours. Then, the mixture was poured into chilled water and extracted with chloroform. The extract was washed with water, dried over magnesium sulfate and the solvent was distilled off. The resulting crystals were recrystallized from ethyl acetate to give 6.9 g of 7-acetyl-4-(4-chlorobutyl)-2,3-dihydrothieno-[3,2-f]-1,4-thiazepin-5(4H)-one as white crystals, melting at 132°–134° C.

EXAMPLE 100

To a solution of 3.0 g of 4-(4-chlorobutyl)-2,3-dihydrothieno[3,2-f]-1,4-thiazepin-5(4H)-one in 60 ml of acetic acid was added 1.5 ml of bromine with stirring at 60° C. and the mixture was stirred for 20 minutes at the same temperature. The mixture was poured into chilled water and extracted with chloroform. The extract was washed with water, dried over magnesium sulfate and the solvent was distilled off. The resulting crystals were recrystallized from ethanol to give 2.0 g of 7-bromo-4-(4-chlorobutyl)-2,3-dihydrothieno[3,2-f]-1,4-thiazepin-5(4H)-one as white crystals, melting at 81°–89° C.

EXAMPLE 101

To a solution of 8.0 g of 2,3-dihydrothieno[3,2-f]-1,4-thiazepin-5(4H)-one in 160 ml of N,N-dimethylformamide was added 6.3 g of potassium t-butoxide with stirring under ice-cooling and the mixture was stirred for an hour at room temperature. Then to the mixture was added 8.4 ml of bromoacetaldehyde diethyl acetal under ice-cooling. The mixture was stirred for 5 hours at room temperature and water was added thereto and extracted with ethyl acetate. The extract was washed with water, dried over magnesium sulfate and the solvent was distilled off. The residue was chromatographed on a silica gel using and chloroform and methanol (98.8:0.2) as an eluent to give 6,9 g of 4-(2,2-diethoxyethyl)-2,3-dihydrothieno[3,2-f]1,4-thiazepin-5(4H)-one as a pale yellow oil. To the solution of thus obtained 6.7 g of 4-(2,2-diethoxyethyl)-2,3-dihydrothieno[3,2-f]-1,4-thiazepin-5(4H)-one in 150 ml of tetrahydrofuran was added 20 ml of 10% hydrochloric acid and the mixture was allowed to stand for 20 hours at room temperature, and then poured into water and extracted with ethyl acetate. The extract was washed with water, dried over magnesium sulfate and the solvent was distilled off to give 4.4 g of 2,3,4,5-tetrahydro-5-oxothieno[3,2-f]-1,4-thiazepin-4-acetaldehyde as a pale yellow oil.

EXAMPLE 102

To a solution of 3.4 g of 4-(4-chlorobutyl)-2,3-dihydrothieno[3,2-f]-1,4-thiazepin-5(4H)-one in 100 ml of formic acid was added 2.9 ml of 30% hydrogen peroxide and the mixture was stirred for 3 hours at room temperature. Then, the mixture was poured into ca. 3% sodium hydrogensulfite solution and extracted with chloroform. The extract was washed with water, dried over magnesium sulfate and the solvent was distilled off to give 3.5 g of 4-(4-chlorobutyl)-2,3-dihydrothieno-[3,2-f]1,4-thiazepin-5(4H)-one 1,1-dioxide as a pale yellow oil.

EXAMPLE 103

To a solution of 4.4 g of 4-(4-chlorobutyl)-2,3-dihydrothieno-[3,2-f]-1,4-thiazepin-5(4H)-one in 100 ml of a mixed solvent of N,N-dimethylformamide and toluene (1:1) were added 5.2 g of N-(2-pyrimidinyl)piperazine and 4.4 g of potassium carbonate and the mixture was stirred for 5 hours at 80° C. Then, the mixture was poured into water and extracted with ethyl acetate. The extract was washed with water, dried over magnesium sulfate and the solvent was distilled off. The residue was chromatographed on a silica gel using chloroform and methanol (95:5) as an eluent and the resulting oil was dissolved in ethanol. To the solution was added fumaric acid to form fumarate and the precipitated crystals were recrystallized from ethanol to give 2.5 g of 2,3-dihydro-4-[4-(4-(2-pyrimidinyl)-1-piperazinyl)butyl]thieno[3,2-f]-1,4-thiazepin-5(4H)-one fumarate as white crystals, melting at 205°–210° C.

EXAMPLE 104

The reaction and procedure were conducted in the same manner as in Example 103 using N-(3-trifluoromethylphenyl)piperazine in place of N-(2-pyrimidinyl)piperazine to give 4-[4-(4-(3-trifluoromethylphenyl)-1-piperazinyl)butyl]-2,3-dihydrothieno[3,2-f]-1,4-thiazepin-5(4H)-one fumarate as white crystals, melting at 205°–206° C.

EXAMPLE 105

The reaction and procedure were conducted in the same manner as in Example 103 using N-(2-methoxyphenyl)piperazine in place of N-(2-pyrimidinyl)piperazine and using hydrochloric acid in place of fumaric acid to give 2,3-dihydro-4-[4-(4-(2-methoxyphenyl)-1-piperazinyl)butyl]thieno[3,2-f]-1,4-thiazepin-5(4H)-one hydrochloride ½hydrate as white crystals, melting at 211°–212° C.

EXAMPLE 106

The reaction and procedure were conducted in the same manner as in Example 103 using N-(1,2-benzisothiazol-3-yl)piperazine in place of N-(2-pyrimidinyl)piperazine and using hydrochloric acid in place of fumaric acid to give 4-[4-(4-(1,2-benzisothiazol-3-yl)-1-piperazinyl)-butyl]-2,3-dihydrothieno[3,2-f]-1,4-thiazepin-5(4H)-one hydrochloride as white crystals, melting at 231°–233° C.

EXAMPLE 107

To a solution of 2.0 g of 7-bromo-4-(4-chlorobutyl)-2,3-dihydrothieno[3,2f]-1,4-thiazepin-5(4H)-one in 40 ml of a mixed solvent of N,N-dimethylformamide and toluene (1:1) were added 1.9 g of N-(2-pyrimidinyl)piperazine dihydrochloride, 3.0 g of potassium carbonate and 1.3 g of potassium iodide and the mixture was stirred for 5 hours at 80° C. Then, the resultant mixture was poured into water and extracted with ethyl acetate. The extract was washed with water, dried over magnesium sulfate and the solvent was distilled off. The residue was dissolved in ethanol and to the solution was added fumaric acid to form its fumarate. The precipitated crystals were recrystallized from ethanol to give 2.5 go of 7-bromo-2,3-dihydro-4-[4-(4-(2-pyrimidinyl)-1-piperazinyl)butyl]thieno[3,2-f]-1,4-thiazepin-5(4H)-one fumarate ½ hydrate as white crystals, melting at 169°–170° C.

EXAMPLE 108

To a solution of 2.0 g of 4-(4-chlorobutyl)-2,3-dihydro-7-methyl-thieno[3,2-f]-1,4-thiazepin-5(4H)-one in 30 ml of a mixed solvent of N,N-dimethylformamide and toluene (1:1) were added 2.2 g of N-(2-methoxyphenyl)piperazine hydrochloride, 3.0 g of potassium carbonate and 0.5 g of potassium iodide and the mixture was stirred for 3 hours at 80° C. Then, the resulting mixture was poured into water and extracted with ethyl acetate. The extract was washed with water, dried over magnesium sulfate and the solvent was distilled off. The residue was dissolved in ethanol and to the solution was added oxalic acid to form its oxalate. The precipitated crystals were recrystallized from methanol to give 2.5 g of 2,3-dihydro-4-[4-(4-(2-methoxyphenyl)-1-piperazinyl)butyl]-7-methylthieno[3,2-f]-1,4-thiazepin-5(4H)-one oxalate monohydrate as white crystals, melting at 128°–130° C.

EXAMPLE 109

The reaction and procedure were conducted in the same manner as in Example 108 using N-[bis(4-fluorophenyl)methyl]piperazine in place of N-(2-methoxyphenyl)piperazine and using maleic acid in place of oxalic acid to give 4-[4-(4-(bis(4-fluorophenyl)methyl-1-piperazinyl)-butyl]-2,3-dihydro-7-methylthieno[3,2f]-1,4-thiazepin-5(4H)-one dimaleate ½hydrate as white crystals, melting at 165°–166° C.

EXAMPLE 110

The reaction and procedure were conducted in the same manner as in Example 108 using N-(diphenylmethyl)piperazine in place of N-(2-methoxyphenyl)piperazine and using maleic acid in place of oxalic acid to give 2,3-dihydro-7-methyl-4-[4-(4-diphenylmethyl)-1-piperazinyl)butyl] thieno[3,2-f]-1,4-thiazepin-5(4H)-one dimaleate as white crystals, melting at 166°–168° C.

EXAMPLE 111

The reaction and procedure were conducted in the same manner as in Example 108 using N-(3-trifluoromethylphenyl)piperazine in place of N-(2-methoxyphenyl)piperazine to give 4-[4-(4-(3-trifluoromethylphenyl)-1-piperazinyl)butyl]2,3-dihydro-7-methyl-thieno[3,2-f]-1,4-thiazepin-5(4H)-one oxalate as white crystals, melting at 135°–137° C.

EXAMPLE 112

The reaction and procedure were conducted in the same manner as in Example 108 using N-(2-pyrimidinyl)piperazine in place of N-(2-methoxyphenyl)piperazine and using fumaric acid in place of oxalic acid to give 2,3-dihydro-7-methyl-4-[4-(2-pyrimidinyl)-1-piperazinyl)butyl]thieno[3,2-f]-1,4-thiazepin-5(4H)-one fumarate as white crystals, melting at 196°–198° C.

EXAMPLE 113

The reaction and procedure were conducted in the same manner as in Example 108 using N-(hexadecyl)piperazine in place of N-(2-methoxyphenyl)piperazine and using hydrochloric acid in place of oxalic acid to give 4-[4-(4-hexadecyl)-1-piperazinyl)butyl]-2,3-dihydro-7-methylthieno[3,2f]-1,4-thiazepin-5(4H)-one dihydrochloride ½hydrate as white crystals, melting at 157°–159° C. with decomposition.

EXAMPLE 114

The reaction and procedure were conducted in the same manner as in Example 108 using N-(5-chloro-1,3-benzoxazol-2-yl)piperazine in place of N-(2-methoxyphenyl)piperazine and using maleic acid in place of oxalic acid to give 4-[4-(4-(5-chloro-1,3-benzoxazol-2-yl)-1-piperazinyl)butyl]-2,3-dihydro-7-methyl-thieno[3,2-f]-1,4-thiazepin-5(4H)-one maleate as white crystals, melting at 188°–189° C.

EXAMPLE 115

The reaction and procedure were conducted in the same manner as in Example 108 using N-[(4-chlorophenyl)phenylmethyl]piperazine in place of N-(2-methoxyphenyl)piperazine and using maleic acid in place of oxalic acid to give 4-[4-(4-(4-chlorophenyl)-phenylmethyl-1-piperazinyl)butyl]-2,3-dihydro-7-methylthieno[3,2-f]-1,4-thiazepin-5(4H)-one maleate as white crystals, melting at 157°–159° C.

EXAMPLE 116

To a solution of 2.0 g of 4-(6-chlorohexyl)-2,3-dihydro-7-methylthieno[3,2f]-1,4-thiazepin-5(4H)-one in 30 ml of a mixed solvent of N,N-dimethylformamide and toluene (1:1) were added 3.1 g of N-(2-pyrimidinyl)piperazine dihydrochloride, 3.0 g of potassium carbonate and 0.5 g of potassium iodide and the mixture was stirred for 3 hours at 80° C. Then, the resulting mixture was poured into water and extracted with ethyl acetate. The extract was washed with water, dried over magnesium sulfate and the solvent was distilled off. The residue was dissolved in ethanol and to the solution is added oxalic acid to form its oxalate. The precipitated crystals are recrystallized from methanol to give 1.3 g of 2,3-dihydro-7-methyl-4-[6-(4-(2-pyrimidinyl)-1-piperazinyl)hexyl]thieno[3,2-f]-1,4-thiazepin-5(4H)-one oxalate monohydrate as white crystals, melting at 161°–162° C.

EXAMPLE 117

To a solution of 6.8 g of 7-acetyl-4-(4-chlorobutyl)-2,3-dihydrothieno[3,2f]-1,4-thiazepin-5(4H)-one in 80 ml of a mixed solvent of N,N-dimethylformamide and toluene (1:1) were added 5.3 g of N-(2-pyrimidinyl)piperazine dihydochloride, 6.2 g of potassium carbonate and 3.6 g of potassium iodide and the mixture was stirred for 8 hours at 80° C. Then, the resulting mixture was poured into water and extracted with ethyl acetate. The extract was washed with water, dried over magnesium sulfate and the solvent was distilled off. The resulting crude crystals were recrystallized from isopropyl alcohol to give 9.4 g of 7-acetyl-2,3-dihydro-4-[4-(4-(2-pyrimidinyl)-1-piperazinyl)butyl]thieno[3,2-f]-1,4-thiazepin-5(4H)-one as white crystals, melting at 118°–120° C.

EXAMPLE 118

To a solution of 3.9 g of 2,3-dihydro-7-methyl-4-[4-(4-(2-pyrimidinyl)-1-piperazinyl)butyl]thieno[3,2-f]-1,4-thiazepin-5(4H)-one in 60 ml of acetic acid was added a solution of 2.5 g of sodium metaperiodate in 10 ml of water with stirring at room temperature and the mixture was stirred for 2.5 hours. Then, the mixture was poured into chilled water, made alkaline with potassium carbonate and extracted with chloroform. The extract was washed with water, dried over magnesium sulfate and the solvent was distilled off. The resulting residue was dissolved in isopropyl alcohol and to the solution was added hydrochloric acid to form hydrochloride. The precipitated crystals were recrystallized from ethanol to give 2.7 g of 2,3-dihydro-7-methyl-4-[4-(4-(2-pyrimidinyl)-1-piperazinyl)butyl]thieno[3,2-f]-1,4-thiazepin-5(4H)-one 1-oxide hydrochloride as white crystals, melting at 250°–252° C. with decomposition.

EXAMPLE 119

To a solution of 2.0 g of 7-acetyl-2,3-dihydro-4-[4-(4-(2-pyrimidinyl)-1-piperazinyl)butyl]thieno[3,2-f]-1,4-thiazepin-5(4H)-one in 20 ml of acetic acid was added to 1.0 g of 30% hydrogen peroxide and the mixture was stirred for 20 hours at room temperature. Then, the mixture was poured into ca. 3% aqueous sodium hydrogen sulfite solution and extracted with chloroform. The extract was washed with water, dried over magnesium sulfate and the solvent was distilled off. The resulting crude crystals were recrystallized from ethanol to give 1.5 g of 7-acetyl-2,3-dihydro-4-[4-(4-(2-pyrimidinyl)-1-piperazinyl)butyl]thieno[3,2-f]-1,4-thiazepin-5(4H)-one 1-oxide as white crystals, melting at 103°–106° C.

EXAMPLE 120

To a solution of 4.1 g of 4-(4-chlorobutyl)-2,3-dihydrothieno[3,2-f]-1,4-thiazepin-5(4H)-one 1,1-dioxide in 80 ml of a mixed solvent of N,N-dimethylformamide and toluene (1:1) were added 3.2 g of N-(2-pyrimidinyl)-piperazine dihydrochloride, 3.8 g of potassium carbonate and 2.3 g of potassium iodide and the mixture was stirred for 3 hours at 90° C. Then, the mixture was poured into water and extracted with ethyl acetate. The extract was washed with water, dried over magnesium sulfate and the solvent was distilled off. The resulting residue was chromatographed on a silica gel and eluted using chloroform and methanol (95:5) as an eluent. The resulting crystals were recrystallized from ethanol to give 3.0 g of 2,3-dihydro-4-[4-(4-(2-pyrimidinyl)-1-piperazinyl)butyl]thieno[3,2-f]-1,4-thiazepin-5(4H)-one 1,1-dioxide as white crystals, melting at 161°–163° C.

EXAMPLE 121

To a solution of 3.5 g of 7-acetyl-2,3-dihydro-4-[4-(4-(2-pyrimidinyl)-1-piperazinyl)butyl]thieno[3,2-f]-1,4-thiazepin-5(4H)-one in 35 ml of trifluoroacetic acid was added 2.9 ml of triethylsilane and the mixture was stirred for 20 hours at room temperature. Then, the mixture was poured into water, made alkaline with potassium carbonate and extracted with chloroform. The extract was washed with water, dried over magnesium sulfate and the solvent was distilled off. The resulting residue was dissolved in ethanol and to the solution was added hydrochloric acid to form hydrochloride. The precipitated crystals were recrystallized from ethanol to give 2.0 g of 7-ethyl-2,3-dihydro-4-[4-(4-(2-pyrimidinyl)-1-piperazinyl)thieno[3,2-f]-1,4-thiazepin-5(4H)-one hydrochloride 3/2 hydrate as white crystals, melting at 207°–209° C.

EXAMPLE 122

4-[2-(4-(Bis(4-fluorophenyl)methylene)piperidino)ethyl]-2,3-dihydrothieno[2,3-f]-1,4-thiazepin-5(4H)-one fumalate, melting at 205°–207° C.

EXAMPLE 123

4-[4-(4-(Bis(4-fluorophenyl)methylene)piperidino)butyl]-2,3-dihydro-7-methylthieno[3,2-f]-1,4-thiazepin-5(4H)-one maleate hydrate, melting at 96°–98° C.

EXAMPLE 124

4-[4-(4-(4-Fluorobenzoyl)piperidino)butyl]-2,3-dihydro-7-methylthieno[3,2-f]-1,4-thiazepin-5(4H)-one fumalate, melting at 184°–185° C.

EXAMPLE 125

2,3-Dihydro-7-methyl-4-(4-morpholinobutyl)-thieno[3,2-f]-1,4-thiazepin-5(4H)-one maleate, melting at 196°–197° C.

EXAMPLE 126

2,3-Dihydro-4-[4-(N-(2-(3,4-dimethoxyphenyl)ethyl)-N-methylamino)butyl]-7-methylthieno[3,2-f]-1,4-thiazepin-5(4H)-one fumalate, melting at 151°–152° C.

EXAMPLE 127

2,3-Dihydro-7-methyl-4-(4-piperidinobutyl)-thieno[3,2-f]-1,4-thiazepin-5(4H)-one maleate, melting at 158°–159° C.

EXAMPLE 128

4,5,6,7-Tetrahydro-7-[4-(4-(2-pyrimidinyl)-1-piperazinyl)butyl]-8H-thieno[2,3-c]azepin-8-one maleate, melting at 164°–167° C.

The compounds shown in the Tables 6 and 7 can be prepared in a similar manner.

EXAMPLE 153

2,3-Dihydro-7-methyl-4-[4-(2-oxo-1,2,3,5,6,7,8,8a-octahydroimidazo[1,2-a]pyridine-3-spiro-4'-piperidino)-butyl]thieno[3,2-f]-1,4-thiazepin-5(4H)-one maleate monohydrate, melting at 210°–211° C.

EXAMPLE 154

2-Methyl-5-[4-(4-(2-pyridyl)-1-piperazinyl)butyl]-5,6,7,8-tetrahydro-4H-thieno[3,2-c]azepin-4-one 3/2 maleate, melting at 167°–169° C.

EXAMPLE 155

2-(1-Hydroxyethyl)-5-[4-(4-(2-pyrimidinyl)-1-piperazinyl)butyl]-5,6,7,8-tetrahydro-4H-thieno[3,2-c]azepin-4-one maleate, melting at 159°–160° C.

EXAMPLE 156

4-[3-(4-(Bis(4-fluorophenyl)methyl-1-piperazinyl)-propyl]-2,3-dihydro-7-methylthieno[3,2-f]-1,4-thiazepin-5(4H)-one, melting at 100°–102° C.

EXAMPLE 157

4-(4-Aminobutyl)-2,3-dihydro-7-methylthieno[3,2-f]-1,4-thiazepin-5(4H)-one hydrochloride 1/4 hydrate, melting at 171°–172° C.

EXAMPLE 158

4-[4-(1,2,3,4-Tetrahydro-6,7-dimethoxy-2-isoquinolyl)butyl]-2,3-dihydro-7-methylthieno[3,2-f]-1,4-thiazepin-5(4H)-one maleate 1/4 hydrate, melting at 153°–154° C.

EXAMPLE 159

4-[3-(4-(2-Methoxyphenyl)-1-piperazinyl)propyl]-2,3-dihydro-7-methylthieno[3,2-f]-1,4-thiazepin-5(4H)-one dihydrochloride 1/2 hydrate, melting at 203°–205° C.

EXAMPLE 160

5-[4-(4-(Bis(4-fluorophenyl)methyl)-1-piperazinyl)-butyl]-5,6,7,8-tetrahydro-4H-thieno[3,2-c]azepin-4-one dimaleate, melting at 125°–128° C.

EXAMPLE 161

2-Methyl-5-[4-(4-(2-pyrimidinyl)-1-piperazinyl)-butyl]-5,6,7,8-tetrahydro-4H-thieno[3,2-c]azepin-4-thione hydrochloride 3/2 hydrate, melting at 235° C.

EXAMPLE 162

7-Methyl-4-[4-(4-(2-pyrimidinyl)-1-piperazinyl)-butyl]-2,3-dihydrothieno[3,2-f]-1,4-thiazepin-3(4H)-one fumalate, melting at 190°–192° C.

EXAMPLE 163

5-[4-((1,4-Benzodioxan-2-yl)methylamino)butyl]-2-methyl-5,6,7,8-tetrahydro-4H-thieno[3,2-c]azepin-4-one hydrochloride, melting at 189°–192° C.

EXAMPLE 164

To a solution of 2.0 g of 6,7,8,9-tetrahydrothieno[3,2-b]azocin-5(4H)-one in 20 ml of dimethylformamide was added 1.3 g of potassium t-butoxide under ice-cooling and stirred at the same temperature. To the mixture was added 2.0 g of 1-bromo-4-chlorobutane and stirred at room temperature for 5 hours. The mixture was poured into water and extracted ethyl acetate. The extract was washed with water, dried over anhydrous magnesium sulfate and concentrated in vacuo. The residue was chromatographed on a silica gel using a chloroform as an eluent to give 2.8 g of 4-(4-chlorobutyl)-6,7,8,9-tetrahydrothieno[3,2-b]azocin-5(4H)-one as a pale yellow oil.

EXAMPLE 165

The reaction and procedure are conducted in the same manner as in Example 164 using 6,7,8,9-tetrahydrothieno[3,2-c]azocin-4(5H)-one in place of 6,7,8,9-tetrahydrothieno[3,2-b]azocin-5(4H)-one to give 4-(4-chlorobutyl)-6,7,8,9-tetrahydrothieno[3,2-c]azocin-4(5H)-one.

EXAMPLE 166

To a solution of 2.8 g of 4-(4-chlorobutyl)-6,7,8,9-tetrahydrothieno[3,2-b]azocin-5(4H)-one in a mixed solvent of dimethylformamide (20 ml) and toluene (20 ml) was added 2.6 g of 2-pyrimidinyl-1-piperazine dihydrochloride, 4.3 g of potassium carbonate and 1.7 g of potassium iodide and stirred at 80° C. for 3 hours. After cooling, the mixture was poured into water and extracted with ethyl acetate. The extract was washed with water, dried and concentrated under reduced pressure. The resulting crystals were recrystallized from ethyl acetate to give 1.2 g of 6,7,8,9-tetrahydro-4-[4-(4-(2-pyrimidinyl)-1-piperazinyl)butyl]thieno[3,2-b]azocin-5(4H)-one as white crystals, melting at 108°–112° C.

EXAMPLE 167

The reaction and procedure were conducted in the same manner as in Example 166 using 4-(4-chlorobutyl)-6,7,8,9-tetrahydrothieno[3,2-c]azocin-4(5H)-one in place of 4-(4-chlorobutyl)-6,7,8,9-tetrahydrothieno[3,2-b]azocin-5(4H)-one and the obtained pale yellow oil was dissolved in ethanol. To the solution was added isopropyl alcohol-hydrochloric acid and the precipitated crystals were recrystallized from ethanol to give 6,7,8,9-tetrahydro-5-[4-(4-(2-pyrimidinyl)-1-piperazinyl)butyl]thieno[3,2-c]acozin-4(5H)-one hydrochloride 1/2 hydrate as white crystals, melting at 217°–222° C. with decomposition.

EXAMPLE 168

To a suspension of 6.0 g of 2-acetyl-5,6,7,8-tetrahydro-5-[4-(4-(2-pyrimidinyl)-1-piperazinyl)butyl]-4H-thieno[3,2-c]azepin-4-one maleate in 100 ml of ethanol were added 0.92 g of hydroxyamine hydrochloride and 4.0 g of sodium hydrogencarbonate with stirring and the mixture was refluxed for 5 hours. After cooling, the mixture was concentrated under reduced pressure, to the residue was added water and the solution was extracted with chloroform. The extract was washed with water, dried and concentrated in vacuo. The resulting crystals were recrystallized from a mixed solvent of ethanol and isopropyl ether to give 4.95 g of 5,6,7,8-tetrahydro-2-(1-(hydroxyimino)ethyl)-5-[4-(4-(2-pyrimidinyl)-1-piperazinyl)butyl]-4H-thieno[3,2-c]azepin-4-one as white crystals, melting at 144°–146° C.

EXAMPLE 169

To 30 g of 115% polyphosphate acid was added 2.4 g of 5,6,7,8-tetrahydro-2-(1-hydroxyimino)ethyl)-5-[4-(4-(2-pyrimidinyl)-1-piperazinyl)butyl]-4H-thieno[3,2-c]azepin-4-one with stirring at 70° C. The mixture was stirred at the same temperature for 3 hours, poured into chilled water and made to be alkaline solution with potassium carbonate. The precipitated crystals were collected by filtration, dried and chromatographed on a silica gel using chloroform-methanol (95:5) as an eluent. The resulting crystals were recrystallized from ethyl acetate to give 0.65 g of 2-acetylamino-5,6,7,8-tetrahydro-5-[4-(4-(2-pyrimidinyl)-1-piperazinyl)butyl]-4H- thieno[3,2-c]azepin-4-one as white crystals, melting at 158°–161° C.

EXAMPLE 170

To a suspension of 1.0 g of 5-[4-(1,4-benzodioxan-2-ylmethyl)amino)butyl]-2-methyl-5,6,7,8-tetrahydro-4H-thieno[3,2-c]azepin-4-one hydrochloride in 15 ml of ethanol was added 0.4 ml of formalin and then added 0.3 g of sodium cyanoborohydride with stirring at room temperature. The mixture was stirred at the same temperature for 2 hours, concentrated under reduced pressure and to the residue was added water, and then extracted with chloroform. The extract was washed with water, dried and concentrated in vacuo. The resulting oil was treated to form hydrochloride by a conventional method. The precipitated crystals were recrystallized from a mixed solvent of isopropyl alcohol and ethyl acetate to give 0.7 g of 5-[4-(N-(1,4-benzodioxan-2-ylmethyl)-N-methylamino)butyl]-2-methyl-5,6,7,8-tetrahydro-4H-thieno[3,2-c]azepin-4-one hydrochloride 1/4 hydrate as white crystals, melting at 193°–195° C.

EXAMPLE 171

To a solution of 5.0 g of 5,6,7,8-tetrahydro-2-methyl-4H-thieno[3,2-c]azepin-4-one in 70 ml of dimethylformamide was added 6.8 g of potassium t-butoxide under ice-cooling and stirred at room temperature for an hour. Then, to the mixture was added 4.4 g of dimethylaminoethylchloride hydrochloride and stirred at 60° C. for 5 hours. After cooling, to the mixture was added water and the solution was extracted with ethyl acetate. The extract was washed with water, dried and concentrated under reduced pressure. The resulting oil was treated to form hydrochloride by a conventional method. The precipitated crystals were recrystallized from a mixed solvent of ethanol and ethyl acetate to give 4.0 g of 5-(2-dimethylaminoethyl)-2-methyl-5,6,7,8-tetrahydro-4H-thieno[3,2-c]azepin-4-one hydrochloride as white crystals, melting at 229°–231° C.

EXAMPLE 172

To a solution of 0.9 g of 5-(2-dimethylaminoethyl)-2-methyl-5,6,7,8-tetrahydro-4H-thieno[3,2-c]azepin-4-one in 30 ml of acetone was added 0.4 ml of methyl iodide at room temperature. After being allowed to stand 30 minutes, the precipitated crystals were collected by filtration and washed with acetone to give 1.1 g of N-[2-(5,6,7,8-tetrahydro-2-methyl-4-oxo-4H-thieno[3,2-c]azepin-5-yl)ethyl]-N,N-dimethylammonium iodide as white crystals, melting at 237°–239° C.

EXAMPLE 173

To a suspension of 0.5 g of N-[2-(5,6,7,8-tetrahydro-2-methyl-4-oxo-4H-thieno[3,2-c]azepin-5-yl)ethyl]-N,N-dimethylammonium iodide in 20 ml of 1,3-dimethyl-2-imidazolidinone was added 0.52 g of 2-pyrimidinyl-1-piperazine and stirred at 130° C. for 4 hours. After cooling, the mixture was poured into water and extracted with ethyl acetate. The extract was washed with water, dried and concentrated in vacuo. The residue was chromatographed on a silica gel using chloroform-ethanol (97:3) as an eluent. The resulting crystals were recrystallized from a mixed solvent of ethyl acetate and isopropyl ether to give 0.2 g of 2-methyl-5-[2-(4-(2-pyrimidinyl)-1-piperazinyl)ethyl]-5,6,7,8-tetrahydro-4H-thieno[3,2-c]azepin-4-one as pale brown crystals, melting at 137°–139° C.

EXAMPLE 174

To a solution of 5.0 g of 5-(4-chlorobutyl)-5,6,7,8-tetrahydro-2-methyl-4H-thieno[3,2-c]azepin-4-one in 60 ml of acetic acid was added 1.9 ml of bromine at 60° C. and stirred for 20 minutes. After cooling, to the mixture was added an aqueous saturated sodium thiosulfate solution and the mixture was neutralized with potassium carbonate, and then extracted with ethyl acetate. The extract was washed with water, dried and concentrated under reduced pressure. The resulting crude crystals were recrystallized from a mixed solvent of isopropyl alcohol and hexane to give 2.3 g of 3-bromo-5-(4-chlorobutyl)-5,6,7,8-tetrahydro-2-methyl-4H-thieno[3,2-c]azepin-4-one as pale yellow crystals, melting at 78°–80° C.

EXAMPLE 175

To a solution of 2.2 g of 3-bromo-5-(4-chlorobutyl)-5,6,7,8-tetrahydro-2-methyl-4H-thieno[3,2-c]azepin-4-one in 50 ml of dimethylformamide-toluene (1:1) were added 1.6 g of 2-pyrimidinyl-1-piperazine dihydrochloride, 1.9 g of potassium carbonate and 1.2 g of potassium iodide and stirred at 80°–90° C. for 3 hours. After cooling, the mixture was poured into water and extracted with ethyl acetate. The extract was washed with water, dried and concentrated under reduced pressure. The residue was treated to form hydrochloride by a conventional method. The precipitated crystals were recrystallized from a mixed solvent of isopropyl alcohol and acetone to give 1.2 g of 3-bromo-5-[4-(4-(2-pyrimidinyl)-1-piperazinyl)butyl]-5,6,7,8-tetrahydro-2-methyl-4H-thieno[3,2-c]azepin-4-one hydrochloride 1/2 hydrate as white crystals, melting at 209°–213° C.

EXAMPLE 176

To a solution of 3.0 g of 4-(4-chlorobutyl)-2,3-dihydro-7-methylthieno[3,2-f][1,4]thiazepin-5(4H)-one in 30 ml of dimethylformamide was added 2.3 g of potassium phthalimide and stirred at 70°–80° C. for 6 hours. After cooling, the mixture was poured into water and extracted with ethyl acetate. The extract was washed with water, dried and concentrated in vacuo. The resulting crude crystals were recrystallized from methanol to give 4.6 g of 4-(4-phthalimidobutyl)-2,3-dihydro-7-methylthieno[3,2-f][1,4]thiazepin-5(4H)-one hydrate as white crystals, melting at 120°–121° C.

EXAMPLE 177

To a suspension of 4.0 g of 7-methyl-4-(4-phthalimidobutyl)-2,3-dihydrotheno[3,2-f][1,4]thiazepin-5(4H)-one in 40 ml of ethanol was added 1.5 ml of hydrazine hydrate and the mixture was refluxed under heating for 5 hours. After cooling, the precipitated crystals were filtered off and the filtrate was concentrated under reduced pressure. The resulting residue was chromatographed on a silica gel using chloroform-methanol (10:1) as an eluent. The resulting oil was treated to form hydrochloride by a conventional method and recrystallized from methanol to give 0.62 g of 4-(4-aminobutyl)-7-methyl-2,3-dihydrothieno[3,2-f][1,4]thiazepin-5(4H)-one hydrochloride 1/4 hydrate as white crystals, melting at 171°–172° C.

EXAMPLE 178

5-[4-(4-(6-Fluoro-1,2-benzisoxazol-3-yl)piperidino)butyl]-2-methyl-5,6,7,8-tetrahydro-4H-thieno[3,2-c]azepin-4-one hydrochloride, melting at 238°–241° C.

EXAMPLE 179

5-[6-(4-fluorophenyl)methyl-1-piperazinyl)hexyl]-2-methyl-5,6,7,8-tetrahydro-4H-thieno[3,2-c]azepin-4-one dimaleate 1/2 hydrate, melting at 106°–108° C.

EXAMPLE 180

4-[3-(4-(4-Chlorophenyl)-4-hydroxypiperidino)-propyl]-2,3-dihydro-7-methylthieno[3,2-f][1,4]thiazepin-5(4H)-one, melting at 144°–145° C.

EXAMPLE 181

4-[4-(4-(4-Chlorophenyl)-4-hydroxypiperidino)-butyl]-2,3-dihydro- 7-methylthieno[3,2-f][1,4]thiazepin-5(4H)-one hydrochloride, melting at 254°–255° C.

EXAMPLE 182

3-Acetyl-2-methyl-5-[4-(4-(2-pyrimidinyl)-1-piperazinyl)butyl]-5,6,7,8-tetrahydro-4H-thieno[3,2-c]azepin-4-one dioxalate, melting at 158°–159° C.

EXAMPLE 183

1,3-Dimethyl-4-[4-(4-(2-pyrimidinyl)-1-piperazinyl)butyl]-4,6,7,8-tetrahydro-5H-thieno[3,4-b]azepin-5-one hydrochloride, melting at 232°–234° C.

EXAMPLE 184

Methyl 2-methyl-5,6,7,8-tetrahydro-5-[4-(4-(2-pyrimidinyl)-1-piperazinyl)butyl]-4-oxo-4H-thieno[3,2-c]azepine-3-carboxylate

EXAMPLE 185

2-Methyl-5-[4-(4-(2-pyrimidinyl)-1-piperazinyl)-butyl]-5,6,7,8-tetrahydro-4H-thieno[3,2-c]azepine-4,6-dione

EXAMPLE 186

2-Methyl-5-[4-(4-(5-fluoro-2-pyrimidinyl)-1-piperazinyl)butyl]-5,6,7,8-tetrahydro-4H-thieno[3,2-c]azepine-4,6-dione

EXAMPLE 187

7-Methyl-4-[4-(4-(2-pyrimidinyl)-1-piperazinyl)-butyl]-2,3-dihydro-4H-thieno[3,2-f][1,4]thiazepine-3,5-dione

EXAMPLE 188

4-[4-(4-(5-Fluoro-2-pyrimidinyl)-1-piperazinyl)-butyl]-2,3-dihydro-7-methyl-4H-thieno[3,2-f][1,4]thiazepine-3,5-dione The compounds shown in the Tables 8 to 31 can be prepared in a similar manner. 381

TABLE 1

| No. | $R^1$ | $R^2$ | A | B | D | n | Q | T |
|---|---|---|---|---|---|---|---|---|
| 18 | H | $C_2H_5$ | C=O | — | $CH_2$ | 2 | —$(CH_2)_4$— | —N(piperazinyl)-N-2-pyrimidinyl |
| 19 | " | " | — | C=O | " | " | " | " |
| 20 | " | $C_3H_7$ | C=O | — | " | " | " | " |
| 21 | " | " | — | C=O | " | " | " | " |
| 22 | " | Cl | C=O | — | " | " | " | " |
| 23 | " | " | — | C=O | " | " | " | " |
| 24 | " | $CH_3$ | C=O | — | " | " | —$(CH_2)_2$— | " |
| 25 | " | " | — | C=O | " | " | " | " |
| 26 | $CH_3$ | " | C=O | — | " | " | —$(CH_2)_4$— | " |
| 27 | " | " | — | C=O | " | " | " | " |
| 28 | H | CHO | C=O | — | " | " | " | " |
| 29 | " | " | — | C=O | " | " | " | " |
| 30 | Cl | Cl | C=O | — | " | " | " | " |

TABLE 2

| No. | $R^1$ | $R^2$ | A | B | D | n | Q | T |
|---|---|---|---|---|---|---|---|---|
| 31 | Cl | Cl | — | C=O | $CH_2$ | 2 | —$(CH_2)_4$— | —N(piperazinyl)-N-2-pyrimidinyl |
| 32 | H | $CH_3$ | C=O | — | " | " | " | —N(piperazinyl)-N-(5-fluoro-2-pyrimidinyl) |
| 33 | " | " | — | C=O | " | " | " | " |

TABLE 2-continued
| No. | R¹ | R² | A | B | D | n | Q | T |
|---|---|---|---|---|---|---|---|---|
| 34 | " | I | C=O | — | " | " | " | 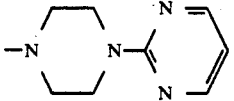 |
| 35 | " | " | — | C=O | " | " | " | " |
| 36 | " | 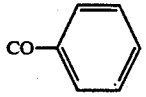 | C=O | — | " | " | —(CH₂)₅— | " |
| 37 | " | " | — | C=O | " | " | " | " |
| 38 | " | 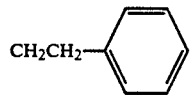 | C=O | — | " | " | —(CH₂)₄— | " |
| 39 | " | " | — | C=O | " | " | " | " |
| 40 | " | NO₂ | C=O | — | " | " | —(CH₂)₆— | " |
| 41 | " | " | — | C=O | " | " | " | " |
TABLE 3
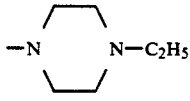
| No. | R¹ | R² | A | B | D | n | Q | T |
|---|---|---|---|---|---|---|---|---|
| 65 | H | CH₃ | C=O | — | CH₂ | 2 | —(CH₂)₄— | 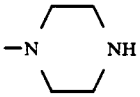 |
| 66 | " | H | " | " | " | " | " | 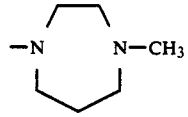 |
| 67 | " | " | " | " | " | " | " | 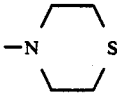 |
| 68 | " | " | " | " | " | " | " | 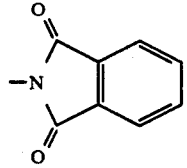 |
| 69 | " | " | " | " | " | " | " | 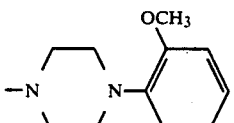 |
| 70 | " | COCH₃ | " | " | " | " | " |  |

TABLE 3-continued
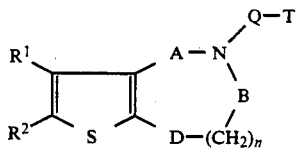
| No. | R¹ | R² | A | B | D | n | Q | T |
|---|---|---|---|---|---|---|---|---|
| 71 | " | CH₃ | " | " | " | " | —(CH₂)₃— | 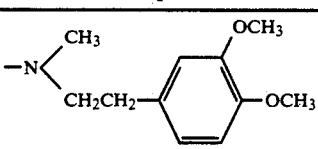 |
| 72 | " | " | " | " | " | " | —(CH₂)₄— | 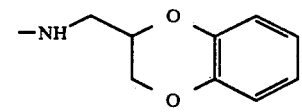 |
| 73 | " | H | " | " | " | " | —(CH₂)₃— | 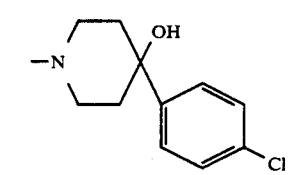 |
| 74 | " | CH₃ | " | " | " | " | " | 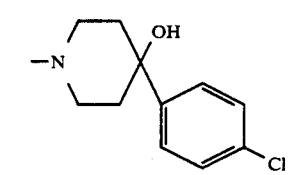 |
| 75 | " | " | " | " | " | " | —(CH₂)₄— | 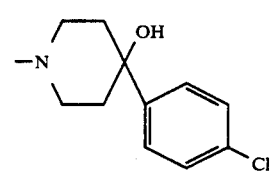 |
| 76 | " | " | " | " | " | " | " | 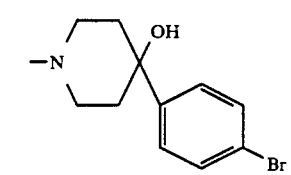 |
TABLE 4
| No. | R¹ | R² | A | B | D | n | Q | T |
|---|---|---|---|---|---|---|---|---|
| 77 | H | H | C=O | — | CH₂ | 2 | —(CH₂)₄— | 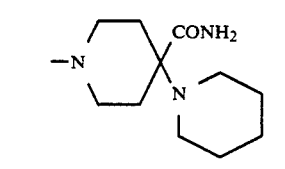 |
| 78 | " | CH₃ | " | " | " | " | " | 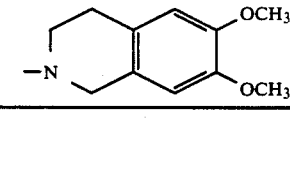 |
| 79 | " | H | " | " | " | " | " | 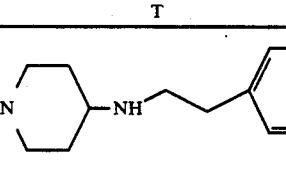 |

TABLE 4-continued

| No. | R¹ | R² | A | B | D | n | Q | T |
|---|---|---|---|---|---|---|---|---|
| 80 | " | CH₃ | " | " | " | " | " | 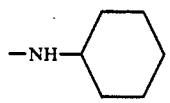 —NH-cyclohexyl |
| 81 | CH₃ | " | " | " | " | " | " | 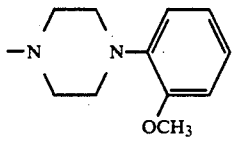 N-piperazinyl-(2-methoxyphenyl) |
| 82 | Cl | Cl | " | " | " | " | " | " |
| 83 | H | H | " | " | " | " | " | 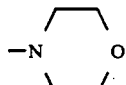 morpholino |
| 84 | " | CH₃ | " | " | " | " | " | 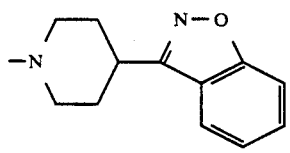 4-(1,2-benzisoxazol-3-yl)piperidinyl |
| 85 | " | " | " | " | " | " | " | —NH₂ |
| 86 | " | " | " | " | " | " | " | —NH—C₄H₉ |
| 87 | " | Br | " | " | " | " | " | 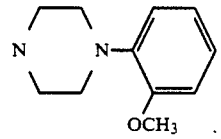 N-piperazinyl-(2-methoxyphenyl) |
| 88 | " | I | " | " | " | " | " | " |

TABLE 5

| No. | R¹ | R² | A | B | D | n | Q | T |
|---|---|---|---|---|---|---|---|---|
| 89 | H | C₂H₅ | C=O | — | CH₂ | 2 | —(CH₂)₄— | 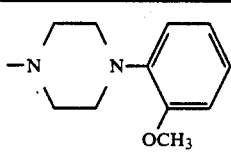 N-piperazinyl-(2-methoxyphenyl) |
| 90 | " | CHO | " | " | " | " | " | " |
| 91 | " | NO₂ | " | " | " | " | " | " |
| 92 | " | H | " | C=O | " | 1 | " | " |

TABLE 6

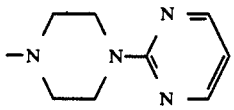

| No. | R¹ | R² | A | B | D | n | Q | T |
|---|---|---|---|---|---|---|---|---|
| 129 | H | COCH₃ | C=O | — | S | 2 | —(CH₂)₂— | N-piperazinyl-pyrimidin-2-yl |

TABLE 6-continued
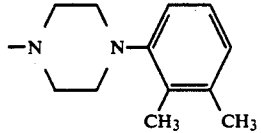
| No. | R¹ | R² | A | B | D | n | Q | T |
|---|---|---|---|---|---|---|---|---|
| 130 | " | CH₃ | " | " | " | " | —(CH₂)₄— | 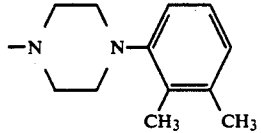 |
| 131 | " | CHCH₃<br>\|<br>OH | " | " | " | " | " | 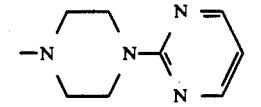 |
| 132 | " | CH₃ | " | " | " | " | —(CH₂)₃—C—<br>CH₃ CH₃ | " |
| 133 | " | " | " | " | " | " | —(CH₂)₄— | 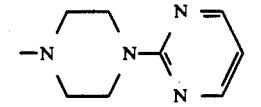 |
| 134 | " | " | " | " | " | " | " | 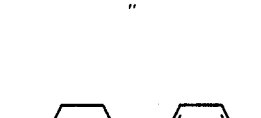 |
| 135 | " | " | " | " | " | " | " | 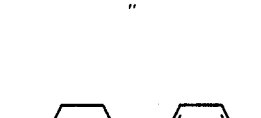 |
| 136 | " | " | " | " | " | " | " | 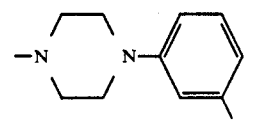 |
| 137 | " | " | " | " | " | " | " | 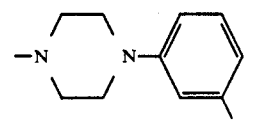 |
| 138 | " | SO₂N(CH₃)₂ | " | " | " | " | " | 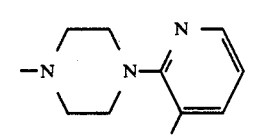 |
| 139 | " | COCH₃ | " | " | " | " | —(CH₂)₂— | 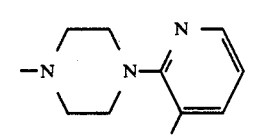 |
| 140 | " | CH₃ | " | " | " | " | —(CH₂)₄— | 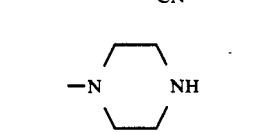 |

TABLE 7

| No. | R¹ | R² | A | B | D | n | Q | T |
|---|---|---|---|---|---|---|---|---|
| 141 | H | CH₃ | C=O | — | S | 2 | —(CH₂)₄— | 4-benzoylpiperazin-1-yl |
| 142 | " | " | " | " | " | " | " | 4-(2,3-ethylenedioxyphenyl)piperazin-1-yl |
| 143 | " | " | " | " | " | " | " | 4-(4-chloropyrimidin-2-yl)piperazin-1-yl |
| 144 | " | " | " | " | " | " | " | 4-(4-fluorophenyl)piperazin-1-yl |
| 145 | " | " | " | " | " | " | " | 4-(4-methylpyrimidin-2-yl)piperazin-1-yl |
| 146 | " | " | " | " | " | " | " | 4-(isoquinolin-1-yl)piperazin-1-yl |
| 147 | " | " | " | " | " | " | " | 4-(4-hydroxyphenyl)piperazin-1-yl |
| 148 | " | " | — | C=O | " | " | " | 4-(pyrimidin-2-yl)piperazin-1-yl |
| 149 | " | " | C=O | " | " | 1 | " | " |
| 150 | " | " | " | " | SO | " | " | " |
| 151 | " | " | " | " | S | " | " | 4-(3-trifluoromethylphenyl)piperazin-1-yl |
| 152 | " | " | " | " | " | " | " | 4-(3-chlorophenyl)piperazin-1-yl |

TABLE 8

| No. | R¹ | R² | A | B | D | n | Q | T |
|---|---|---|---|---|---|---|---|---|
| 201 | H | CH₃ | C=O | — | CH₂ | 2 | —(CH₂)₄— | piperazine-N–CH(phenyl)₂ |
| 202 | " | " | " | " | " | " | " | piperazine-N–(CH₂)₁₅CH₃ |
| 203 | " | Br | " | " | " | " | —(CH₂)₃—CH(CH₃)— | piperazine-N–CH(phenyl)(4-chlorophenyl) |
| 204 | " | " | " | " | " | " | " | piperidine |
| 205 | " | COCH₃ | " | " | " | " | —(CH₂)₅— | —N(CH₃)—CH₂CH₂–(3,4-dimethoxyphenyl) |
| 206 | " | " | " | " | " | " | " | piperazine-N–CH₃ |
| 207 | " | " | " | " | " | " | " | piperazine-N–(3-cyanopyridin-2-yl) |
| 208 | " | C₃H₇ | " | " | " | " | —(CH₂)₄— | piperazine-N–COOC₂H₅ |
| 209 | CH₃ | CH₃ | " | " | " | " | " | piperazine-N–CH₂CH₂–phenyl |

TABLE 8-continued

Structure: R¹, R² on thiophene (S) ring; A—N(Q—T)—B—D—(CH₂)ₙ

| No. | R¹ | R² | A | B | D | n | Q | T |
|-----|----|----|---|---|---|---|---|---|
| 210 | " | " | " | " | " | " | " | piperazine–CO–phenyl |
| 211 | H | " | " | " | " | " | " | piperazine–(2,3-dihydro-1,4-benzodioxin) |
| 212 | " | " | " | " | " | " | " | piperazine–(4-chloropyrimidin-2-yl) |

TABLE 9

| No. | R¹ | R² | A | B | D | n | Q | T |
|-----|----|----|---|---|---|---|---|---|
| 213 | H | NO₂ | C=O | — | CH₂ | 2 | —(CH₂)₄— | piperazine–(4-methylpyrimidin-2-yl) |
| 214 | " | CH₃ | " | " | " | " | " | piperazine–(isoquinolin-1-yl) |
| 215 | " | " | " | " | " | " | " | piperazine–(4-hydroxyphenyl) |
| 216 | " | SCH₃ | " | " | " | " | " | —N(C₈H₁₇)(C₈H₁₇) |
| 217 | " | " | " | " | " | " | " | piperazine–(4-fluorophenyl) |

TABLE 10
| No. | R¹ | R² | A | B | D | n | Q | T |
|---|---|---|---|---|---|---|---|---|
| 218 | H | CH₃ | C=O | — | S | 2 | —(CH₂)₄— | 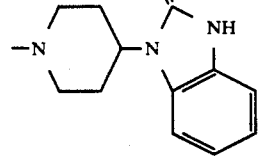 |
| 219 | " | " | " | " | " | " | " | 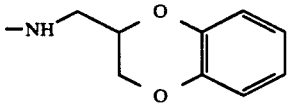 |
| 220 | " | Br | " | " | " | " | " | 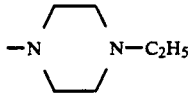 |
| 221 | " | " | " | " | " | " | " | 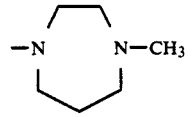 |
| 222 | " | " | " | " | SO | " | " | 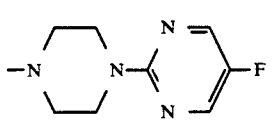 |
| 223 | " | " | " | " | " | " | —(CH₂)₂— | 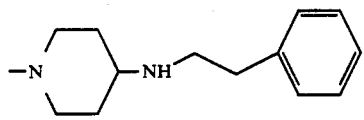 |
| 224 | Cl | Cl | " | " | " | " | —(CH₂)₆— | 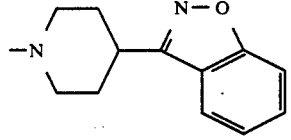 |
| 225 | H | " | " | " | S | " | " | 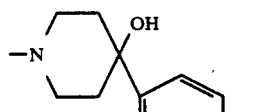 |
| 226 | " | CH₃ | " | " | " | " | " | 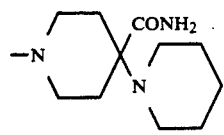 |
| 227 | " | " | " | " | " | " | —(CH₂)₄— | 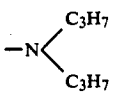 |
| 228 | " |  | " | " | " | " | " |  |

TABLE 10-continued
| No. | R¹ | R² | A | B | D | n | Q | T |
|-----|----|----|---|---|---|---|---|---|
| 229 | " | " | " | " | " | " | " | $-NH_2$ |
TABLE 11
| No. | R¹ | R² | A | B | D | n | Q | T |
|-----|----|----|---|---|---|---|---|---|
| 230 | H | $CH_3$ | C=O | — | S | 2 | $-(CH_2)_4-$ | $-NH-C_4H_9$ |
| 231 | " | " | " | " | " | " | " | 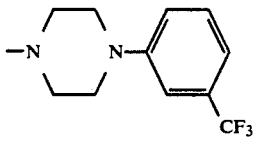 |
| 232 | " | $C_2H_5$ | " | " | " | " | " | 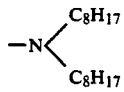 |
| 233 | " | " | " | " | " | " | " | 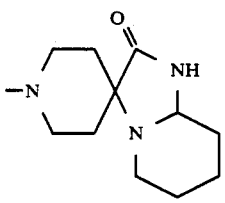 |
| 234 | " | $C_3H_7$ | " | " | " | " | " | 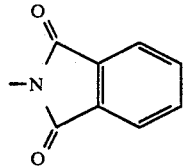 |
| 235 | " | " | " | " | " | " | " | 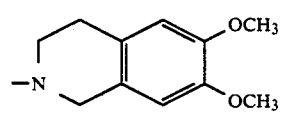 |
| 236 | H | I | " | " | " | " | " | 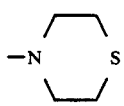 |
TABLE 12
| No. | R¹ | R² | A | B | D | n | Q | T |
|-----|----|----|---|---|---|---|---|---|
| 237 | H | $CH_3$ | — | C=O | $CH_2$ | 2 | $-(CH_2)_4-$ | 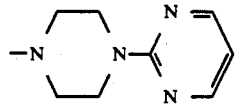 |
| 238 | " | " | " | " | " | " | " | 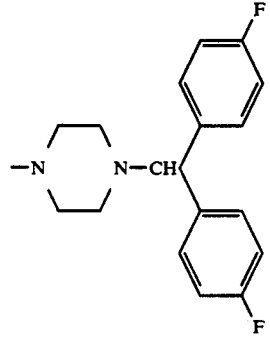 |

TABLE 12-continued
| No. | R¹ | R² | A | B | D | n | Q | T |
|---|---|---|---|---|---|---|---|---|
| 239 | " | Br | " | " | " | " | " | 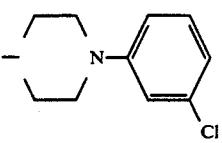 |
| 240 | " | " | " | " | " | " | " | 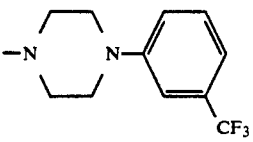 |
| 241 | " | Cl | " | " | " | " | " | 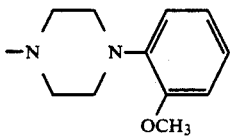 |
| 242 | " | CH₃ | " | " | " | " | " | 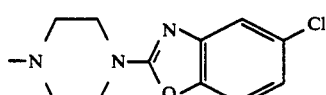 |
| 243 | " | " | " | " | " | " | " | 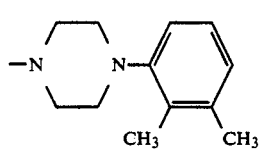 |
| 244 | " | COCH₃ | " | " | " | " | " | 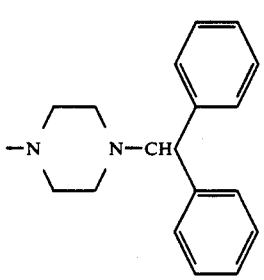 |
| 245 | " | " | " | " | " | " | " | 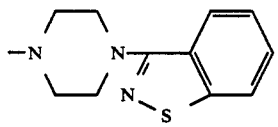 |
| 246 | " | Br | " | " | " | " | " | 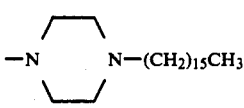 |
| 247 | " | CH₃ | " | " | " | " | " | 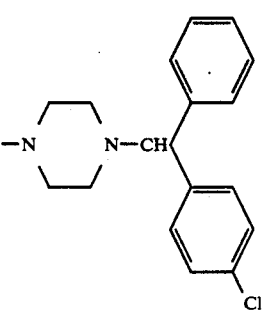 |

TABLE 12-continued

| No. | R¹ | R² | A | B | D | n | Q | T |
|---|---|---|---|---|---|---|---|---|
| 248 | CH₃ | " | " | " | " | " | " | (N-methylpiperidine with =C(4-F-C₆H₄)₂) |

TABLE 13

| No. | R¹ | R² | A | B | D | n | Q | T |
|---|---|---|---|---|---|---|---|---|
| 249 | H | CH₃ | — | C=O | CH₂ | 2 | —(CH₂)₄— | N-piperidinyl-4-CO-(4-F-C₆H₄) |
| 250 | " | " | " | " | " | " | " | N-methylpiperidin-4-yl benzimidazolone |
| 251 | " | Br | " | " | " | " | " | —NH—CH₂-(1,4-benzodioxan-2-yl) |
| 252 | " | C₂H₅ | " | " | " | " | " | morpholino |
| 253 | " | " | " | " | " | " | " | piperidino |
| 254 | " | CH₃ | " | " | " | " | " | —N(CH₃)—CH₂CH₂-(3,4-dimethoxyphenyl) |

TABLE 14

| No. | R¹ | R² | A | B | D | n | Q | T |
|---|---|---|---|---|---|---|---|---|
| 255 | H | CH₃ | — | C=O | S | 2 | —(CH₂)₄— | 4-(2-pyrimidinyl)piperazin-1-yl |

TABLE 14-continued
| No. | R¹ | R² | A | B | D | n | Q | T |
|-----|----|----|---|---|---|---|---|---|
| 256 | " | " | " | " | " | " | " | 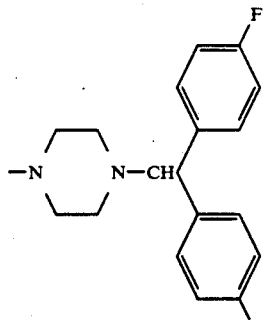 |
| 257 | " | " | " | " | " | " | " | 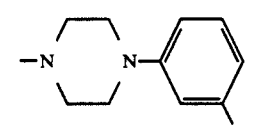 |
| 258 | " | " | " | " | " | " | " | 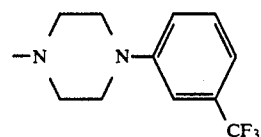 |
| 259 | " | SO₂NH₂ | " | " | " | " | " | 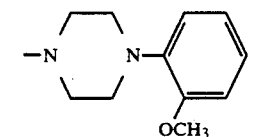 |
| 260 | " | Cl | " | " | " | " | " | 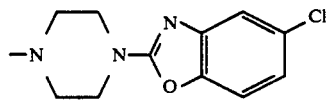 |
| 261 | " | COCH₃ | " | " | " | " | " | 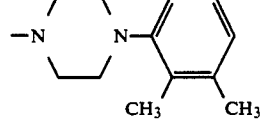 |
| 262 | " | " | " | " | SO | " | " | 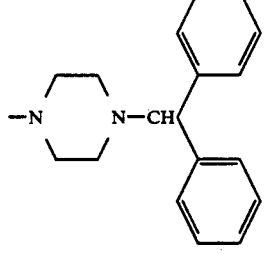 |
| 263 | " | CH₃ | " | " | S | " | " | 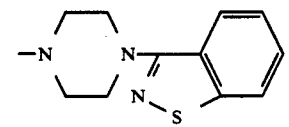 |
| 264 | " | H | " | " | " | " | " | 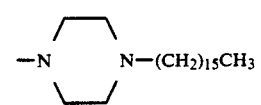 |

TABLE 14-continued
| No. | R¹ | R² | A | B | D | n | Q | T |
|-----|----|----|---|---|---|---|---|---|
| 265 | " | CH₃ | " | " | " | " | " | 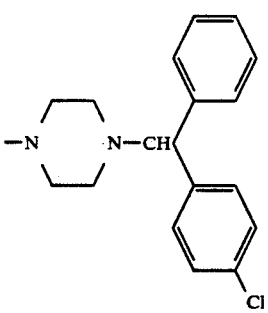 |
| 266 | " | Br | " | " | " | " | " | 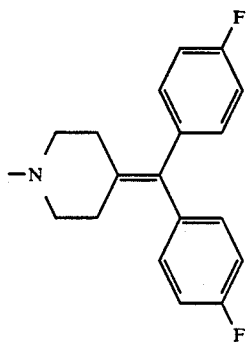 |
TABLE 15
| No. | R¹ | R² | A | B | D | n | Q | T |
|-----|----|----|---|---|---|---|---|---|
| 267 | H | Br | — | C=O | S | 2 | —(CH₂)₄— | 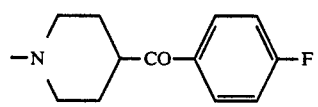 |
| 268 | " | 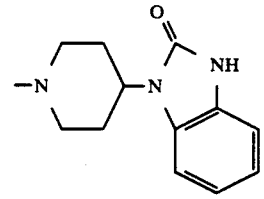 | " | " | " | " | " | 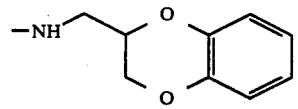 |
| 269 | " | CHO | " | " | " | " | " | 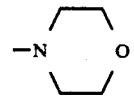 |
| 270 | " | C₂H₅ | " | " | " | " | " | 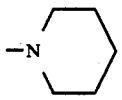 |
| 271 | " | CH₃ | " | " | " | " | " | 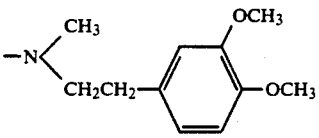 |
| 272 | " | " | " | " | " | " | " |  |

TABLE 16

| No. | R¹ | R² | A | B | D | n | Q | T |
|---|---|---|---|---|---|---|---|---|
| 273 | H | CH₃ | C=O | C=O | CH₂ | 1 | —(CH₂)₄— | piperazinyl-pyrimidin-2-yl |
| 274 | " | C₂H₅ | " | " | " | " | " | 4-[bis(4-fluorophenyl)methyl]piperazin-1-yl |
| 275 | " | CHO | " | " | " | " | " | 4-(3-chlorophenyl)piperazin-1-yl |
| 276 | " | Cl | " | " | " | " | " | 4-(3-trifluoromethylphenyl)piperazin-1-yl |
| 277 | " | " | " | " | " | " | " | 4-(2-methoxyphenyl)piperazin-1-yl |
| 278 | " | C₂H₅ | " | " | " | " | " | 4-(5-chlorobenzoxazol-2-yl)piperazin-1-yl |
| 279 | " | CH₃ | " | " | " | " | " | 4-(2,3-dimethylphenyl)piperazin-1-yl |
| 280 | " | H | " | " | " | " | " | 4-(diphenylmethyl)piperazin-1-yl |
| 281 | " | SO₂CH₃ | " | " | " | " | " | 4-(benzo[d]isothiazol-3-yl)piperazin-1-yl |

TABLE 16-continued
| No. | R¹ | R² | A | B | D | n | Q | T |
|---|---|---|---|---|---|---|---|---|
| 282 | " | " | " | " | " | " | " | 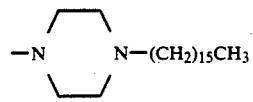 |
| 283 | " | CH₃ | " | " | " | " | " | 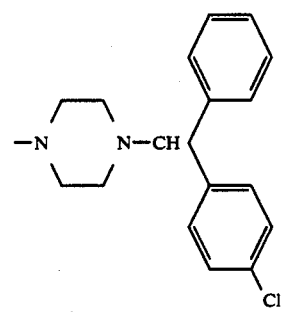 |
| 284 | " | CHO | " | " | " | " | " | 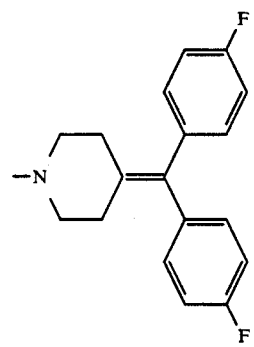 |
TABLE 17
| No. | R¹ | R² | A | B | D | n | Q | T |
|---|---|---|---|---|---|---|---|---|
| 285 | H | COCH₃ | C=O | C=O | CH₂ | 1 | —(CH₂)₄— | 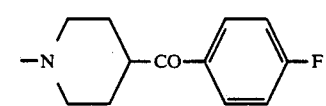 |
| 286 | " | SO₂NH₂ | " | " | " | " | " | 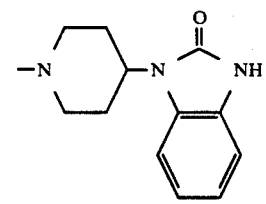 |
| 287 | " | Br | " | " | " | " | " | 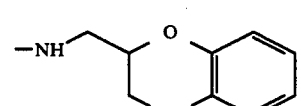 |
| 288 | " | CH₃ | " | " | " | " | " | 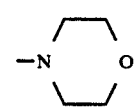 |
| 289 | " | " | " | " | " | " | " | 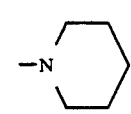 |

TABLE 17-continued
| No. | R¹ | R² | A | B | D | n | Q | T |
|-----|----|----|---|---|---|---|---|---|
| 290 | " | " | " | " | " | " | " | 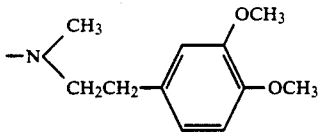 |
TABLE 18
| No. | R¹ | R² | A | B | D | n | Q | T |
|-----|----|----|---|---|---|---|---|---|
| 291 | H | CH₃ | C=O | C=O | S | 1 | —(CH₂)₄— | 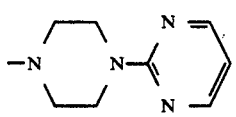 |
| 292 | " | CHO | " | " | " | " | " | 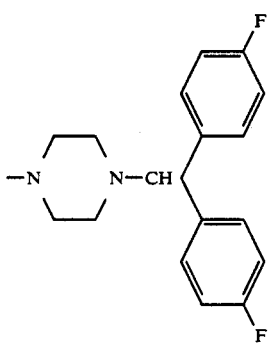 |
| 293 | " | COCH₃ | " | " | " | " | " | 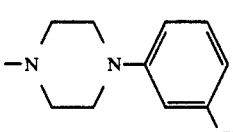 |
| 294 | " | " | " | " | " | " | " | 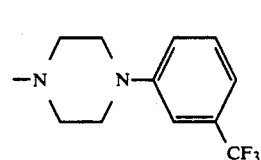 |
| 295 | " | " | " | " | " | " | " | 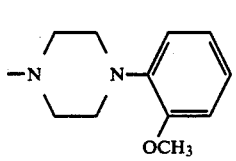 |
| 296 | " | Cl | " | " | " | " | " | 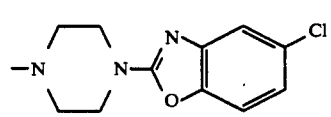 |
| 297 | " | CH₃ | " | " | " | " | " | 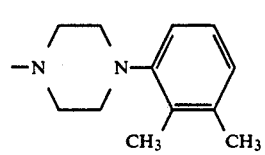 |

TABLE 18-continued

| No. | R¹ | R² | A | B | D | n | Q | T |
|---|---|---|---|---|---|---|---|---|
| 298 | " | " | " | " | " | " | " | piperazine-N-CH(phenyl)(phenyl) |
| 299 | " | SCH₃ | " | " | " | " | " | piperazine linked to benzisothiazole |
| 300 | " | " | " | " | " | " | " | piperazine-N-(CH₂)₁₅CH₃ |
| 301 | " | " | " | " | " | " | " | piperazine-N-CH(phenyl)(4-chlorophenyl) |
| 302 | " | C₂H₅ | " | " | " | " | " | piperidine=C(4-fluorophenyl)(4-fluorophenyl) |

TABLE 19

| No. | R¹ | R² | A | B | D | n | Q | T |
|---|---|---|---|---|---|---|---|---|
| 303 | H | CH₃ | C=O | C=O | S | 1 | —(CH₂)₄— | piperidine-4-CO-(4-fluorophenyl) |
| 304 | " | " | " | " | " | " | " | piperidine-N-(2-oxo-benzimidazolyl) |

TABLE 19-continued

| No. | R¹ | R² | A | B | D | n | Q | T |
|---|---|---|---|---|---|---|---|---|
| 305 | " | SO₂N(CH₃)₂ | " | " | " | " | " | -NH-CH₂-(2,3-dihydro-1,4-benzodioxin-2-yl) |
| 306 | " | COCH₃ | " | " | " | " | " | -N(morpholino) |
| 307 | " | " | " | " | " | " | " | -N(piperidino) |
| 308 | " | " | " | " | " | " | " | -N(CH₃)CH₂CH₂-(3,4-dimethoxyphenyl) |

TABLE 20

| No. | R¹ | R² | A | B | D | n | Q | T |
|---|---|---|---|---|---|---|---|---|
| 309 | H | CH₃ | — | C=O | CH₂ | 3 | —(CH₂)₄— | -N(piperazinyl)-2-pyrimidinyl |
| 310 | " | " | " | " | " | " | " | -N(piperazinyl)-N-CH(4-F-C₆H₄)(4-F-C₆H₄) |
| 311 | " | CHO | " | " | " | " | " | -N(piperazinyl)-(3-Cl-phenyl) |
| 312 | " | Br | " | " | " | " | " | -N(piperazinyl)-(3-CF₃-phenyl) |
| 313 | " | " | " | " | " | " | " | -N(piperazinyl)-(2-OCH₃-phenyl) |

TABLE 20-continued
| No. | R¹ | R² | A | B | D | n | Q | T |
|---|---|---|---|---|---|---|---|---|
| 314 | " | Cl | " | " | " | " | " | 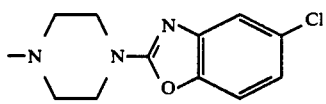 |
| 315 | " | COCH₃ | " | " | " | " | " | 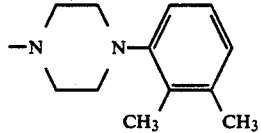 |
| 316 | " | SO₂N(CH₃)₂ | " | " | " | " | " | 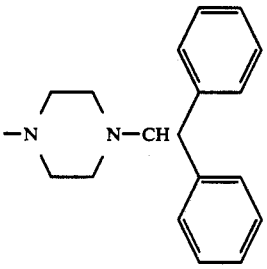 |
| 317 | " | C₂H₅ | " | " | " | " | " | 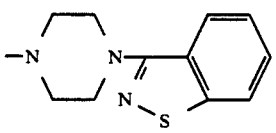 |
| 318 | " | CH₃ | " | " | " | " | " | 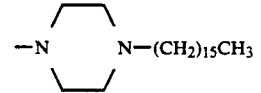 |
| 319 | " | " | " | " | " | " | " | 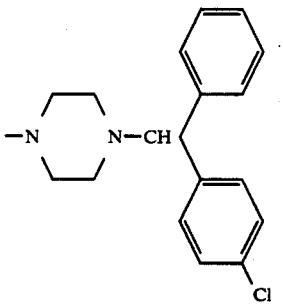 |
| 320 | " | " | " | " | " | " | " | 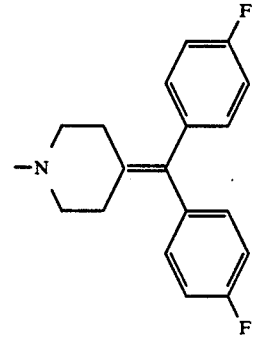 |

TABLE 21

| No. | R¹ | R² | A | B | D | n | Q | T |
|---|---|---|---|---|---|---|---|---|
| 321 | H | CH₃ | — | C=O | CH₂ | 3 | —(CH₂)₄— | 4-(4-fluorobenzoyl)piperidin-1-yl |
| 322 | " | H | " | " | " | " | " | 4-(2-oxo-2,3-dihydro-1H-benzimidazol-1-yl)piperidin-1-yl |
| 323 | " | C₂H₅ | " | " | " | " | " | —NH—CH₂—(1,4-benzodioxan-2-yl) |
| 324 | " | COC₆H₅ | " | " | " | " | " | morpholin-4-yl |
| 325 | " | H | " | " | " | " | " | piperidin-1-yl |
| 326 | " | CH₃ | " | " | " | " | " | —N(CH₃)—CH₂CH₂—(3,4-dimethoxyphenyl) |

TABLE 22

| No. | R¹ | R² | A | B | D | n | Q | T |
|---|---|---|---|---|---|---|---|---|
| 327 | H | CH₃ | C=O | — | CH₂ | 2 | —(CH₂)₄— | 4-(2-hydroxyethyl)piperazin-1-yl |
| 328 | " | " | " | " | " | " | " | 4-phenylpiperazin-1-yl |
| 329 | " | C₂H₅ | " | " | " | " | " | 4-(2-methylphenyl)piperazin-1-yl |
| 330 | " | Br | " | " | " | " | " | 4-(4-methylphenyl)piperazin-1-yl |
| 331 | " | " | " | " | " | " | " | 4-(3-cyanopropyl)piperazin-1-yl |

TABLE 22-continued
| No. | R¹ | R² | A | B | D | n | Q | T |
|---|---|---|---|---|---|---|---|---|
| 332 | " | Cl | " | " | " | " | " | 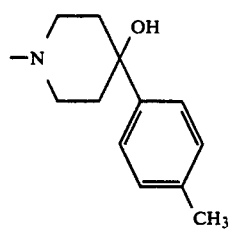 |
| 333 | " | " | " | " | " | " | " | 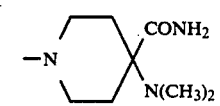 |
| 334 | " | " | " | " | " | " | " | 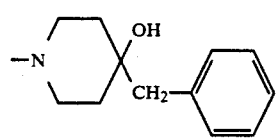 |
| 335 | " | $C_2H_5$ | " | " | " | " | " | 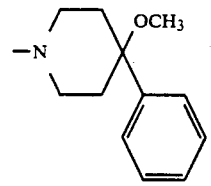 |
| 336 | " | $C_3H_7$ | " | " | " | " | " | 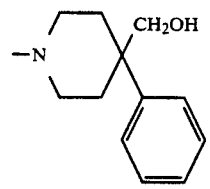 |
| 337 | " | $CH_3$ | " | " | " | " | " | 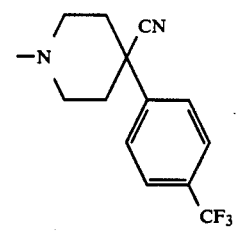 |
| 338 | " | " | " | " | " | " | " | 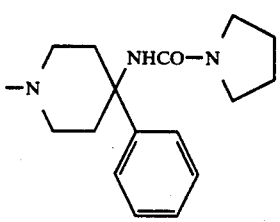 |

TABLE 23

| No. | R¹ | R² | A | B | D | n | Q | T |
|---|---|---|---|---|---|---|---|---|
| 339 | H | CH₃ | C=O | — | CH₂ | 2 | —(CH₂)₄— | piperidine with 4-phenyl and 4-COOC₂H₅ substituents |
| 340 | " | " | " | " | " | " | " | 4-hydroxypiperidine |
| 341 | " | " | " | " | " | " | " | 4-(2-thioxo-2,3-dihydrobenzimidazol-1-yl)piperidine |
| 342 | " | H | " | " | " | " | " | 4-(2,4-dioxotetrahydropyrimidin-1-yl)piperidine |
| 343 | " | " | " | " | " | " | " | 4-(4,4-dimethyl-3-methyl-2,5-dioxoimidazolidin-1-yl)piperidine |
| 344 | " | CH₃ | " | " | " | " | " | 4-(methylamino)piperidine |
| 345 | " | " | " | " | " | " | " | 4-(4-methylpiperazin-1-yl)piperidine |
| 346 | " | " | " | " | " | " | " | 4-(4-methoxyphenyl)piperidine |
| 347 | " | " | " | " | " | " | " | 4-piperidinopiperidine |
| 348 | " | " | " | " | " | " | " | spiro piperidine-thiazolidinone |

TABLE 23-continued
| No. | R¹ | R² | A | B | D | n | Q | T |
|---|---|---|---|---|---|---|---|---|
| 349 | " | " | " | " | " | " | " | 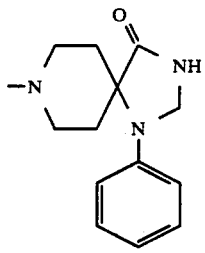 |
| 350 | " | " | " | " | " | " | " | 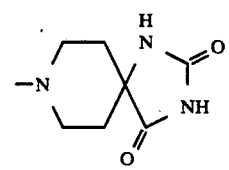 |
TABLE 24
| No. | R¹ | R² | A | B | D | n | Q | T |
|---|---|---|---|---|---|---|---|---|
| 351 | H | CH₃ | C=O | — | CH₂ | 2 | —(CH₂)₄— | 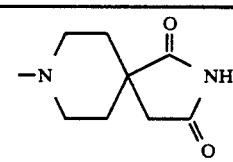 |
| 352 | " | " | " | " | " | " | " | 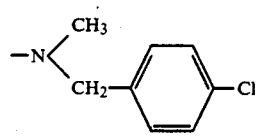 |
| 353 | " | " | " | " | " | " | " | 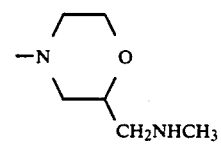 |
| 354 | " | SO₂N(CH₃)₂ | " | " | " | " | " | 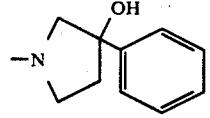 |
| 355 | " | " | " | " | " | " | " | 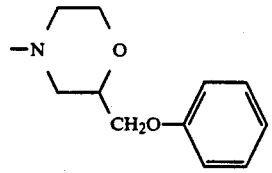 |
TABLE 25
| No. | R¹ | R² | A | B | D | n | Q | T |
|---|---|---|---|---|---|---|---|---|
| 356 | H | CH₃ | — | C=O | S | 2 | —(CH₂)₄— | 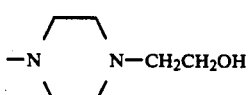 |
| 357 | " | " | " | " | " | " | " | 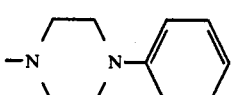 |

TABLE 25-continued

| No. | R¹ | R² | A | B | D | n | Q | T |
|-----|----|----|----|----|---|---|---|---|
| 358 | " | " | " | " | SO | " | " | -N(piperazine)-N-(2-methylphenyl) |
| 359 | " | " | " | " | S | " | " | -N(piperazine)-N-(4-methylphenyl) |
| 360 | " | $C_2H_5$ | " | " | " | " | " | -N(piperazine)-N-$(CH_2)_3CN$ |
| 361 | " | $C_6H_5CO$- | " | " | " | " | " | -N(piperidine)-4-OH, 4-(4-methylphenyl) |
| 362 | " | " | " | " | " | " | " | -N(piperidine)-4-$CONH_2$, 4-$N(CH_3)_2$ |
| 363 | " | $COC_2H_5$ | " | " | " | " | " | -N(piperidine)-4-OH, 4-$CH_2$-phenyl |
| 364 | " | $CH_3$ | " | " | " | " | " | -N(piperidine)-4-$OCH_3$, 4-phenyl |
| 365 | " | Cl | " | " | " | " | " | -N(piperidine)-4-$CH_2OH$, 4-phenyl |
| 366 | " | " | " | " | " | " | " | -N(piperidine)-4-CN, 4-(4-$CF_3$-phenyl) |

TABLE 25-continued
| No. | R¹ | R² | A | B | D | n | Q | T |
|---|---|---|---|---|---|---|---|---|
| 367 | " | " | " | " | " | " | " | 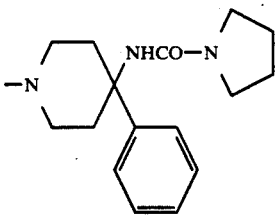 |
TABLE 26
| No. | R¹ | R² | A | B | D | n | Q | T |
|---|---|---|---|---|---|---|---|---|
| 368 | H | Br | — | C=O | S | 2 | —(CH$_2$)$_4$— | 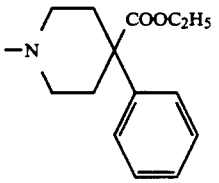 |
| 369 | " | H | " | " | " | " | " |  |
| 370 | " | CH$_3$ | " | " | " | " | " | 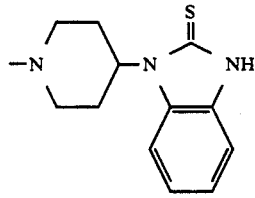 |
| 371 | " | " | " | " | " | " | " | 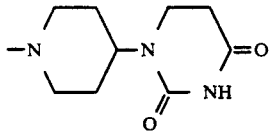 |
| 372 | " | " | " | " | " | " | " | 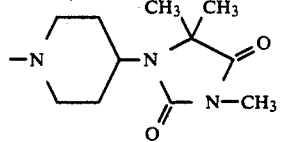 |
| 373 | " | " | " | " | " | " | " | 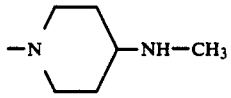 |
| 374 | " | " | " | " | " | " | " | 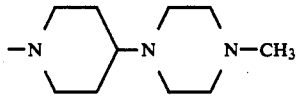 |
| 375 | " | " | " | " | " | " | " | 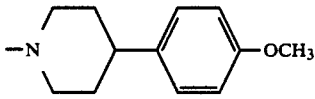 |
| 376 | " | " | " | " | " | " | " | 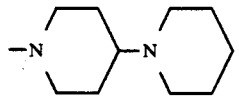 |

TABLE 26-continued

| No. | R¹ | R² | A | B | D | n | Q | T |
|---|---|---|---|---|---|---|---|---|
| 377 | " | " | " | " | " | " | " | 1-piperidinyl spiro-fused with thiazolidinone (S, NH, C=O) |
| 378 | " | " | " | " | " | " | " | 1-piperidinyl spiro-fused with 1-phenylimidazolidinone (N-Ph, NH, C=O) |
| 379 | " | C₂H₅ | " | " | SO₂ | " | " | 1-methylpiperidin-4-yl spiro-fused with hydantoin (NH—C(=O)—NH—C(=O)) |

TABLE 27

| No. | R¹ | R² | A | B | D | n | Q | T |
|---|---|---|---|---|---|---|---|---|
| 380 | H | C₂H₅ | — | C=O | SO | 2 | —(CH₂)₄— | 1-piperidinyl spiro-fused with γ-lactam (—CH₂—C(=O)—NH—) |
| 381 | " | " | " | " | " | " | " | —N(CH₃)—CH₂—(4-chlorophenyl) |
| 382 | " | H | " | " | S | " | " | 2-(methylaminomethyl)morpholin-4-yl |
| 383 | " | " | " | " | " | " | " | 3-hydroxy-3-phenylpyrrolidin-1-yl |
| 384 | " | " | " | " | " | " | " | 2-(phenoxymethyl)morpholin-4-yl |

TABLE 28
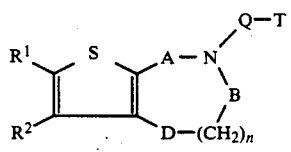
| No. | R¹ | R² | A | B | D | n | Q | T |
|-----|----|----|---|---|---|---|---|---|
| 385 | H | CH₃ | C=O | — | CH₂ | 2 | —(CH₂)₄— | |
| 386 | " | " | " | " | " | " | " | ₂) |
| 387 | " | Br | " | " | " | " | " | |
| 388 | " | " | " | " | " | " | " | |
| 389 | " | Cl | " | " | " | " | " | |
| 390 | " | CH₃ | " | " | " | " | " | |
| 391 | " | SO₂CH₃ | " | " | " | " | " | |

TABLE 28-continued
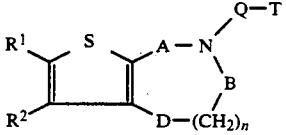
| No. | R¹ | R² | A | B | D | n | Q | T |
|---|---|---|---|---|---|---|---|---|
| 392 | " | COCH₃ | " | " | " | " | " | 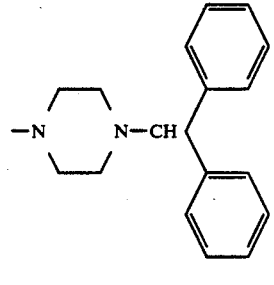 |
| 393 | " | " | " | " | " | " | " | 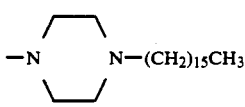 |
| 394 | " | Br | " | " | " | " | " | -N(piperazine)N-(CH₂)₁₅CH₃ |
| 395 | " | CH₃ | " | " | " | " | " | 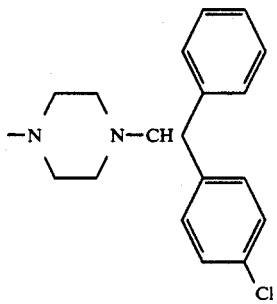 |
| 396 | " | " | " | " | " | " | " | 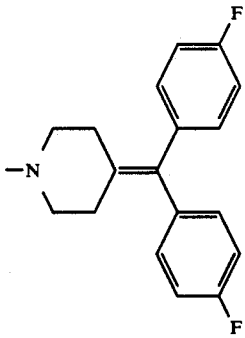 |
TABLE 29
| No. | R¹ | R² | A | B | D | n | Q | T |
|---|---|---|---|---|---|---|---|---|
| 397 | H | CH₃ | C=O | — | CH₂ | 2 | —(CH₂)₄— | 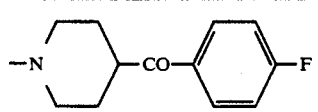 |

TABLE 29-continued
| No. | R¹ | R² | A | B | D | n | Q | T |
|---|---|---|---|---|---|---|---|---|
| 398 | " | " | " | " | " | " | " | 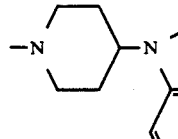 |
| 399 | " | Br | " | " | " | " | " | 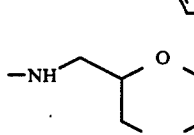 |
| 400 | " | $C_2H_5$ | " | " | " | " | " | 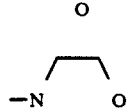 |
| 401 | " | " | " | " | " | " | " | 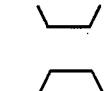 |
| 402 | " | $CH_3$ | " | " | " | " | " | 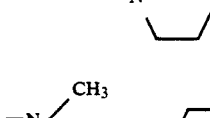 |
TABLE 30
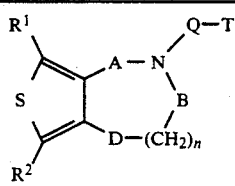
| No. | R¹ | R² | A | B | D | n | Q | T |
|---|---|---|---|---|---|---|---|---|
| 403 | H | $CH_3$ | C=O | — | $CH_2$ | 2 | $-(CH_2)_4-$ | 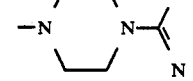 |
| 404 | " | " | " | " | " | " | " |  |
| 405 | " | Br | " | " | " | " | " |  |

TABLE 30-continued

| No. | R¹ | R² | A | B | D | n | Q | T |
|---|---|---|---|---|---|---|---|---|
| 406 | " | " | " | " | " | " | " | piperazine-N-(3-CF₃-phenyl) |
| 407 | " | Cl | " | " | " | " | " | piperazine-N-(2-OCH₃-phenyl) |
| 408 | " | CH₃ | " | " | " | " | " | piperazine-N-(5-chloro-benzoxazol-2-yl) |
| 409 | " | SO₂CH₃ | " | " | " | " | " | piperazine-N-(2,3-dimethylphenyl) |
| 410 | " | COCH₃ | " | " | " | " | " | piperazine-N-CH(phenyl)₂ |
| 411 | " | " | " | " | " | " | " | piperazine-N-(benzisothiazol-3-yl) |
| 412 | " | Br | " | " | " | " | " | piperazine-N-(CH₂)₁₅CH₃ |
| 413 | " | CH₃ | " | " | " | " | " | piperazine-N-CH(phenyl)(4-Cl-phenyl) |

TABLE 30-continued

Structure: R¹ on thiophene with S, R² substituent, A-N(Q-T)-B-D-(CH₂)ₙ fused system

| No. | R¹ | R² | A | B | D | n | Q | T |
|-----|----|----|---|---|---|---|---|---|
| 414 | " | " | " | " | " | " | " | 1-methylpiperidin-4-ylidene-bis(4-fluorophenyl)methane |

TABLE 31

| No. | R¹ | R² | A | B | D | n | Q | T |
|-----|----|----|---|---|---|---|---|---|
| 415 | H | CH₃ | C=O | — | CH₂ | 2 | —(CH₂)₄— | 4-(4-fluorobenzoyl)piperidin-1-yl |
| 416 | " | " | " | " | " | " | " | 4-(2-oxo-2,3-dihydro-1H-benzimidazol-1-yl)piperidin-1-yl |
| 417 | " | Br | " | " | " | " | " | —NH-CH₂-(1,4-benzodioxan-2-yl) |
| 418 | " | C₂H₅ | " | " | " | " | " | morpholino |
| 419 | " | " | " | " | " | " | " | piperidino |
| 420 | " | CH₃ | " | " | " | " | " | —N(CH₃)CH₂CH₂-(3,4-dimethoxyphenyl) |

We claim:
1. A fused thiophene compound of the formula:

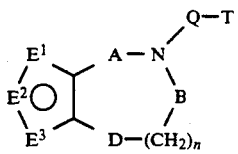

or a pharmaceutically acceptable acid addition salt thereof, whereas in said formula (I), one of $E^1$, $E^2$ and $E^3$ is a sulfur atom and the other two are C—$R^1$ and C—$R^2$, respectively; $R^1$ and $R^2$ are the same or different and each is hydrogen, halogen, nitro, amino, cyano, hydroxyl, formyl, $C_1$–$C_{18}$ alkyl, $C_1$–$C_8$ alkoxy, halo-$C_1$–$C_4$ alkyl, phenyl- or naphthyl-$C_1$–$C_4$ alkyl, $C_2$–$C_8$ alkanoyl, benzoyl, naphthoyl, nicotinoyl, thenoyl, furoyl, $C_1$–$C_2$ alkoxy-$C_1$–$C_4$ alkyl, $C_2$–$C_3$ alkanoyloxy-$C_1$–$C_3$ alkyl, benzoyloxy-$C_1$–$C_4$ alkyl, hydroxy-$C_1$–$C_4$ alkyl, $C_2$–$C_3$ alkanoyloxy-$C_2$–$C_4$ alkanoyl, benzoyloxy-$C_2$–$C_4$ alkanoyl, $C_1$–$C_4$ alkoxy-$C_2$–$C_3$ alkanoyl, Hydroxy-$C_2$–$C_4$ alkanoyl, phenoxy-$C_2$–$C_4$ alkanoyl, halo-$C_2$–$C_4$ alkanoyl, $C_1$–$C_4$ alkylthio, $C_1$–$C_4$ alkylsulfinyl, $C_1$–$C_4$ alkylsulfonyl, phenyl- or naphthyl-thio, phenyl- or naphthyl-sulfinyl, phenyl- or naphthyl-sulfonyl, hydroxysulfonyl, halosulfonyl, sulfamoyl, N,N-di-$C_1$–$C_4$ alkyl-sulfamoyl, piperidinosulfonyl, morpholinosulfonyl, carboxyl, $C_2$–$C_4$ alkanoylamino, benzoylamino, $C_1$–$C_4$ alkoxy-carbonyl, carbamoyl, N,N-di-$C_1$–$C_2$ alkyl-carbamoyl, piperidinocarbonyl, N- or N,N-di-$C_1$–$C_4$ alkylamino, N-methyl-N-benzylamino or piperidino; D is —$CH_2$— or —$S(O)_m$— in which m is 0, 1 or 2; Q is straight alkylene having 1-10 carbon atoms or branched alkylene having 2-6 carbon atoms substituted by 1 to 2 methyl; T is primary amino of —$NH_2$; secondary amino of —$NHR_a$ wherein $R_a$ is $C_1$–$C_{18}$ alkyl, $C_3$–$C_7$ cycloalkyl, phenyl- or naphthyl-$C_1$–$C_4$ alkyl, pyridylmethyl, furylmethyl, thienylmethyl or (1,4-benzodioxan-2-yl)methyl; or tertiary amino of —$N(R_b)(R_c)$ wherein $R_b$ and $R_c$ are the same or different and each is $C_1$–$C_{18}$ alkyl, $C_3$–$C_7$ cycloalkyl, phenyl- or naphthyl-$C_1$–$C_4$ alkyl, pyridylmethyl, furylmethyl, thienyimethyl or (1,4-benzodioxan-2-yl)methyl, or $R_b$ and $R_e$ together with the adjacent nitrogen atom form a cyclic amino of the formula:

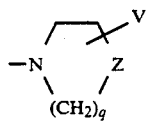

or

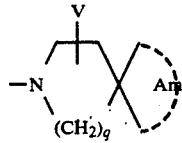

wherein q is an integer of 1 to 4; Z is methylene, an oxygen atom, a sulfur atom or N-$R^5$ in which $R^5$ is hydrogen, $C_1$–$C_{18}$ alkyl, cyano-$C_1$–$C_4$ alkyl, hydroxy--$C_1$–$C_4$ alkyl, phenyl, naphthyl, phenyl- or naphthyl-$C_1$–$C_4$ alkyl, $C_1$–$C_4$ alkoxy-carbonyl, diphenylmethyl, bis(4-fluoropheny)methyl, 2,2-diphenylethyl, 2,2-bis(4-fluoropheny)ethyl, pyridyl, thienyl, furyl, pyrimidinyl, 1,2-benzisothiazol-3-yl, 1,2-benzoisoxazol-3-yl, benzothiophen-3-or 4-yl, benzofuran-3- or 4-yl, quinolyl, isoquinolyl, benzoxazol-2-yl, pyrazinyl, piridazinyl, imidazolyl, thieno[3,2-c]pyridin-4-yl, furo[3,2-c]pyridin-4-yl, 2-oxo-1-benzimidazolyl, 2-thioxo-1-benzimidazolyl, 2,4-dioxohexahydropyrimidin-1-yl, hydantoin-1-yl, pyridylmethy, furylmethyl, thienylmethyl, (1,4-benzodioxan-2-yl) methyl,, $C_3$–$C_7$ cycloalkyl, $C_3$–$C_7$ cycloalkyl-methyl, $C_2$–$C_8$ alkanoyl, benzoyl, naphthoyl, nicotinoyl, thenoyl, furoyl, cinnamyl or adamantanemethyl; the substitutent V is hydrogen, hydroxyl, amino, carbamoyl, N- or N,N-di-$C_1$–$C_2$ alkylamino, anilino, N-acetylanilino, N-propionylanilino, pyrrolidinylamino, pyrrolidinyl, piperidino, hexamethyleneimino, morpholino, thiomorpholino, piperazinyl, homopiperazinyl, 4-substituted-piperazinyl, 4-substituted-homopiperazinyl, $C_2$–$C_8$ alkanoyl, benzoyl, naphthoyl, nicotinoyl, thenoyl, furoyl, phenyl, naphthyl, phenyl- or naphthyl-$C_1$–$C_4$ alkyl, phenyl- or naphthyl-$C_1$–$C_2$ alkylamino, $C_1$–$C_{18}$ alkyl, $C_1$–$C_8$ alkoxy, hydroxy-$C_1$–$C_4$ alkyl, $C_1$–$C_4$ alkoxy-carbonyl, pyridyl, thienyl, furyl, pyrimidinyl, 1,2-benzoisothiazol-3-yl, 1,2-benzoisoxazol-3-yl, benzothiophen-3- or 4-yl, benzofuran-3- or 4-yl, quinolyl, isoquinolyl, benzoxazol-2-yl, pyrazinyl, piridazinyl, imidazolyl, thieno 3,2-c]pyridin-4-yl, furo[3,2-c]pyridin-4-yl, 2-oxo-1-benzimidazolyl, 2-thioxo-1-benzimidazolyl, 2,4-dioxohexahydropyrimidin-1yl, hydantoin-1-yl, phenoxy-$C_1$–$C_3$ alkyl, anilino-$C_1$–$C_3$ alkyl, $C_1$–$C_2$ alkylamino-$C_1$–$C_2$ alkyl, $C_2$–$C_4$ alkanoylamino-$C_1$–$C_2$ alkyl, bis(4-fluorphenyl)-methylene or bis(4-chlorpheny)methylene and the number of V is 1 to 4; the cyclic amino of formula (I) may contain a carbonyl group in the cycle and further may be fused with benzene, naphthalene, furan, thiophene, pyridine or quinoline to form fused cyclic amino such as 1,2,3,4-tetrahydroisoquinolin-2-yl or phthalimido; ring $A_m$ of formula (2) may contain an amido bond in the cycle and further may contain an oxygen atom, a sulfur atom, a carbonyl and/or N—$R^6$ in which $R^6$ is hydrogen, $C_1$–$C_4$ alkyl or phenyl, and further the ring $A_m$ can be fused with a 5 to 7 membered saturated or unsaturated ring to form 2-oxo-1,2,3,5,6,7,8,8a-octahydroimidazo[1,2-a]pyridin-3-spiro-4'-piperidino; A and B are the same or different and each is carbonyl or thiocarbonyl, or thiocarbonyl, or A is —$CH_2$— and B is carbonyl or thiocarbonyl, and n is 1, 2 or 3 with the proviso that n is 2 or 3 when one of A and B is absent and the other is carbonyl or thiocarbonyl, and n is 1 or 2 when A and B are other combinations, and wherein, in the above definitions, phenyl, naphthyl, benzoyl, naphthoyl, nicotinoyl, thenoyl, furoyl, benzoyloxy, phenoxy, benzoylamino, benzylamino, pyridylmethyl, furylmethyl, thienylmethyl, (1,4-benzodioxan-2yl)methyl, anilino, pyridyl, thienyl, furyl pyrimidinyl, 1,2-benzoisothiazol-3-yl, 1,2-benzoisoxazol-3-yl, benzothiophen-3- or 4-yl, benzofuran-3- or 4-yl, quinolyl, isoquinolyl, benzoxazol-2-yl, pyrazinyl, piridazinyl, imidazolyl, thieno[3,2-c]pyridin-4-yl, furo[3,2-c]pyridin-4-yl, 2-oxo-1-benzimidazolyl, 2-thioxo-1-benzimidazolyl, 2,4-dioxohexahydropyrimidin-1-yl, hydantoin-1-yl, phenyl- or naphthyl-$C_1$–$C_4$ alkyl, diphenylmethyl, 2,2-diphenylethyl, cinnamyl or adamantanemethyl may optionally be substituted by 1 to 3 substituents selected from the group consisting of halogen, nitro, amino, cyano, halo-$C_1$–$C_4$ alkyl, hydroxyl, $C_1$–$C_4$ alkyl, $C_1$–$C_4$ alkoxy and $C_2$–$C_4$ alkenyl.

2. The compound or pharmaceutically acceptable acid addition salt thereof of claim 1 wherein T is —$NHR_a$ where $R_a$ is pyridylmethyl, furylmethyl, thienylmethyl or (1,4-benzodioxan-2-yl)methyl which may be optionally substituted by 1 to 3 substituents selected from the group consisting of halogen, nitro, amino, cyano, halo-$C_1$-$C_4$ alkyl, hydroxyl, $C_1$-$C_4$ alkyl, $C_1$-$C_4$ alkoxy and $C_2$-$C_4$ alkenyl.

3. The compound or pharmaceutically acceptable acid addition salt thereof of claim 1 wherein T is —N($R_b$) ($R_c$) where $R_b$ and $R_c$ are the same or different and each is $C_1$-$C_{18}$ alkyl, phenyl- or naphthyl-$C_1$-$C_4$ alkyl, pyridylmethyl, furylmethyl, thienylmethyl or (1,4-benzodioxan-2-yl)methyl, or $R_b$ and $R_c$ together with the adjacent nitrogen atom form a cyclic amino of the formula:

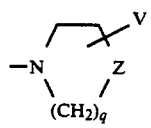

(1)

or

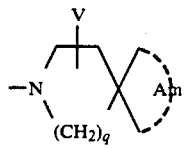

(2)

wherein q is an integer of 1 to 4; Z is methylene or N—$R^5$ in which $R^5$ is phenyl, naphthyl, diphenylmethyl, bis(4-fluorophenyl)methyl, 2,2-diphenylethyl, 2,2-bis(4-fluorophenyl)ethyl, pyridyl, thienyl, furyl pyrimidinyl, 1,2-benzoisothiazol-3-yl, 1,2-benzoisoxazol-3-yl, benzothiophen-3- or 4-yl, benzofuran-3- or 4yl, quinolyl, isoquinolyl, benzoxazol-2-yl, pyrazinyl, piridazinyl, imidazolyl, thieno[3,2-c]pyridin-4-yl, furo[3,2-c]pyridin-4-yl, 2-oxo-1-benzimidazolyl, 2-thioxo-1-benzimidazolyl, 2,4-dioxohexahydropyrimidin-1-yl, hydantoin-1yl, pyridylmethyl, furylmethyl, thienylmethyl, (1,4-benzodioxan-2-yl)methyl, $C_2$-$C_8$ alkanoyl, benzoyl, naphthoyl, nicotinoyl, thenoyl or furoyl; the substitutent V is hydrogen, hydroxyl, carbamoyl, pyrrolidinyl, piperidino, hexamethyleneimino, morpholino, thiomorpholino, piperazinyl, homopiperazinyl, 4-substituted-piperazinyl, 4-substituted-homopiperazinyl, phenyl, naphthyl, phenyl- or naphthyl-$C_1$-$C_2$ alkylamino, pyridyl, thienyl, furyl, pyrimidinyl, 1,2-benzoisothiazo-3-yl, 1,2-benzoisoxazol-3-yl, benzothiophen-3- or 4-yl, benzofuran-3- or 4-yl, quinolyl, isoquinolyl, benzoxazol-2-yl, pyrazinyl, piridazinyl, imidazolyl, thieno[3,2-c]pyridin-4-yl, furo[3,2-c]pyridin-4-yl, 2-oxo-1-benzimidazolyl, 2-thioxo-1-benzimidazolyl, 2,4-dioxohexahydropyrimidin-1-yl, hydantoin-1-yl, bis(4-fluorophenyl)methylene or bis(4-chlorophenyl)methylene and the number of V is 1 to 4; the cyclic amino of formula (I) may contain a carbonyl group in the cycle and further may be fused with benzene, naphthalene, furan, thiophene, pyridine or guinoline to form a fused cyclic amino such as 1,2,3,4-tetrahydroisoquinolin-2-yl or phthalimido; the ring $A_M$ of formula (2) may contain amido bond in the cycle and further may contain sulfur atom and/or N—$R^8$ ($R^8$ is phenyl) and further the ring $A_m$ can be fused with 5 to 7 membered saturated or unsaturated ring to form 2-oxo-1,2,3,5,6,7,8,8a-octahydroimidazo[1,2-a]pyridin-3-spiro-4'-piperidino; whereas in the above definitions, phenyl, naphthyl, benzoyl, naphthoyl, nicotinoyl, thenoyl, furoyl, pyridylmethyl, furylmethyl, thienylmethyl, (1,4-benzodioxan-2-yl)methyl, pyridyl, thienyl, furyl, pyrimidinyl, 1,2-benzoisothiazol-3yl, 1,2-benzoisoxazol-3-yl, benzothiophen-3- or 4-yl, benzofuran-3-or 4-yl, quinolyl, isoquinolyl, benzoxazol-2-yl, pyrazinyl, piridazinyl, imidazolyl, thieno[3,2-c]pyridin-4-yl, furo[3,2-c]pyridin-4-yl, 2-oxo-1-benzimidazolyl, 2-thioxo-1-benzimidazolyl, 2,4-dioxohexahydropyrimidin-1-yl, hydantoin-1-yl, phenyl- or naphthyl-$C_1$-$C_4$ alkyl, diphenylmethyl or 2,2-diphenylethyl may optionally be substituted by 1 to 3 substituents selected from the group consisting of halogen, nitro, amino, cyano, halo-$C_1$-$C_4$ alkyl, hydroxyl, $C_1$-$C_4$ alkyl, $C_1$-$C_4$ alkoxy and $C_2$-$C_4$ alkenyl.

4. The compound or pharmaceutically acceptable acid addition salt thereof of claim 1 wherein T is a cyclic amino of the formula:

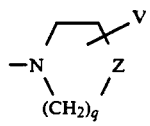

where Z is N—$R^5$ in which $R^5$ is pyrimidinyl or pyrimidinyl substituted by 1 to 3 substituents selected from the group consisting of halogen, nitro, amino, cyano, halo-$C_1$-$C_4$ alkyl, hydroxyl, $C_1$-$C_4$ alkyl, $C_1$-$C_4$ alkoxy and $C_2$-$C_4$ alkenyl, the substituent V is hydrogen, and q is 2.

5. The compound of claim 1 of the formula:

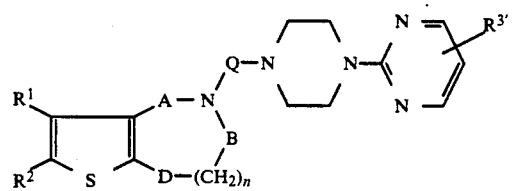

or pharmaceutically acceptable acid addition salts thereof, whereas in the above formula, $R^{3'}$ is hydrogen, halogen, nitro, amino, cyano, hydroxyl, $C_1$-$C_4$ alkyl, $C_1$-$C_4$ alkoxy or halo-$C_1$-$C_4$ alkyl and other symbols are as defined in claim 1.

6. The compound of claim 1 of the formula:

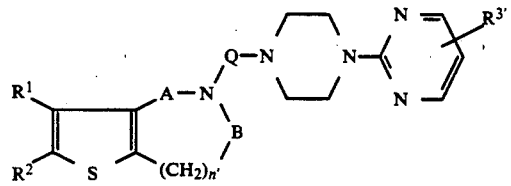

or a pharmaceutically acceptable acid addition salt thereof, whereas in the above formula, $R^1$ and $R^2$ are the same or different and each is hydrogen, halogen, nitro, amino, cyano, hydroxyl, formyl, $C_1$-$C_8$ alkyl, $C_1$-$C_8$ alkoxy, halo-$C_1$-$C_4$ alkyl, phenyl- or naphthyl-$C_1$-$C_4$ alkyl, $C_2$-$C_8$ alkanoyl, benzoyl, naphthoyl, nicotinoyl, thenoyl, furoyl, $C_1$-$C_2$ alkoxy-$C_1$-$C_4$ alkyl, $C_2$-$C_3$ alkanoyloxy-$C_1$-$C_3$ alkyl, benzoyloxy-$C_1$-$C_4$ alkyl, hydroxy-$C_1$-$C_4$ alkyl, $C_2$-$C_3$ alkanoyloxy-$C_2$-$C_4$ alkanoyl, benzoyloxy-$C_2$-$C_4$ alkanoyl, $C_1$-$C_4$ alkoxy-$C_2$-$C_3$ alkanoyl, hydroxy-$C_2$-$C_4$ alkanoyl, phenoxy-$C_2$-$C_4$ alkanoyl or halo-$C_2$-$C_4$ alkanoyl, $R^{3'}$ is as defined in claim 5, A and B are carbonyl groups, or one of A and B is absent and the other is a carbonyl group, n' is 2 or 3 when A and B are carbonyl groups and n' is 3 or 4 in the other case, and Q is a straight or branched chain alkylene having 1 to 10 carbon atoms.

7. The compound of claim 1 of the formula:

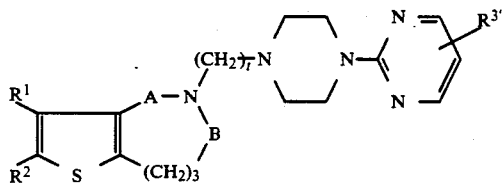

or a pharmaceutically acceptable acid addition salt thereof, whereas, in the above formula, $R^1$ and $R^2$ are as defined in claim 6, $R^{3'}$ is as defined in claim 5, t is an integer of 1 to 8, A and B are absent or carbonyl groups with the provisos that when A is absent, B is a carbonyl group, and when A is a carbonyl group, B is absent.

8. The compound of claim 1 or a pharmaceutically acceptable acid addition salt thereof, wherein T is a group of the formula:

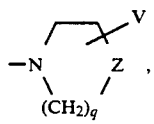

in the above formula, Z is methylene of N—$R^5$ in which $R^5$ is phenyl, naphthyl, diphenylmethyl, bis(4-fluorophenyl)methyl, 2,2-diphenylethyl, 2,2-bis(4-fluorophenyl)ethyl, pyridyl, thienyl, furyl, 1,2-benzoisothiazol-3-yl, 1,2-benzoisoxazol-3-yl, benzothiophen-3- or 4-yl, benzofuran-3- or 4-yl, quinolyl, isoquinolyl, benzoxazol-2-yl, pyrazinyl, piridazinyl, imidazolyl, thieno[3,2-c]pyridin-4-yl, furo[3,2-c]pyridin-4-yl, 2-oxo-1-benzimidazolyl, 2-thioxo-1-benzimidazolyl, 2,4-dioxohexahydropyrimidin-1-yl, hydantoin-1-yl, pyridylmethyl, furylmethyl, thienylmethyl, (1,4-benzodioxan-2-yl)methyl, $C_2$-$C_8$ alkanoyl, benzoyl, naphthoyl, nicotinoyl, thenoyl or furoyl; the substituent V is hydrogen, hydroxyl, carbamoyl, pyrrolidinyl, piperidino, hexamethyleneimino, morpholino, thiomorpholino, piperazinyl, homopiperazinyl, 4-substituted-piperazinyl, 4-substituted-homopiperazinyl, phenyl, naphthyl, phenyl- or naphthyl-$C_1$-$C_2$ alkylamino, pyridyl, thienyl, furyl, pyrimidinyl, 1,2-benzoisothiazol-3-yl, 1,2-benzoisoxazol-3-yl, benzothiophen-3- or 4-yl, benzofuran-3- or 4-yl, quinolyl, isoquinolyl, benzoxazol-2-yl, pyrazinyl, piridazinyl, imidazolyl, thieno[3,2-c]pyridin-4-yl, furo[3,2-c]pyridin-4-yl, 2-oxo-1-benzimidazolyl, 2-thioxo-1-benzimidazolyl, 2,4-dioxohexahydropyrimidin-1-yl, hydantoin-1-yl, bis(4-fluorophenyl)methylene or bis(4-chlorophenyl)methylene and the number of V is 1 to 4 and q is 2, whereas, in the above definitions, phenyl, naphthyl, benzoyl, naphthoyl, nicotinoyl, thenoyl, furoyl, pyridylmethyl, furylmethyl, thienylmethyl, (1,4-benzodioxan-2-yl)methyl, pyridyl, thienyl, furyl, 1,2-benzoisothiazol-3-yl, 1,2-benzoisoxazol-3-yl, benzothiophen-3- or 4-yl, benzofuran-3- or 4-yl, quinolyl, isoquinolyl, benzoazol-2-yl, pyrazinyl, piridazinyl, imidazolyl, thieno[3,2-c]pyridin-4-yl, furo[3,2-c]pyridin-4-yl, 2-oxo-1-benzimidazolyl, 2-thioxo-1-benzimidazolyl, 2,4-dioxohexahydropyrimidin-1-yl, hydantoin-1-yl, diphenylmethyl or 2,2-diphenylethyl may optionally be substituted by 1 to 3 substituents selected from the group consisting of halogen, nitro, amino, cyano, halo-$C_1$-$C_4$ alkyl, hydroxyl, $C_1$-$C_4$ alkyl, $C_1$-$C_4$ alkoxy and $C_2$-$C_4$ alkenyl.

9. The compound of claim 1 selected from the group consisting of 2-bromo-5-[4-(4-(2-pyrimidinyl)-1-piperazinyl)butyl]-5,6,7,8-tetrahydro-4H-thieno[3,2-c]azepin-4-one, 2-methyl-5-[4-(4-(2-pyrimidinyl)-1-piperazinyl)butyl]-5,6,7,8-tetrahydro-4H-thieno[3,2-c]azepin-4-one, 2-ethyl-5-[4-(4-(2-pyrimidinyl)-1-piperazinyl)butyl]-5,6,7,8-tetrahydro-4H-thieno[3,2-c]azepin-4-one, 2-acetyl-5-[4-(4-(2-pyrimidinyl)-1-piperazinyl)butyl]-5,6,7,8-tetrahydro-4H-thieno[3,2-c]azepin-4-one, 2-(1-hydroxyethyl)-5[4-(4-(2-pyrimidinyl)-1-piperazinyl)butyl]-5,6,7,8-tetrahydro-4H-thieno[3,2-c]azepin-4-one, 5-[4-(4-(1,2-benzisothiazol-3-yl)-1-piperazinyl)butyl]-2-methyl-5,6,7,8-tetrahydro-4H-thieno[3,2-c]azepin-4-one, 5-[4-[(1,4-benzodioxan-2-yl)methylamino]butyl]-2-methyl-5,6,7,8-tetrahydro-4H-thieno[3,2-c]azepin-4-one, 2,3-dihydro-4-[4-(4-(2-pyrimidinyl)-1-piperazinyl)butyl]thieno[3,2-f]-1,4-thiazepin-5(4H)-one, 7-bromo-2,3-dihydro-4-[4-(4-(2-pyrimidinyl)-1-piperazinyl)butyl]thieno[3,2-f]-1,4-thiazepin-5(4H-one, 7-acetyl-2,3-dihydro-4-[4-(4-(2-pyrimidinyl)-1-piperazinyl)butyl]thieno[3,2-f]-1,4-thiazepin-5(4H)-one, 7-ethyl-2,3-dihydro-4-]4-(4-(2-pyrimidinyl)-1-piperazinyl)butyl]thieno[3,2-f]-1,4-thiazepin-5(4H)-one, 4-[4-(4-(1,2-benzisothiazol-3-yl)-1-piperazinyl)butyl]-2,3-dihydrothieno[3,2-f]-1,4-thiazepin-5(4H)-one, 5-[4-(4-(bis(4-fluorophenyl)methyl)-1-piperazinyl)butyl]-2-methyl-5,6,7,8-tetrahydro-4H-thieno[3,2-c]azepin-4one, 2-methyl-5-[4-(4-(2-pyrimidinyl)-1-piperazinyl)butyl]-5,6,7,8-tetrahydro-4H-thieno[3,2-c]azepin-4,6-dione, 7-methyl-4-[4-(4-(2-pyrimidinyl)-1-piperazinyl)butyl]-2,3-dihydro-4H-thieno[3,2-f][1,4]thiazepin-3,5-dione, 5-[4(4-(3-trifluoromethylphenyl)-1-piperazinyl]-5,6,7,8-tetrahydro-4H-thieno[3,2-c]azepin-4-one, 5-[4-(4-(2,3-dimethylphenyl)-1-piperazinyl)butyl]-2-methyl-5,6,7,8-tetrahydro-4H-thieno[3,2-c]azepin-4-one, 5-[4-(4-(2-methoxyphenyl)-1-piperazinyl)butyl]-2-methyl-5,6,7,8-tetrahydro-4H-thieno[3,2-c]azepin-4-one, 2,3-dihydro-4-[4-(4-(2-methoxyphenyl)-1-piperazinyl)butyl]-7-methylthieno[3,2-f]-1,4-thiazepin-5(4H)-one and 4-[4-(4-bis(4-fluorophenyl)methylene)piperidino)-butyl]-2,3-dihydro-7-methylthieno[3,2-f]-1,4-thiazepin-5(4H)-one or pharmaceutically acceptable acid addition salt thereof.

10. The compound of claim 1 selected from the group consisting of 2-bromo-5-[4-(4-(2-pyrimidinyl)-1-piperazinyl)butyl]-5,6,7,8-tetrahydro-4H-thieno[3,2-c]azepin-4one, 2-methyl-5-[4-(4-(2-pyrimidinyl)-1-piperazinyl)-butyl]-5,6,7,8-tetrahydro-4H-thieno[3,2-c]azepin-4-one, 2-ethyl-5-[4-(4-(2-pyrimidinyl)-1-piperazinyl)butyl]-5,6,7,8-tetrahydro-4H-thieno[3,2-c]azepin-4-one, 2-acetyl-5-[4-(4-(2-pyrimidinyl)-1-piperazinyl)butyl]-5,6,7,8-tetrahydro-4H-thieno[3,2-c]azepin-4-one, 2(1-hydroxyethyl)-5-[4-(4-(2-pyrimidinyl)butyl]-5,6,7,8-tetrahydro-4H-thieno[3,2-c]azepin-4-one, 2,3-dihydro-4-[4-(4-(2-pyrimidinyl(-1-piperazinyl)-butyl]thieno[3,2-f]-1,4-thiazepin-5(4H)-one, 7-bromo-2,3-dihydro-4-[4-(4-(2-pyrimidinyl)-1-piperazinyl)butyl]thieno[3,2-f]-1,4-thiazepin-5(4H)-one, 7-acetyl-2,3-dihydro-4-[4-(4-(2-pyrimidinyl)-1-piperazinyl)butyl]thieno]3,2-f]-1,4-thiazepin-5(4H)-one, 7-ethyl-2,3-dihydro-4-[4-(4-(2-pyrimidinyl)-1-piperazinyl)butyl]thieno[3,2-f]-1,4-thiazepin-5(4H)-one, 2-methyl-5-[4-(4-(2-pyrimidinyl)-1-piperazinyl)-butyl]-5,6,7,8-tetrahydro-4H-thieno[3,2c]azepin-4,6-dione and 7-methyl-4-[4-(4(2-pyrimidinyl)-1-piperazinyl)butyl]-2,3-dihydro-4H-thieno[3,2-f][1,4]thiazepin-3,5-dione or pharmaceutically acceptable acid addition salt thereof.

11. A fused thiophene compound of the formula:

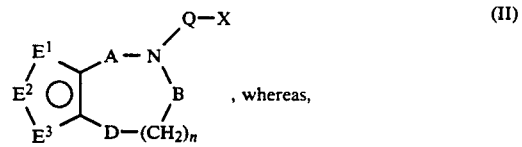

, whereas, in the formula, X is hydroxyl, a reactive atom or group derived from hydroxyl which is selected from the group consisting of methanesulfonyloxy and paratoluenesulfonyloxy a group of —CO—R³ in which, cyano, carbamoyl or nitro, and other symbols are as defined in claim 1.

12. The compound of claim 11 of the formula:

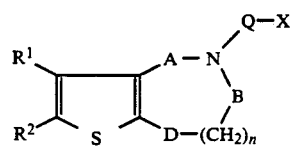

whereas, in the formula, each symbol is as defined in claims 1 and 11.

13. A pharmaceutical composition consisting of a fused thiophene compound or the pharmaceutically acceptable acid addition salt thereof of claim 1 and pharmaceutical carriers.

* * * * *